Figure 1A:
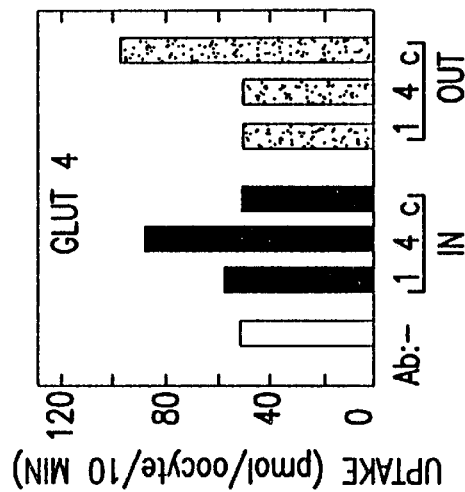

United States Patent [19]

Fischbarg et al.

[11] Patent Number: 5,940,307

[45] Date of Patent: Aug. 17, 1999

[54] METHOD FOR PREDICTING THE TENDENCY OF A PROTEIN TO FORM AMPHIPHILIC α OR β STRUCTURE

[75] Inventors: Jorge Fischbarg, New York; Ferenc Czegledy, Cold Spring Harbor; Pavel Iserovich, Brooklyn; Jun Li; Min Cheung, both of New York, all of N.Y.

[73] Assignee: The Trustees of Columbia University in the City of New York, New York, N.Y.

[21] Appl. No.: 08/355,844

[22] Filed: Dec. 14, 1994

[51] Int. Cl.[6] ............................. G06F 17/11; G06F 17/50
[52] U.S. Cl. ............................................ 364/496; 364/578
[58] Field of Search ..................... 364/496–499, 364/578

[56] References Cited

U.S. PATENT DOCUMENTS

| 4,853,871 | 8/1989 | Pantoliano et al. ...................... 364/496 |
| 4,939,666 | 7/1990 | Hardman ................................. 364/496 |
| 5,265,030 | 11/1993 | Skolnick et al. ......................... 364/496 |

OTHER PUBLICATIONS

Fischbarg et al., "Are most transporters and channels beta barrels?," *Molecular & Cellular Bicrochemistry*, vol. 140, No. 2 Dec. 9, 1994, pp. 147–162.

Holbrook et al., "PROBE: A computer program employing an integrated neural network approach to protein structure prediction," *BioCOMPUTING*, vol. 14, No. 6, 1993, pp. 984–989.

Yoshimura, et al., "Fusion of phospholipid vesicles induced by an amphiphilic model peptide: close correlation between fusogenicity and hydrophobicity of the peptide in an α–Helix," *Biochemistry*, vol. 31, No. 26, 1992, pp. 6119–6126.

Kaiser, et al., "Amphiphilic sencondary structure: design of peptide hormones," *Science*, vol. 223, 1984, pp. 249–256.

Miller et al, "Identifying repeated structural elements in folded protein", *Proc. of 27th Annual Hawaii Int'l Conf. on System Sciences*, 1994, pp. 235–244.

Daugherity, W. "Aneural–fuzzy system for the protein folding problem," *Industrial Fuzzy Control & Intelligent System*, *1993 Int'l Conference*, 1993, pp. 47–49.

Hermans, J., "Molecular dynamics simulations of helix and turn propensities in model peptides," *Current Opinion in Structural Biology*, vol. 3, No. 2, 1993, pp. 270–276.

Chrispeels and Agre, TIBS, 1994, 19:421–425.

Fischbarg et al., 1993, Proc. Natl. Acad. Sci. U.S.A. 90:11658–11661.

Vera et al., 1993, nature 364:79–82.

Fischbarg et al., 1993, Alfred Benzon Symp. 34:432–446.

Rost and Sander, 1992, Nature 360:540.

(List continued on next page.)

*Primary Examiner*—Emanuel T. Voeltz
*Assistant Examiner*—Kyle J. Choi
*Attorney, Agent, or Firm*—Brumbaugh, Graves, Donohue & Raymond

[57] ABSTRACT

The present invention relates to a method for predicting the tendency of a protein to form amphiphilic α or β structure, wherein a series of values for U are calculated for spans of x residues, where the equation $$U_{\alpha x} = H_x + \mu_{\alpha x} - <pt>$$

is used to predict regions of amphiphilic α structure and the equation $$U_{\beta x} = H_x + \mu_{\beta x} <pt>$$

is used to predict regions of amphiphilic β structure, and where $H_x$ is the average hydrophobicity for a span of x residues, $\mu_x$ is the hydrophobic moment, and <pt> is the position dependent turn propensity. When the values for $U_{\alpha x}$ and $U_{\beta x}$ are represented graphically, peaks are predicted to represent regions of α and β structure, respectively.

6 Claims, 55 Drawing Sheets

OTHER PUBLICATIONS

Hasegawa et al., 1992, Science, 258:936–942.
Nikaido et al., 1992, Science, 258:936–942.
Hashiramoto et al., 1992, J. Biol. Chem., 267:17502–17507.
Cowan et al., 1992, Nature, 358:727–733.
Sofue et al., 1992, Biochem. J., 288:669–674.
Park et al., 1992, Proteinj Science 1:1032–1049.
Preston et al., 1992, Science, 256:385–387.
Haris et al., 1992, Trends Biochem. Sci. 17:328–333.
Bogusz et al., 1992, Protein–Eng., 5(4):285–293.
Asano et al., 1992, FEBS. Lett., 298:129–132.
Parker et al., 1992, J. Mol. Biol., 224:639–657.
Kaback, Int. Rev. Cytol., 1992, 137A:97–125.
Asano et al., J. Biol. Chem., 1991, 266:24632–24636.
Welte et al., Biochim. Biophys. Acta, 1991, 1080:271–274.
Zhang et al., J. Clin. Invest., 1991, 88:1553–1558.
Perczel et al., Protein Eng., 1991, 4:669–679.
Bowie et al., Science, 1991, 253:164–170.
Radding, J. Theor Biol., 1991, 150:239–249.
MacKinnon, Nature, 1991, 350:232–235.
Weiss et al., FEBS Lett., 1991, 280:379–382.
Karlin A., "Explorations of the nicotinic acetylcholne receptor", The Harvey Lecture Series, 1991, 85:71–107.
Oka et al., Nature, 1990, 345:550–553.
Farber et al., TIBS, 1990, 15:228–234.
Fischbarg et al., Proc. Natl. Acad. Sci. USA, 1990, 87:3244–3247.
Vera et al., Mol. Cell Biol., 1990, 10:743–751.
Carruthers, Phys. Rev., 1990, 70:1135–1175.
Davies, Biochem J., 1990, 266:799–808.
Carruthers et al., Biochemistry, 1989, 28:8337–8346.
Preelige and Fasman, in "Predictions of Protein Structure and the Principles of Protein Conformation", Fasman, ed., Plenum Press, New York, 1989, pp. 391–416.
Deziel et al., Int. J. Biochem., 1989, 21:807–814.
Qian and Sejnowski, J. Mol. Biol., 1988, 202:865–884.
Alvarez, J. Biol. Chem., 1987, 262:3502–3509.
Chin et al., Proc. Natl. Acad. Sci. U.S.A., 1987, 84:4113–4116.
Chin et al., J. Biol. Chem., 1986, 261:7101–7104.
Jung et al., J. Biol. Chem., 1986, 261:9155–9160.
Paul and Rosenbusch, EMBO J., 1985, 4:1593–1597.
Mueckler et al., Science, 1985, 299:941–945.
Eisenberg et al., Proc. Natl. Acad. Sci. U.S.A., 1984, 81:140–144.
Kaiser and Kezdey, 1984, Science, 223(7):249.
Kyte and Doolittle, J. Mol. Biol., 1982, 157:105–132.
Matthews, Biochim. Biophys. Acta, 1975, 405:442–451.
Needleman et al., J. Mol. Biol., 1970, 48:443–453.

```
Ompf                                              ..........  ..........  ..........  ..........  ..........
S16070                                            ..........  ..........  ..........  ..........  ..........
Gtr1_Human    MEPSSKKLTG  RLMLAVGGAV  LGSLQFGYNT   GVINAPQKVI  EEFYNQTVVH  50

Ompf          ....DGNKVD  LYGKA.VGLH  YESKGNGENS   YG.....GNG  DMTYARLGFK
S16070        ......EVK   LSGDARMGVM  Y]...NGDDWN  FS.....SRS  .....RVLFT
Gtr1_Human    RYGESILPTT  LTTLWSLSVA  IRSVGQMIGS   FSVGLFVNRF  GRRNSMLMMN  100

Ompf          GETQINSDLT  GYGQWEYNFQ  GN......NS   EGADAQTGNK  TRLAFAGLKY
S16070        MSGTTDSGL.  ....EFGASFK AH......ES   VGARTGEDGT  VFLSGAFGKI
Gtr1_Human    LLAFVSAVLM  GFSKLGKSFE  MLILGRFIIG   VYCGLTTGFV  PMYVGEVSPT  150

Ompf          ADVGSFDYGR  N....YGVVY  DALGYDDMLP   EFGGDTAY..  SDDFFVGRVG
S16070        EMGDAKGASE  AL]...FGDLY E.VGYTDLDD   RGGNDIPYLT  GDERLTAEDN
Gtr1_Human    AFRGALGTLH  QLGIVVGILI  AQVFGLDSIM   GNKDLWPLLL  SIIFIRALLQ  200

Ompf          GVAT..YRNS  NFFGLV..DG  LNFAVQYLGK   NERDTARRSN  GDGVGGSISY
S16070        PVLL..YTYS  .....A]..GA FSVAAS.MSD   GKVGETSEDD  AQEMAVAAAY
Gtr1_Human    CIVDPFCPES  PRFLLINRNE  ENRAKSVLKK   LRQTADVTHD  LOEMKPESRQ  250

Ompf          EYEG..FGIV  GAYGAADRTN  LOEAQPLGNG   KKAEQWATGL  KYDANNIYLA
S16070        TFGN..YTVG  LGYEKIDSPD  ....TALMAD   MEQLELAAIA  KFGATNV..K
Gtr1_Human    MMREKKVTIL  ELDRSPAYRQ  PILIAVVLQL   SQQLSGINAV  FYYSTSIFEK  300

Ompf          ANYGETRNAT  PITNKFTNTS  GFANKTQDVL   LVAQYQFDFG  LRPSI.AYTK
S16070        AYYADGELDR  DFARAVFDLT  PVAAAATAVD   HKA...YGLS  VDSTFGATTV
Gtr1_Human    AGVQQPVYAT  .IGSGIVNTA  PTVVSLFVVE   RAGRRTLHLI  GLAGMAGGAI  350

Ompf          SKAKDVEGIG  DVDLVNYFEV  GATY....YF   NKNMSTYVDY  IINQIDSDNK
S16070        GGYVOVLDID  TIDDVTYYGL  GASY....DL   GGGAS.....  IVGGI.ADND
Gtr1_Human    LMTIALALLE  QLPWMSYLSI  VAIFGFVAFF   EVGPGPIPWF  IVAELDSQGP  400

Ompf          LGVGSDDTV.  ........AVG IVYQFAEIYN   K.........  ..........
S16070        LP.NSDNVA.  ........DLG VKFKF.....   ..........  ..........
Gtr1_Human    RPAAIAVAGF  SNWTSNFIVG  MCFOYVEQLC   GPYVFIIFTV  LLVLFFIRTY  450

Ompf          ..........  ..........  ..........   ..........  ..........
S16070        ..........  ..........  ..........   ..........  ..........
Gtr1_Human    FKVPETKGFT  FDEIASGFRQ  GGASQSDKTP   EELFHPLGAD  SQV         493
```

FIG.2

```
1   '/* PROGRAM UNION
2   '/* J. FISCHBARG, F. CZEGLEDY, P. ISEROVICH; OCT. 1992-oct. 1993 */
3   '/*
4   '/* TO CALCULATE AVG. HYDROPHOBICITY, AMPHIPHILICITY AND TURN POENTIAL
5   '/*  OUTPUT COLUMNS FOR SYMPHONY OR ORIGIN
6   '/* please do not use word "UNION" in program (PB3 has command UNION)
7   ' TAKES INPUT FROM DEFAULT TEXT FILE, NAMELY:
8   '    DEFAULTS = path$ + "DEFAULT.TEX"
9   ' TAKES SEQUENCE DATA FROM:
10  fileinp$ = path$ + filein$ + ".seq"
11  ' WRITES PUTPUT DATA TO:
12  fileout$ = path$ + fileou$ + ".dat"
13  ' p1 = round(houtspann(L), 2)
14  "  p2=round(amphioutalphan(L),2)
15  "  P3=round(amphioutbetan(L),2)
16  ' p4 = round(ptseqn(L), 2)
17  ' p5 = round(unnalphan(L), 2)
18  ' p6 = round(unnbetan(L), 2)
19  ' p7 = round(houtmheln(L), 2)
20  $STATIC
21  $STRING 1
22  DECLARE SUB NORMAL (DUM!(), nlen%, DUMM!())
23  DECLARE SUB UN (psteqn!(), HOUTN!(), AMPHIOUTN!(), nlen%, UNN!())
24  common path$,filein$,fileinp$,nseq,houtspann(1)psteqn(1),unnalphan(1),_
25  unnbetan(1),houtmhein(1)
26  DEFINT I-N
27  naa = 20
28  NSEQ = 1500
29  nwin = 26
30  DIM symbols$(naa)
31  DIM seqh(NSEQ)
32  DIM seqn(NSEQ)
33  DIM seqt(NSEQ)
34  DIM seq$(NSEQ)
35  DIM vkyte(naa)
36  DIM pturn(naa)
37  DIM nwsize(naa)
38  DIM hout(NSEQ)
39  DIM houtmhein(NSEQ)
40  DIM amphiout(NSEQ)
41  'DIM houtmhein(nseq)           'normalized
42  DIM houtspann(NSEQ)            'normalized
43  DIM AMPHIOUTBETAN(NSEQ)        'normatized
44  DIM AMPHIOUTALPHAN(NSEQ)       'normalize
45  DIM turnprop(NSEQ)
46  DIM turnpropn(NSEQ)            'normalized
47  DIM UNNALPHA(NSEQ)
48  DIM unnalphan(NSEQ)            'normalized
49  DIM UNNBETA(NSEQ)
50  DIM unnbetan(NSEQ)
```

FIG.10a

```
51   DIM turnprops(NSEQ)
52   DIM DUM(NSEQ)
53   DIM DUMN(NSEQ)              'normalized
54   DIM pt(20, 4)
55   DIM PTSEQ(NSEQ)
56   DIM ptseqn(NSEQ)            'normalized
57    aacodes$ = "ARNDCQEGHILKMFPSTWYV"
58   CL$
59   'PRINT " ENTER PATH   (WITH ...\)"
60   'INPUT PATH$
61   path$ = "C:\MM\BEAUFORT\"
62   DEFAULT = path$ + "DEFAULT.TEX"
63   OPEN DEFAULT$ FOR INPUT AS #5
64   INPUT #5, filein$, filleou$, angalpha, angbeta, WHEL, span, UW
65   CLOSE #5
66   fileinp$ = path$ + filein$ + ".seq"
67   fileout$ = path$ + fileou$ + ".dat"
68   'Kyte-Doolittle scale
69   '     1,   2,   3,   4,   5,   6,   7,   8,   9,   10
70   'LIST:A,   R,   N,   D,   C,   Q,   E,   G,   H,   I
71   DATA 1.8,-4.5,-3.5,-3.5, 2.5,-3.5,-3.5,-0.4,-3.2,4.5
72   '          11,  12,  13,  14,  15,  16,  17,  18,  19,  20
73   '           L,   K,   M,   F,   P,   S,   T,   W,   Y,   V
74   DATA 3.8,-3.9, 1.9, 2.8,-1.6,-0.8,-0.7,-0.9,-1.3, 4.2
75   '   Chou-Fasman turn propensities - scaled to correspond to KD indices
76   '     1,   2,   3,   4,   5,   6,   7,   8,   9,   10
77   '     A,   R,   N,   D,   C,   Q,   E,   G,   H,   I
78
79   DATA -2.9,-0.5, 4.5, 3.7, 1.4,-0.3,-2.3, 4.5 -0.5,-4.5
80   '          11,  12,  13,  14,  15,  16,  17,  18,  19,  20
81   '           L,   K,   M,   F,   P,   S,   T,   W,   Y,   V
82   DATA -3.5, 0.0,-3.4,-3.4, 4.2, 3.4,-0.5,-0.5, 1.0,-4.3
83
84
85   start:
86   CLS
87   DUMMY = 0
88   PRINT "1. FILE NAME FOR INPUT "; fileinp$
89   PRINT "2. FILE NAME FOR OUTPUT "; fileout$
90   PRINT "3. ANGLE FOR ALPHA/BETA STRUCTURES (HYDROPHOBIC MOMENT) "
91   PRINT "  ALPHA STRUCTURE=";angalpha; "BETA STRUCTURE= "; angbeta
92   PRINT "4. WINDOW SIZE FOR MEMBRANE HELICES "; WHEL
93   PRINT "5. SPAN FOR UNION "; span
94   PRINT "6. WINDOW SIZE FOR SMOOTHING UNION "; UW
95   PRINT "9. TO END SESSION "
96   PRINT " TO CHANGE ANY SETTINGS ENTER CORRESPONDING NUMBER "
97   PRINT " IF YOU ARE READY TO CONTINUE PRESS ENTER "
98    INPUT DUMMY
99    SELECT CASE DUMMY
100    CASE 1
```

FIG.10b

```
101     GOSUB FILENAMEINPUT
102   ' CASE  2
103   '         GOSUB  FILENAMEOUTPUT
104     CASE 3
105       GOSUB MOMENTANGLE
106     CASE 4
107       GOSUB ALPHAWINDOW
108     CASE 5
109       GOSUB BETAWINDOW
110     CASE 6
111       GOSUB UNNWINDOW
112     CASE 9
113       GOTO salida
114     CASE 0
115       OPEN DEFAULTS FOR OUTPUT AS #6
116       WRITE #6, filein$, fileou$, angalpha, angbeta, WHEL, span, UW
117       CLOSE #6
118       GOSUB WORKING
119     END SELECT
120     PRINT 3
121     GOTO start
122
123     FILENAMEINPUT:
124     SHELL "DIR " + path$ + "*.SEQ/W"
125     LOCATE 20, 1
126     PRINT " ENTER FNAME (ONLY) FOR UNPUT SEQ; PROG ADDS DEF FILE TYPES .SEQ & .DAT"
127     INPUT filein$
128     fileou$ = filein$
129     fileinp$ = path$ + filein$ + ".seq"
130     fileout$ = path$ + fileou$ + ".dat"
131      RETURN
132
133
134     WORKING:
135     OPEN fileing$ FOR INPUT AS #1
136     INPUT #1, sequence$
137     CLOSE #1
138     turninput$ = path$ + "inp.dat"
139      OPEN turninput$ FOR INPUT AS #3
140      FOR I = 1 TO 20
141        FOR m = 1 TO 4
142        INPUT #3, pt(I, m)
143        NEXT m
144      NEXT I
145      CLOSE #3
146      FOR n = 1 TO 20
147        READ vkyte(n)
148        symbols$(n) = MID$(aacodes$, n, 1)
149      NEXT n
150      FOR n = 1 TO 20
```

FIG.10c

```
151    READ pturn(n)    'acquire Chou-Fasman turn potentials
152    NEXT n
153    RESTORE
154    PRINT " ............ WORKING ................"
155    nlen = LEN(sequences)
156    FOR n = 1 TO nlen
157    seq$(n) = MID$(sequence$, n, 1)
158    NEXT n
159     ' end of while loop
160           FOR I = 1 TO nlen        ' from 1 TO Length of sequence */
161    FOR k = 1 TO 20
162    IF seq$(I) = symbols$(k) THEN ' identify ordinal FOR as */
163      seqh(I) = vkyte(k)         ' and assign hydrphobicity value to residue*/
164      seqt(I) = pturn(k)
165      seqn(I) = k         ' assign residue name number*/
166    END IF
167      NEXT k
168      NEXT I
169    'cls
170    '      PRINT "A.A.: " seq$(i), "Hydr. f.= " seqh(i)
171    'j=5
172    ' FOR l=1 TO (nlen-j+1)  'L: beginn. of window; calcs. all residues in wind.*/
173    "         turnacc = 0
174    ,   'FOR i=L TO (L+j-1)           'Loop on i through all res. in window */
175    '              turnacc = turnacc + seqt(i)
176      'NEXT f
177
178    '       m = L-1+(j+1)/2       ' define center of window */
179    '       turnprop(m) = turnacc/j 'calculate average turn propensity
180    ' NEXT L
181    FOR n = 2 TO (nlen - 2)
182    PTSEQ(n) = pt(seqn(n - 1), 1) * pt(seqn(n), 2) * pt(seqn(n + 1), 3) * pt(seqn(n + 2), 4)
183    NEXT n
184    PTSEQ(1) = PTSEQ(2)
185    PTSEQ(nlen) = PTSEQ(nlen -2)
186    PTSEQ(nlen -1) = PTSEQ(nlen -2)
187    CALL NORMAL(PTSEQ(), nlen, ptseqn())
188
189       ' HYDROPHOBICITY CALCULATION FOR MEMBRANE HELICES * /
190    FLAG = 1 ' calculate hydrofobicity* /
191    j =  WHEL            ' window
192    GOSUB MAIN       ' and we will get hout(m)
193    CALL NORMAL(hout(), nlen, houtmheln()) ' and we will get houtmheln*/
194
195       ' HYDROPHOBICITY CALCULATION FOR SHORT SPAN
196    FLAG = 1 ' calculate hydrofobicity* /
197    j = span          ' window
198    GOSUB MAIN       ' and we will get hout(m)
199    CALL NORMAL(hout(), nlen, houtspann()) ' and we will get houtspann*/
200
```

FIG.10d

```
201    'calculation alpha moment*/
202    FLAG = 0
203    j = span
204    ANGLE = angalpha
205    GOSUB MAIN           ' and we will get amphiout(m)*/
206    CALL NORMAL(amphiout(), nlen, AMPHIOUTALPHAN())'and we will get AMPHIOUTALPHAN*/
207
208    ' calculation beta moment*/
209    FLAG = 0 'gives amphiout output
210    j = span
211    ANGLE = angbeta
212    GOSUB MAIN           ' we get beta moment, amphiout(m)*/
213    CALL NORMAL(amphiout(), nlen, AMPHIOUTBETAN())  ' and we will get AMPHIOU
214
215    'calculate union alpha
216    CALL UN(ptseqn(), houtspann(), AMPHIOUTALPHAN(), nien, UNNALPHA())
217    CALL NORMAL(UNNALPHA(), nlen, unnalphan())
218    'calculate union beta
219    CALL UN(ptseqn(), houtspann(), AMPHIOUTBETAN(), nien, UNNBETA())
220    CALL NORMAL(UNNBETA(), nlen, unnbetan())
221
222    GOSUB producto
223    PRINT 5
224    RETURN
225    'GOTO SALIDA
226
227    MOMENTAGLE:
228    PRINT "ENTER ANGLE FOR ALPHA STRUCTURES "
229    INPUT angalpha
230    PRINT "ENTER ANGLE FOR BETA STRUCTURES "
231    INPUT angbeta
232      RETURN
233
234    ALPHAWINDOW:
235    PRINT " ENTER WINDOW SIZE FOR MEMBRANE HELICAL SPANS (ODD NUMBER)"
236    INPUT WHEL
237      RETURN
238
239    BETAWINDOW:
240    PRINT "ENTER WINDOW SIZE FOR UNION SPAN (ODD NUMBER)"
241    INPUT span
242      RETURN
243
244    UNNWINDOW:
245      PRINT "ENTER WINDOW SIZE FOR SMOOTHING UNION"
246    INPUT UW
247      RETURN
248
249    MAIN:        'window size j is already defined
250    IF j > 1 THEN
```

FIG.10e

```
251 '************ STARTING SEGMENT
252   FOR m = 1 TO (j - 1) / 2
253     LB =1              'LOW BOUNDARY
254     UB = m + (j - 1) / 2'upper BOUNDARY
255     GOSUB CALCULATION
256   NEXT m
257 '******* END SEGMENT
258   FOR m= (nlen + 1 - (j-1)/2 TO nlen 'm ctr of window*/
259     LB = m - (j - 1) / 2"Low BOUNDARY
260     UB + nlen
261     GOSUB CALCULATION
262   NEXT m
263 ' MAIN CENTER SEGMENT
264   FOR m = (j + 1) / 2 TO (nlen - (j-1)/2)' m center of the window*/
265     LB = m - (j - 1) / 2
266     UB = m + (j - 1) / 2
267     GOSUB CALCULATION
268   NEXT m
269 END IF
270   RETURN
271
272 CALCULATION:
273 IF FLAG = 1 THEN ' calculate hydrophobicity*/
274     cumh = : cum = 0          ' reset hydrophobicity accumulator */
275   FOR I = LB TO UB            ' Loop on i through all res. in window */
276     cumh = seqh(I) + cumh
277     cum = cum + 1
278     hout(m) = cumh / cum      ' compute hydrophobicity average *
279   NEXT I
280 ELSE                          'hydrophobic moment*/
281   t = 0
282   acum = 0
283   Mx = 0!
284   My = 0!           'reset amphi accumulators*/
285     FOR I = LB TO UB          'Loop on i through all res. in window */
286   x = COS(2 * 3.1416 * ANGLE * (I - LB) / 360)'Esinberg
287   y = SIN(2 * 3.1416 * ANGLE * (I - LB) / 360)
288   Mx = Mx + (x * seqh(I))
289   My = My + (y * seqh(I))
290
291   acum = acum + 1
292       NEXT I
293   amphiout(m) = SQR(Mx ^ 2 + My ^ 2)
294 END IF
295   RETURN
296 '       sub SMOOTH(dum(1),nlen,duma(1))
297 '       FOR  m=1 TO nlen                  'J window size for smoothing*
298 '       if 0<m< ((j-1)/2+1) then
299 '       LB=1            'Low boundary
300 '       UB=m+(j-1)/2    'upper boundary
```

FIG.10f

```
301  '     end if
302  '         NEXT m
303  '     FOR nlen= +1-(j-1)/2) TO nlen ' m center of tthe window*/
304  '     LB-nlen-(J-1)/2   'Low boundary
305  '     UB= nlen
306  '     GOSUB SMTH
307  '
308  '     FOR  m=(j+1)/2 TO (nlen-(j-1)/2) ' m center of the window*/
309  '     LB=m-(j-1)/2
310  '     UB=m+(j-1)/2
311  '     GOSUB smth
312  '     NEXT m
313  '     return
314  SMTH:
315      SEQACCUM = 0: ACCUM = 0'RESET
316   FOR I = LB TO UB
317     SEQACCUM = SEQACCUM + DUM(I)
318     ACCUM = ACCUM +1
319   NEXT I
320     DUMS(m) = SEQACCUM / ACCUM
321     RETURN
322  producto:
323  OPEN fileout$ FOR OUTPUT AS #2
324  'PRINT #2, "res", "H21", "H7", "ma", "mb", "pt", "ua", "ub"
325  PRINT #2, "res", "H21", "H7", "pt", "ua", "ub"
326    FOR L = 1 TO nlen
327    PRINT "L= "; ;L; "; nlen= "; lien
328    p1 = round(houtspann(L), 2)
329  ' p2=round(amphioutailphan(L)2,)
330  ' p3=round(amphioutbetan(L),2)
331    p4 = round(ptseqn(L), 2)
332    p5 = round(wnnalphan(L), 2)
333    p6 = round(wnnbetan(L), 2)
334    p7 = round(houtmheln(L), 2)
335  LOCATE 15, 1
336  'PRINT L;p7;p1;p2;p3;p4;p5;p6
337  PRINT L; p7; p1; p4; p5; p6
338  'print #2, "res#","H"WHEL, "H"span, "ma" "mb" "<pt>" "ua", "ub"
339  'print #2, L,      p7,    p1,    p2,   p3   p4,   p5    p6
340  PRINT #2, L, p7, p1, p4, p5, p6
341    NEXT L 'and do next row
342  CLOSE #2
343  RETURN
344  solide:
345  PRINT " ### DONE ####"
346
347        SUB NORMAL (DUM(), nlen, DUMM())
348
349   seqmax = DUM(1): seqmin = DUM(1): SEQCUM = DUM(1)' reset max and min average accumulators*/
350  FOR I = 2 TO nlen'MAX AND MIN DETERMINATION '*/
```

FIG.10g

```
351     IF seqmax < DUM(1) THEN seqmax = DUM(I)
352     IF seqmin > DUM(1 THEN seqmin = DUM(I)
353     SEQCUM = SEQCUM + DUM(I)
354        NEXT I
355     SEQAVG = SEQCUM / nlen ' average
356        FOR I = 1 TO nlen
357     DUMM(I) = -4.5 + 9 * (DUM(I) - seqmin) / (seqmax - seqmin)
358           NEXT I
359  END SUB
360
361   SUB UM (pseqn(), HOUTH(), AMPHIOUH(), nlen, UNN())
362
363  FOR m = 1 TO nlen
364  UNN(m) = HOUTM(m) + AMPHIOUTN(m) - ptsegn(m)
365  NEXT m
366  END SUB
```

FIG.10h

```
'/* PROGRAM UNION (for Union, and Chou-Fasman-Prevelige)
'/* J. FISCHBARG, F. CZEGLEDY, P. ISEROVICH, J. LI; COPYRIGHT 1994 */
'/* COLUMBIA UNIVERSITY, NEW YORK
'/* TO   CALCULATE AVG. HYDROPHOBICITY, AMPHIPHILICITY AND TURN POTENTIAL
'/* OUTPUT COLUMNS FOR SYMPHONY OR ORIGIN
'/* please do no use word "UNION" in program (PB3 has command UNION)
'       TAKES INPUT FROM DEFAULT TEXT FILE, NAMELY:
' DEFAULT$ = path$ + "union.INI"
'    TAKES SEQUENCE DATA FROM:
'       fileinp$ = path$ + filein$ + ".sqt"
' TAKES STRUCTURE INFORMATION FROM SAME SQT INPUT FILE:
' either from crystallog. or from preds., e.g., from PHD robot prediction
' WRITES OUTPUT DATA TO:
' fileou$ = path$ + "\"+ fileou$ + ".dat"
' Columnar output generated is:
'1) res: residue number
'2) aa: amino acid code
'3) H21: Kyte-Doolitle hydrophobicity, span selected for large windows
'(usually 21), assigned to center residue
'4) H7:  Kyte-Doolittle hydrophobicity, span selected for small windows
'(usually 7), assigned o center residue
'5) ua: Union for alpha strycture, small window span (same as in H7)
'6) ub: Union for beta, etc.
'7) Pa: Chou-Fasman avg. alpha propensity for tetrapeptide (i, i+1, i+2, i+3)
'8) am: marker for supratheshold CF alpha (4.5 value for ease of plotting)
'9) Pb: CF avg.  beta propens. f tetrap.
'10) bm: marker for suprath. CF beta (4.5)
'11) pt: Chou-Fasman position-dependent tetrapeptide turn propensity
'(ass. o second residue)
'12) tm: marker for suprathreshold CF turn propensity (4.5)
'13) prda: alpha prediction marker (3.5 value)
'14) prdb: beta pred.  marker (3.5)
'15) prdt: turn pred. marker (3.5).

'The Last three Lines merely represent the conversion of the information in
'the second line of the input file.
'/////////////////////////////////////////////////////////////////////
$string 2
$static
cls 'DECLARE SUB NORMAL (DUM!(), nlen%, DUMN!())
'DECLARE SUB UN (ptseq!(), HOUT!(), AMPHIOUT!(), nlen%, UNN!())
'cls
```

FIG.11a

```
common path$,filein$,fileinp$,nseq,houtsh(1),ptseq(1),ualpha(1),_
ubeta(1),hout(1)
DEFINT I-N
print "ENTER MAXIMUM SEQUENCE LENGTH TO DIMENSION ALL ARRAYS BY"
print "(preferably <2000; if more, might be limited by memory)"
PRINT " Default = carriage return = 1999"
input nseq
if nseq=0 then nseq=1999
naa = 20       'unless dealing with extraterrestrials...
'NSEQ = 300   'maximum number of amino acids in sequence; sets array sizes
'    program sensitive to this in the Power Basic environment
'   however, if compiled, so far no Limit encountered for the executable
DIM symbols$(naa)
DIM seqh(NSEQ)
DIM seqn(NSEQ)
DIM seq$(NSEQ)
DIM vkyte(naa)
DIM pturn)naa)
DIM hout(NSEQ)
DIM houtsh(NSEQ)
DIM amphi(nseq)
DIM amphiout(NSEQ)
DIM amphibeta(NSEQ)
DIM amphialpha(NSEQ)
DIM UALPHA(NSEQ)
DIM U(nseq)
DIM ubeta(NSEQ)
DIM DUM(NSEQ)
DIM DUMN(NSEQ)
DIM pai(naa)            'alpha propens, for individual amino acids
DIM pas(nseq)           'sequential indiv. alpha propens. along chain
DIM patetr(nseq)
DIM pam$(nseq)
DIM pbi(naa)            'beta propens. for individual amino acids
DIM pbs(nseq)           'sequential indiv. beta propens. along chain
DIM pbtetr(nseq)
DIM pbm$(nseq)
DIM pt(naa,4)
DIM PTSEQ(NSEQ)
DIM ptm$(nseq)
DIM phda$(nseq)
DIM phdb$(nseq)
DIM phdt$(nseq)
DIM temp$(nseq)
DIM apos$(nseq)
```

FIG.11b

```
DIM aneg$(nseq)
DIM aro$(nseq)

comienzo:
aacodes$ = "ARNDCQEGHILKMFPSTWYV"
alphacut = 100
betacut = 100
turncut = 0.75e-4
CLS
drive$ = "c:"
path$ = "\union"
DEFAULT$ = drive$ + path$ + "\" + "union.INI"
OPEN DEFAULT$ FOR INPUT AS #5
INPUT #5, drive$,path$,filename$,filename$,angalpha,angbeta,WHEL,span
CLOSE #5
fileinp$ = drive$ + path$ + "\" + filename$ + ".sqt"
fileout$ = drive$ + path$ + "\" + filename$ + ".dat"
'*********************************************************************
'Kyte-Doolittle scale
'     1,  2,   3,   4,  5,   6,   7,   8,   9,  10
'     A,  R,   N,   D,  C,   Q,   E,   G,   H,  I
 DATA 1.8,-4.5,-3.5,-3.5,2.5,-3.5-3.5,-0.4,-3.2,4.5
'    11  12,  13, 14 15, 16 17 18, 19, 20
'     L,  K,   M,  F,  P,  S,  T,  W,  Y,  V
 DATA 3.8,-3.9,1.9,2.8,-1.6,-0.8,-0.7,-0.9,-1.3,4.2
'*********************************************************************
'CHOU-FASMAN 64-protein database
'*********************************************************************
DATA A, 139, 79, 0.060, 0.076, 0.035, 0.058
DATA R, 100, 94, 0.070, 0.106, 0.099, 0.085
DATA N,  78, 66, 0.161, 0.083, 0.191, 0.091
DATA D, 106, 66, 0.147, 0.110, 0.179, 0.081
DATA C,  95,107, 0.149, 0.053, 0.117, 0.128
DATA Q, 112,100, 0.074, 0.098, 0.037, 0.098
DATA E, 144, 51, 0.056, 0.060, 0.077, 0.064
DATA G,  64, 87, 0.102, 0.085, 0.190, 0.152
DATA H, 112, 83, 0.140, 0.047, 0.093, 0.054
DATA I,  99,157, 0.043, 0.034, 0.013, 0.056
DATA L, 130,117, 0.061, 0.025, 0.036, 0.070
DATA K, 121, 73, 0.055, 0.115, 0.072, 0.095
DATA M, 132,101, 0.068, 0.082, 0.014, 0.055
DATA F, 111,123, 0.059, 0.041, 0.065, 0.065
DATA P,  55, 62, 0.102, 0.301, 0.034, 0.068
DATA S,  72, 94, 0.120, 0.039, 0.125, 0.106
DATA T,  78,133, 0.086, 0.108, 0.065, 0.079
```

FIG.11c

```
DATA W, 103,124, 0.077, 0.013, 0.064, 0.167
DATA Y,  73 131, 0.082, 0.065, 0.114, 0.125
DATA V,  97,164, 0.062, 0.048, 0.028, 0.053

' ////////////////////////////////////////////////////////////
CLS
'print "Free memory: ";fre(0); fre(-1); fre(-2)

PRINT "UNION ALGORITHM; J. Fischbarg, F. Czegledy, P. Iserovich. Copyright 1994"
print" Set for sequence Length up to  "nseq
print "
START:
DUMMY = 0
PRINT " ENTER ONE OF THE FOLLOWING "
PRINT
PRINT "1. CHANGE FILE NAME FOR INPUT; currently: "; fileinp$
'PRINT "2. CHANGE FILE NAME FOR OUTPUT; currently: ";fileout$
PRINT "2. CHANGE ANGLE FOR ALPHA/BETA STRUCTURES (HYDROPHOBIC MOMENT) "
PRINT "  ALPHA STRUCTURE = "; angalpha; "BETA STRUCTURE= "; angbeta
PRINT "3. CHANGE A.A. SPAN FOR MEMBRANE HELICES; currently: "; WHEL
PRINT "4. CHANGE A.A. FOR UNION; currently: "; span
PRINT "5. CHANGE PATH; CURRENTLY: " path$
print "6. CHANGE DRIVE; CURRENTLY: drive$
'PRINT "6. CHANGE WINDOW SIZE FOR SMOOTHING UNION; currently: "; UW
PRINT "9. TO END SESSION WITHOUT RUNNING"
PRINT "0. (DEF=CR) MAIN - RUN WITH CURRENT PARAMETERS- RUNS ONLY ONCE AND EXITS
print
PRINT " "
 INPUT DUMMY
 SELECT CASE DUMMY
  CASE 1 :  GOSUB FILENAMEINPUT
 ' CASE 2 :  GOSUB FILENAMEOUTPUT
  CASE 2 :  GOSUB MOMENTANGLE
  CASE 3 :  GOSUB ALPHAWINDOW
  CASE 4 :  GOSUB BETAWINDOW
  CASE 5 :  GOSUB NEWPATH
   'TO COMIENZO   'road under repairs-monkeying with discouraged
 ' CASE 6  : GOSUB UNNWINDOW
  CASE 9  : GOTO salida
  CASE 0  : GOTO correte
 END SELECT
 GOTO start

' ////////////////////////////////////////////////////////////
```

FIG.11d

```
producto:
c$ = " , "
OPEN fileout$ FOR OUTPUT AS #2
PRINT #2, "res" c$ "aa" c$ "H21" c$ "H7" c$ "ua" c$ "ub" c$ "Pa" c$_
"am" c$ "Pb" c$ "bm" c$ "pt" c$ "tm" c$ "prda" c$ "prdb" c$ "prdt" c$_
"pos" c$ "neg" c$ "aro" c$
FOR 1 = 1 TO nlen
Locate 16,1
PRINT "1= "; 1; "; nlen= "; nlen
    hlng = round(hout(1), 2)
    hsh = round(houtsh(1), 2)
    ua = round(ualpha(1), 2)
    ub = round(ubeta(1), 2)
    pa = round(patetr(1), 2)
    pb = round(pbtetr(1), 2)
    pt = round(ptseq(1), 2)
PRINT #2,1 c$ seq$(1) c$ hlng c$ hsh c$ ua c$ ub c$ pa c$ pam$(1)_
    c$ pb c$ pbm$(1) c$ pt c$ ptm$(1) c$ phda$(1) c$ phdb$(1) c$ phdt$(1)
NEXT 1                                                                    'and do next row
CLOSE #2
erase hout,houtsh,ualpha,ubeta,petetr,pbtetr,ptseq
return '/////////////////////////////////////////////////////////////////////
newpath:
print "Enter new path, e.g., C:\PROT\PRD\(note no end \ or end space)"
input test$
if test$*"" then goto newpath
path$ = test$
DEFAULT$ = drive$ + path$ + "\" + "union.INI"
fileinp$ = drive$ + path$ + "\" + filename$ + ".sqt"
fileout$ = drive$ + path$ + "\" + filename$ + ".dat"
return
'/////////////////////////////////////////////////////////////////////
correte:   'main routine - records parameters and runs
    cls
    OPEN DEFAULT$ FOR OUTPUT AS #6
    WRITE #6,drive$,path$,filename$,filename$,angalpha,angbeta,WHEL,span
    CLOSE #6
    GOSUB WORKING
PRINT
print "COMPLETED RUN SUCCESSFULLY - STOPPING NOW"
STOP  'With all the erase statements to save memory, cannot run again
    'all key arrays erased by now
```

FIG.11e

```
'GOTO start
'////////////////////////////////////////////////////////////////////

FILENAMEINPUT:
cls
chdrive drive$
chdir path$
files "*.SQT"
files "*.DAT"
LOCATE 20, 1
PRINT "ENTER FNAME (ONLY) FOR INPUT SEQ; PROG ADDS DEF FILE TYPES .SQT & .DAT"
INPUT filename$
fileinp$ = drive$ + path$ + "\" + filename$ + ".sqt"
fileout$ = drive$ + path$ + "\" + filename$ + ".dat"
RETURN MOMENTANGLE:
PRINT "ENTER ANGLE FOR ALPHA STRUCTURES"
INPUT angalpha
PRINT "ENTER ANGLE FOR BETA STRUCTURES"
INPUT angbeta
 RETURN ALPHAWINDOW:
PRINT "ENTER WINDOW SIZE FOR MEMBRANE HELICAL SPANS (ODD NUMBER)"
INPUT WHEL
 RETURN BETAWINDOW:
PRINT "ENTER WINDOW SIZE FOR UNION SPAN (ODD NUMBER)"
INPUT span
 RETURN

UNNWINDOW:
 PRINT "ENTER WINDOW SIZE FOR SMOOTHING UNION"
 INPUT UW
 RETURN

' ////////////////////////////////////////////////////////////////////

WORKING:
 print fre(0); fre(-1); fre(-2)
 OPEN filenp$ FOR INPUT AS #1
 INPUT #1, sequence$
 input #1, structure$
```

FIG.11f

```
CLOSE #1
FOR n = 1 TO 20
    READ vkyte(n)
    symbols$(n) = MID$(aacodes$, n, 1)
NEXT n
FOR i = 1 TO 20
READ symbols$(i),pai(i),pbi(i),pt(I,1),pt(i,2),pt(i,3),pt(i,4)
NEXT i
RESTORE
             '//////// **************    /////////////////////
PRINT "  ............ WORKING ................."
cfspan = 4                  'prepare for Chou-Fasman-Prevelige tetrapeptides
nlen = LEN(sequence$)
FOR n = 1 TO nlen
seq$(n) = MID$(sequence$, n, 1)    'list of aa codes
NEXT n
FOR I = 1 TO nlen       'from 1 to length of sequence */
    FOR k = 1 TO 20
    IF seq$(I) = symbols$(k) THEN  ' iedentify ordinal FOR aa */
            seqh(I) = vkyte(k) ' assign hydrophobicity value to residue*/
            seqn(I) = k         'assign residue name number*/
        pas(i) = pai(k)        'assign alpha propensity
        pbs(i) = pbi(k) 'assign beta propensity
        exit for           'done here; leave for/next loop
        END IF
            NEXT k
NEXT I FOR n = 2 TO (nlen - 2)
PTSEQ(n)=pt(seqn(n-1),1)*pt(seqn(n),2)*pt(seqn(n+1),3)*pt(seqn(n+2),4)
NEXT n
 erase seqn
PTSEQ(1) = PTSEQ(2)
PTSEQ(nlen) = PTSEQ(nlen -2)
PTSEQ(nlen -1) = PTSEQ(nlen - 2)
for i=1 to nlen
if ptseq(i)>=turncut then
    for ind = 0 to 3
        ptm$(i + ind) = "4.5" : next ind : goto cortada
end if
if ptseq(i)<turncut then
        if ptm$(i)= "4.5 " then goto cortada
        else
            ptm$(i)="  "
end if
```

FIG.11g

```
CLOSE #1
FORn = 1 TO 20
    READ vkyte(n)
    symbols$(n) = MID$(aacodes$, n, 1)
NEXT n
FOR i = 1 TO 20
READ symbols$(i),pai(i),pbi(i),pt(I,1),pt(i,2),pt(i,3),pt(i,4)
NEXT i
RESTORE
              '//////  *************      ///////////////////
PRINT "  ............ WORKING ................."
cfspan = 4              'prepare for Chou-Fasman-Prevelige tetrapeptides
nlen = LEN(sequence$)
FOR n = 1 TO nlen
seq$(n) = MID$(sequence$, n, 1)   'list of aa codes
NEXT n
FOR I = 1 TO nlen    'from 1 to length of sequence */
    FOR k = 1 TO 20
    IF seq$(I) = symbols$(k) THEN ' iedentify ordinal FOR aa */
            seqh(I) = vkyte(k) ' assign hydrophobicity value to residue*/
            seqn(I) = k              'assign residue name number*/
        pas(i) = pai(k)       'assign alpha propensity
        pbs(i) = pbi(k)  'assign beta propensity
        exit for              'done here; leave for/next loop
       END IF
          NEXT k
NEXT I FOR n = 2 TO (nlen - 2)
PTSEQ(n)=pt(seqn(n-1),1)*pt(seqn(n),2)*pt(seqn(n+1),3)*pt(seqn(n+2),4)
NEXT n
 erase seqn
PTSEQ(1) = PTSEQ(2)
PTSEQ(nlen) = PTSEQ(nlen -2)
PTSEQ(nlen -1) = PTSEQ(nlen - 2)
for i=1 to nlen
if ptseq(i)>=turncut then
    for ind = 0 to 3
        ptm$(i + ind) = "4.5" : next ind : goto cortada
end if
if ptseq(i)<turncut then
        if ptm$(i)= "4.5 " then goto cortada
        else
                ptm$(i)="   "
end if
```

FIG.11h

```
' calculation alpha moment*/

FLAG = 0  'selects amphiout output
j=span
ANGLE = angalpha
GOSUB MAIN        'gets amphiout(m)*/
CALL NORMAL(amphiout(), nlen, amphialpha())'gets amphialpha*/

'       ***********//////////////***************

' calculation beta moment*/

FLAG = 0  'selects amphiout output
j=span
ANGLE=angbeta
GOSUB MAIN      'gets amphiout(m)*/
CALL NORMAL(amphiout(), nlen, amphibeta()) 'gets amphibeta
 erase amphiout
'       ***********//////////////***************

'calculate union alpha
CALL UN(ptseq(), houtsh(), amphialpha(), nlen, ualpha())
 erase amphialpha
CALL NORMAL(ualpha(), nlen, ualpha())
'calculate union beta
CALL UN(ptseq(), houtsg(), amphibeta(), nlen, ubeta())
 erase amphibeta
CALL NORMAL(ubeta(), nlen, ubeta())
 erase amphi
 erase seqh
'       ***********//////////////***************
'       /////////////////////////////////////////////////////////
'       PROCESS STRUCTURE STRING (PREDICTIONS OF CRYSTALLOG.)
alfam$ = "3.5 " : betam$ = "3.5 " : turnm$ = "3.5 "
posm$ = "2.5 " : negm$ = "2.0 " : arom$ = "5.5 "
FOR n = 1 TO nlen
temp$(n) = MID$(strucure$, n, 1)  'list of structure codes
NEXT n
for i=1 to nlen
if temp$(i) = "H" then
        phda$(i) = alfam$ : phdb$(i) = "  " : phdt&(i) = "  "
end if
if temp$(i) = "E" then
        phda$(i) = "  " : phdb$(i) = betam$ : phdt$(i) = "  "
end if
if temp$(i) = "C" then
```

FIG.11i

```
            phda$(i) = " " : phdb$(i) = " " : phdt$(i) = " "
end if
if temp$(i) = "T" then
       phda$(i) = " " : phdb$(i) " " : phdt$(i) = turnm$
end if
if seq$(i) = "F" or seq$(i)="Y" or seq$(i)="W" then
        aro$(i) = arom$
   else
    aro$(i) = " "
end if
if seq$(i) = "E" or seq$(i)= "D" then
       aneg$(i) = negm$
   else
    aneg$(i) = " "
end if
if seq$(i) = "R" or seq$(i)= "K" then
       apos$(i) = posm$
   else
    apos$(i) = " "
end if next i
close #4
erase temp$
GOsub producto
return

' ///////////////////////////////////////////////////////////////////

MAIN:   'window size j is already defined
IF j > 1 THEN
'************** STARTING SEGMENT
     FOR m = 1 TO (j - 1) / 2    '1 to 10
     LB = 1    'LOW BOUNDARY
     UB = m + (j - 1) / 2 'upper BOUNDARY m+10
     GOSUB CALCULATION
     NEXT m
' ********MAIN CENTER SEGMANT   '11 to nlen - 10
     FOR m = (j + 1) / 2 TO (nlen - (j - 1) / 2)' m center of the window*/
     LB = m - (j - 1) / 2   'm-10
     UB = m + (j - 1) / 2   ' m+10
     GOSUB CALCULATION
     NEXT m
'******* END SEGMENT       'nlen-9 to nlen
FOR m = (1 + nlen - (j - 1) / 2 TO nlen 'm ctr of window*/
```

FIG.11j

```
    LB = m - (j - 1) / 2   'low BOUNDARY m-10
    UB = nlen
    GOSUB CALCULATION
   NEXT m
END IF
 RETURN

' ///////////////////////////////////////////////////////////////

CALCULATION:

IF FLAG = 1 THEN        ' calculate hydrophobicity of std. tm. segmts. */
  cumh = 0: cum = 0     ' reset hydrophobicity accumulators */

FOR I = LB TO UB      'loop on i through all res. in window */
   cumh = seqh(I) + cumh
   cum = cum + 1
   hout(m) = cumh / cum  ' compute hydrophobicity average *
  NEXT I ELSEIF FLAG = 2 THEN ' calculate hydrophobicity of short tm. segments.*/
  cumh = 0: cum = 0   ' reset hydrophobicity accumulators*/

FOR I = LB TO UB    'loop on i through all res. in window*/
   cumh = seqh(I) + cumh
   cum = cum + 1
   houtsh(m) = cumh / cum   ' compute hydrophobicity average*
  NEXT I ELSEIF FLAG = 0 THEN       ' calc. hydrophobic moment*/ t = 0 : acum = 0 : Mx = 0! : My = 0!   'reset amphi accumulators*/
  FOR I = LB TO UB         'loop on i through all res. in window */
   x = COS(2 * 3.1416 * ANGLE * (I - LB) / 360)    'Einsberg
   y = SIN(2 * 3.1416 * ANGLE * (I - LB) / 360)
   Mx = Mx + (x * seqh(i))
   My = My + (y * seqh(i))
   acum = acum + 1
  NEXT I
  amphiout(m) = SQR(Mx^2 + My^2)

END IF

RETURN
```

FIG.11k

```
'      //////////////*************************//////////////
PRINT " ### DONE ####"
salida:

stop
end
'  /////////////////////////////////////////////////////////////////
          SUB NORMAL (DUM(), nlen, DUMN())

ytop#=DUM(1):ybot#=DUM(1):yCUM#=DUM(1)' RESET MAX, MIN & AVG ACCUMULATORS*/
     FOR I = 2 TO nlen 'MAX AND MIN DETERMINATION '*/
         IF DUM(I)>ytop# THEN
         ytop# = DUM(I)
         yhord = i
         end if
           IF DUM(I) < ybot# THEN
         ybot# = DUM(I)
         ylord=i
         end if
'         yCUM#=yCUM# + DUM(I)
'    NEXT 1
'         yAVeraG=yCUM# / nlen 'average
     FOR I = 1 TO nlen
'print DUM(I)
'print (DUMN(I) - ybot#);(ytop# - ybot#);(DUM(1) - ybot#)/ (ytop# - ybot#)
         DUMN(I) = -4.5 + 9 * (DUM(1) - ybot#) / (ytop# - ybot#)
         NEXT I

,END SUB
'////////////////////////////////////////////////////////////////////

SUB UN (ptseq(), HOUTsh(), AMPHI(), nlen, U())

FOR m = 1 TO nlen
     U(m) = HOUTsh(m) + AMPHI(m) - ptseq(m)

NEXT m***********************************************
   END SUB
     SUB NORMALPA (DUM(), nlen, DUMN())
```

FIG.11I

```
deltalfa# = 75
llalfa# = 64
    FOR I = 1 TO NLEN
        DUMN(I) = -4.5 + 9 * (DUM(I) - llalfa#) / (deltalfa#)
    NEXT I END SUB
***********************************************************
    SUB NORMALPB (DUM(), nlen, DUMN())

deltabeta# = 106
llbeta# = 51
    FOR I = 1 TO NLEN
        DUMN(I) = -4.5 + 9 * (DUM(I)-llbeta#) / (deltabeta#)
    NEXT I

END SUB
```

FIG.11m

```
1
2    '/* PROGRAM UCFP (for Union, and Chou-Fasman-Prevelige)
3    '/* J. FISCHBARG, F. CSEGLEDY, P. ISEROVICH; COPYRIGHT 1994 */
4    '/* COLUMBIA UNIVERSITY, NEW YORK
5    '/* TO CALCULATE AVG. HYDROPHOBICITY, AMPHIPHILICITY AND TURN POTENTIAL
6    '/* OUTPUT COLUMNS FOR SYMPHONY OR ORIGIN
7    '/* please do no use word "UNION" in program (PB3 has command UNION)
8    ' TAKES INPUT FROM DEFAULT TEXT FILE, NAMELY:
9    '    DEFAULT$ * path$ + "UCFP.INI"
10   '    TAKES SEQUENCE DATA FROM:
11   ' fileinp$ = path$ + filein$ + ".sqt"
12   ' TAKES STRUCTURE INFORMATION FROM SAME SQT INPUT FILE:
13   ' either from crystallog. or from preds., e.g., from PHD robot prediction
14   ' WRITES OUTPUT DATA TO:
15   ' fileout$ = path$ + "\"+ fileou$ + ".dat"
16   ' Columnar output generated is:
17   '1) res: residue number
18   '2) aa: amino acid code
19   '3) H21: Kyte-Doolittle hydrophobicity, span selected for large windows
20   '(usually 21), assigned to center residue
21   '4) H7:  Kyte-Doolittle hydrophobicity, span selected for small windows
22   '(usually 7), assigned to center residue
23   '5) ua: Union for alpha structures, small window span (same as in H7)
24   '6) ub: Union for beta, etc.
25   '7) Pa: Chou-Fasman avg. alpha propensity for tetrapeptide (i, i+1, i+2, i+3)
26   '8) am: marker for supratheshold CF alpha (4.5 value for ease of plotting)
27   '9) Pb: CF avg> beta propens. f tetrap.
28   '10) bm: marker for suprath. CF beta (4.5)
29   '11) pt: Chou-Fasman position-dependent tetrapeptide turn propensity
30   '(ass. to second residue)
31   '12) tm: marker for suprathreshold CF turn propensity (4.5)
32   '13) prda: alpha prediction marker (3.5 value)
33   '14) prdb: beta pred. marker (3.5)
34   '15) prdt: turn pred. marker (3.5).
35
36   'The Last three Lines merely represent the conversion of the information in
37   'the second line of the input file.
38   ' ///////////////////////////////////////////////////////////////////////
39   $string 2
40   $static
41   cls
42
43   'DECLARE SUB NORMAL (DUM!(), nlen%, DUMN!())
44   'DECLARE SUB UN (ptseq!(), HOUT!(), AMPHIOUT!(), nlen%, UNN!())
45   'cls
46   common path$,filein$,fileinp$,nseq,houtsh(1),ptseq(1),ualpha(1),_
47   ubeta(1),hout(1)
48   DEFINT I-N
49   print "ENTER MAXIMUM SEQUENCE LENGTH TO DIMENSION ALL ARRAYS BY"
50   PRINT "(preferably <2000; if more, might be Limited by memory)"
```

FIG.12a

```
51  PRINT " Default = carriage return = 1999"
52  input nseq
53  if nseq=0 then nseq=1999
54  naa = 20        'unless dealing with extraterrestrials...
55  'NSEQ = 300   ' maximum number of amino acids in sequence; sets array sizes
56  ' program sensitive to this in the Power Basic environment
57  '  however, if compiled, so far no Limit encountered for the executable
58  DIM symbols$(naa)
59  DIM seqh(NSEQ)
60  DIM seqn(NSEQ)
61  DIM seq$(NSEQ)
62  DIM vkyte(naa)
63  DIM pturn(naa)
64  DIM hout(NSEQ)
65  DIM houtsh(NSEQ)
66  DIM amphi(nseq)
67  DIM amphiout(NSEQ)
68  DIM amphibeta(NSEQ)
69  DIM amphialpha(NSEQ)
70  DIM UALPHA(NSEQ)
71  DIM U(nseq)
72  DIM ubeta(NSEQ)
73  DIM DUM(NSEQ)
74  DIM DUMM(NSEQ)
75  DIM pai(naa)              'alpha propens. for individual amino acids
76  DIM pas(nseq)             'sequential indiv. alpha propens. along chain
77  DIM patetr(nseq)
78  DIM pam$(nseq)
79  DIM pbi(naa)              'beta propens. for individual amino acids
80  DIM pbs(nseq)             'sequential indiv. both propens. along chain
81  DIM pbtetr(nseq)
82  DIM pbm$(nseq)
83  DIM pt(naa,4)
84  DIM PTSEQ(NSEQ)
85  DIM pm$(nseq)
86  DIM phda$(nseq)
87  DIM phdb$(nseq)
88  DIM phdt$(nseq)
89  DIM temp$(nseq)
90  comienzo:
91  aacodes$ = "ARNDCQEGHILKMFPSTWYV"
92  alphacut = 100
93  betacut = 100
94  turncut = 0.75e-4
95  CLS
96  drive$ = "c:"
97  path$ = "\UCFP"
98  DEFAULT$ = drive$ + path$ + "\" + "UCFP.INI"
99  OPEN DEFAULT$ FOR INPUT AS #5
100 INPUT #5, DRIVE$,path$,filename$,filename$,angalpha,angbeta,WHEL,span
```

FIG.12b

```
101   CLOSE #5
102   fileinp$ = drive$ + path$ + "\" + filename$ + ".sqt"
103   fileout$ = drives$ + path$ + "\" + filename$ + ".dat"
104   '*********************************************************************
105   'Kyte-Doolittle scale
106   '     1,  2,  3,  4,  5,  6,  7,  8,  9, 10
107   '     A,  R,  N,  D,  C,  Q,  E,  G,  H,  I
108    DATA 1.8,-4.5,-3.5,-3.5,2.5,-3.5-3.5,-0.4,-3.2,4.5
109   '     11  12,  13, 14 15, 16 17 18, 19, 20
110   '     L,  K,  M,  F,  P,  S,  T,  W,  Y,  V
111    DATA 3.8,-3.9,1.9,2.8,-1.6,-0.8,-0.7,-0.9,-1.3,4.2
112   '*********************************************************************
113   'CHOU-FASMAN 64-protein database
114   '*********************************************************************
115   DATA A, 139, 79, 0.060, 0.076, 0.035, 0.058
116   DATA R, 100, 94, 0.070, 0.106, 0.099, 0.085
117   DATA N,  78, 66, 0.161, 0.083, 0.191, 0.091
118   DATA D, 106, 66, 0.147, 0.110, 0.179, 0.081
119   DATA C,  95,107, 0.149, 0.053, 0.117, 0.128
120   DATA Q, 112,100, 0.074, 0.098, 0.037, 0.098
121   DATA E, 144, 51, 0.056, 0.060, 0.077, 0.064
122   DATA G,  64, 87, 0.102, 0.085, 0.190, 0.152
123   DATA H, 112, 83, 0.140, 0.047, 0.093, 0.054
124   DATA I,  99,157, 0.043, 0.034, 0.013, 0.056
125   DATA L, 130,117, 0.061, 0.025, 0.036, 0.070
126   DATA K, 121, 73, 0.055, 0.115, 0.072, 0.095
127   DATA M, 132,101, 0.068, 0.082, 0.014, 0.055
128   DATA F, 111,123, 0.059, 0.041, 0.065, 0.065
129   DATA P,  55, 62, 0.102, 0.301, 0.034, 0.068
130   DATA S,  72, 94, 0.120, 0.039, 0.125, 0.106
131   DATA T,  78,133, 0.086, 0.108, 0.065, 0.079
132   DATA W, 103,124, 0.077, 0.013, 0.064, 0.167
133   DATA Y,  73 131, 0.082, 0.065, 0.114, 0.125
134   DATA V,  97,164, 0.062, 0.048, 0.028, 0.053
135
136   ' /////////////////////////////////////////////////////////
137   CLS
138   'print "Free memory: ";fre(0); fre(-1); fre(-2)
139
140   PRINT "UCFP ALGORITHM; J. Fischborg, F. Czegledy, P. Iserovich. Copyright 1994"
141   print" Set for sequence Length up o  "nseq
142   print "
143   START:
144   DUMMY = 0
145   PRINT " ENTER ONE OF THE FOLLOWING "
146   PRINT
147   PRINT "1. CHANGE FILE NAME FOR INPUT; currently: "; fileinp$
148   'PRINT "2. CHANGE FILE NAME FOR OUTPUT; currently: ";fileout$
149   PRINT "2. CHANGE ANGLE FOR ALPHA/BETA STRUCTURES (HYDROPHOBIC MOMENT) "
150   PRINT "  ALPHA STRUCTURE = "; angalpha; "BETA STRUCTURE= "; angbeta
```

FIG.12c

```
151  PRINT "3. CHANGE A.A. SPAN FOR MEMBRANE HELICES; currently: "; WHEL
152  PRINT "4. CHANGE A.A. FOR UNION; currently: "; span
153  PRINT "5. CHANGE PATH; CURRENTLY: " path$
154  print "6. CHANGE DRIVE; CURRENTLY: drive$
155  'PRINT "6. CHANGE WINDOW SIZE FOR SMOOTHING UNION; currently: "; UW
156  PRINT "9. TO END SESSION WITHOUT RUNNING"
157  PRINT "0. (DEF=CR) MAIN - RUN WITH CURRENT PARAMETERS- RUNS ONLY ONCE AND EXITS
158  print
159  PRINT " "
160    INPUT DUMMY
161    SELECT CASE DUMMY
162    CASE 1 :   GOSUB FILENAMEINPUT
163  ' CASE 2 :   GOSUB FILENAMEOUTPUT
164    CASE 2 :   GOSUB MOMENTANGLE
165    CASE 3 :   GOSUB ALPHAWINDOW
166    CASE 4 :   GOSUB BETAWINDOW
167    CASE 5 :   GOSUB NEWPATH
168    'TO COMIENZO   'road under repairs-monkeying with discouraged
169  ' CASE 6  : GOSUB UNNWINDOW
170    CASE 9  : GOTO salida
171    CASE 0  : GOTO correte
172  END SELECT
173  GOTO start
174
175  '///////////////////////////////////////////////////////////////////////////
176  newpath:
177  print "Enter new path, e.g., C:\PROT\PRD\(note no end \ or end space)"
178  input test$
179  if test$*"" then goto newpath
180  path$ = test$
181  DEFAULT$ = drive$ + path$ + "\" + "UCFP.INI"
182  fileinp$ = drive$ + path$ + "\" + filename$ + ".sqt"
183  fileout$ = drive$ + path$ + "\" + filename$ + ".dat"
184  return
185  '///////////////////////////////////////////////////////////////////////////
186  correte:  'main routine - records parameters and runs
187    cls
188    OPEN DEFAULT FOR OUTPUT AS #6
189    WRITE #6,drive$,path$,filename$,filename$,angalpha,angbetaWHEL,span
190    CLOSE #6
191    GOSUB WORKING
192  PRINT
193  print "COMPLETED RUN SUCCESSFULLY - STOPPING NOW"
194  STOP  'With all the erase statements to save memory, cannot run again
195    'all key arrays erased by now
196  'GOTO start
197  '///////////////////////////////////////////////////////////////////////////
198
199  FILENAMEINPUT:
200  cls
```

FIG.12d

```
201 'print "string space remain." fre(0)
202 'print "bytes Left in mem. f. data"  fre(-1)
203 'print "stack space never used " fre(-2)
204 'input dummy
205 chdrive drive$
206 chdir path$
207 files  "*.SQT"
208 rem SHELL "DIR " + path$ + "*.SEQ/W"
209 LOCATE 20, 1
210 PRINT "ENTER FNAME (ONLY) FOR INPUT SEQ; PROG ADDS DEF FILE TYPES .SQT & .DAT"
211 INPUT filename$
212 fileinp$ = drive$ + path$ + "\" + filename$ + ".sqt"
213 fileout$ = drive$ + path$ + "\" + filename$ + ".dat"
214  RETURN
215
216 MOMENTANGLE:
217 PRINT "ENTER ANGLE FOR ALPHA STRUCTURES "
218 INPUT angalpha
219 PRINT "ENTER ANGLE FOR BETA STRUCTURES "
220 INPUT angbeta
221    RETURN
222
223 ALPHAWINDOW:
224 PRINT "ENTER WINDOW SIZE FOR MEMBRANE HELICAL SPANS (ODD NUMBER)"
225 INPUT WHEL
226    RETURN
227
228 BETAWINDOW:
229 PRINT "ENTER WINDOW SIZE FOR UNION SPAN (ODD NUMBER)"
230 INPUT span
231    RETURN
232
233 UNNWINDOW:
234   PRINT "ENTER WINDOW SIZE FOR SMOOTHING UNION"
235 INPUT UW
236    RETURN
237
238 '////////////////////////////////////////////////////////////////////////
239
240 WORKING:
241   print fre(0); fre(-1); fre(-2)
242   OPEN fileinp$ FOR INPUT AS #1
243   INPUT #1 sequences$
244   input #1, structures
245   CLOSE #1
246   FOR n = 1 TO 20
247     READ vkyte(n)
248     symbols$(n) = MID$(aacodes$, n, 1)
249   NEXT n
250   FOR i = 1 TO 20
```

FIG.12e

```
251     READ symbols$(i)pai(i),pbi(i)pt(I,1),pt(i,2),pt(i,3),pt(i,4)
252     NEXT i
253     RESTORE
254             '/////// ************** /////////////////////
255     PRINT " ............ WORKING ................"
256     cfspan = 4      'prepare for Chou-Fasman-Prevelige tetrapeptides
257     nlen = LEN(sequence$)
258     FOR n = 1 TO nlen
259     seq(n) = MID$(sequence$, n, 1)   'List of aa codes
260     NEXT n
261     FOR I = 1 TO nlen      ' from 1 TO Length of sequence */
262       FOR k = 1 TO 20
263       IF seq$(I) = symbols$(k) THEN, ' identify ordinal FOR aa */
264         seqh(I) = vkyte(k)    ' assign hydrphobicity value to residue*/
265         seqn(I) = k           'assign  residue name number*/
266            pas(i) = pai(k)    'assign alpha propensity
267            pbs(i) = pbi(k)    'assign beta propensity
268            exit for           'done here: Leave for/next Loop
269       END IF
270          NEXT k
271     NEXT I
272
273     FOR n = 2 TO (nlen - 2)
274     PTSEQ(n)=pt(seqn(n-1),1)*pt(seqn(n),2)*pt(seqn(n+1),,3)*pt(seqn(n+2),4)
275     NEXT n
276      erase seqn
277     PTSEQ(1) - PTSEQ(2)
278     PTSEQ(nlen) = PTSEQ(nlen - 2)
279     PTSEQ(nlen - 1) = PTSEQ(nlen - 2)
280     for i=1 to nlen
281     if ptseq(i) >* turncut then
282        for ind = 0 to 3
283        ptm$(i + ind) = "4.5 " : next ind : goto cortada
284     end if
285     if ptseq(i) < urncut then
286       if ptm$(i) = "4.5 " then goto cortada
287       else
288        ptm$(i) = " "
289     end if
290     cortada:
291     next i
292     CALL NORMAL(PTSEQ(), nlen ptseq())
293
294     ' *********** ///////////////// ***************
295
296       ' HYDROPHOBICITY CALCULATION FOR MEMBRANE HELICES * /
297     FLAG = 1 ' calculate hydrophobicity* /
298     j = WHEL            ' window
299     GOSUB MAIN         ' and we will get hout(m)
300     CALL NORMAL(hout() nlen, hout())  ' and we will get hout long*/
```

FIG.12f

```
301
302 ' ********** //////////////// ***************
303
304    ' HYDROPHOBICITY CALCULATION FOR SHORT SPAN
305 FLAG = 2 ' calculate hydrophobicity*/
306 j = span           ' window
307 GOSUB MAIN         ' and we will get houtsh(m)
308 CALL NORMAL(houtsh() nlen, houtsh()) ' and we will get hout short*/
309 ' ********** //////////////// ***************
310 ' CALCUALTION OF TETRAPEPTIDE PROPENSITIES
311 j = cfspan
312 for i=1 to nlen-3
313   patetr(i) = ( pas(i) + pas(i+1) + pas(i+2) pas(i+3) )/cfspan
314   pbtetr(i) = ( pbs(i) + pbs(i+1) + pbs(i+2) pbs(i+3) )/cfspan
315 if patetr(i) >= alphacut then
316   pam$(i) = "4.5 "
317 else
318   pam$(i) = "    "
319 end if
320 if pbtetr(i) >= betacut then
321   pbm$(i) = "4.5 "
322 else
323   pbm$(i) = "    "
324 end if
325 next i
326   erase pas, pbs
327   for j= 2 TO 0 step -1     ' approximate bottom ends
328 patetr(nlen-j) = patetr(nlen-3)
329 pbtetr(nlen-j) = pbtetr(nlen-3)
330 next j
331
332 CALL NORMALPA(patetr(), nlen, patetr() )
333 CALL NORMALPB(pbtetr(), nlen, pbtetr() )
334
335        ' calculation alpha moment*/
336
337 FLAG = 0  ' selects amphiout output
338 j = span
339 ANGLE = angalpha
340 GOSUB MAIN              'gets amphiout(m)*/
341 CALL NORMAL(amphiout(), nlen, amphialpha())'gets amphialpha*/
342
343 ' ********** //////////////// ***************
344 ' calculation beta moment*/
345
346 FLAG = 0 'selects amphiout output
347 j = span
348 ANGLE = angbeta
349 GOSUB MAIN      'gets amphiout(m)*/
350 CALL NORMAL(amphiout()< nlen< amphibeta())  'gets amphibeta
```

FIG.12g

```
351   erase amphiout
352   '*********** /////////////// ***************
353
354   'calculate union alpha
355   CALL UN(ptseq()< housh(), amphialpha(), nlen, ualpha())
356     erase amphialpha
357   CALL NORMAL(ualpha(), nlen, ualpha())
358   'calculate union beta
359   CALL UN(ptseq(), housh(), amphibeta(), nlen, ubeta())
360     erase amphibeta
361   CALL NORMAL(ubeta(), nlen, ubeta())
362   erase amphi
363   erase seqh
364   '*********** /////////////// ***************
365   '////////////////////////////////////////////////////////////////
366   'PROCESS STRUCTURE STRING (PREDICTIONS OR CRYSTALLOG.)
367   alfam$ = "3.5 "
368   betam$ = "3.5 "
369   turnm$ = "3.5 "
370   FOR n = 1 TO nlen
371   temp$(n) = MID$(structure$, n, 1)   'List of structure codes
372   NEXT n
373   for i=1 to nlen
374   if temp$(i) = "H" then
375     phda$(i) = alfam$ : phdb$(i) = " " : phdt$(i) = " "
376   end if
377   if temp$(i) = "E" then
378     phda$(i) = " " : phdb$(i) = betam$ : phdt$(i) = " "
379   end if
380   if temp$(i) = "C" then
381     phda$(i) = " " : phdb$(i) = " ": phdt$(i) = " "
382   end if
383   if temp$(i) = "T" then
384     phda$(i) = " " : phdb$(i) = " " : phdt$(i) turnm$
385   end if
386   next i
387   close #4
388   erase temp$
389   GOsub producto
390   return
391
392   '////////////////////////////////////////////////////////////////
393
394   MAIN:    'window size j is already defined
395   IF j > 1 THEN
396   '************** STARTING SEGMENT
397     FOR m = 1 TO (j - 1) / 2    '1 TO 10
398     LB = 1          'LOW BOUNDARY
399     UB = m + (j - 1) / 2'upper BOUNDARY  m+10
400     GOSUB CALCULATION
```

FIG.12h

```
401   NEXT m
402 ' ********MAIN CENTER SEGMENT     '11 TO nlen - 10
403   FOR m = (j + 1) / 2 TO (nlen - (j - 1) / 2)' m center of the window*/
404   LB = m - (j - 1) / 2   ' m-10
405   UB = m + (j - 1) / 2   ' m+10
406   GOSUB CALCULATION
407   NEXT m
408 '******* END SEGMENT  'nlen-9 to nlen
409   FOR m = (1 + nlen - (j - 1) / 2) TO nlen 'm ctr of window*/
410   LB = m - (j - 1) / 2 'Low BOUNDARY  m-10
411   UB = nlen
412   GOSUB CALCULATION
413   NEX m
414 END IF
415   RETURN
416
417 ' ////////////////////////////////////////////////////////////////////////
418
419 CALCULATION:
420
421 IF FLAG = 1 THEN    ' calculate hydrophobicity of std. tm. segms.*/
422 cumh = 0: cum = 0       ' reset hydrophobicity accumulators*/
423
424 FOR I = LB TO UB        'Loop on i through all res. in window */
425 cumh =  seqh(I) + cumh
426 cum = cum + 1
427 hout(m) = cumh / cum         ' compute hydrophobicity average *
428 NEXT I
429
430 ELSEIF FLAG = 2 THEN   ' calculate hydrophobicity of short tm. segmts.*/
431 cumh = 0: cum = 0        ' reset hydrophobicity accumulators */
432
433 FOR I = LB TO UB        'Loop on i through all res. in window */
434 cumh + seqh(I) + cumh
435 cum = cum + 1
436 houtsh(m) = cumh / cum       ' compute hydrophobicity average *
437 NEXT I
438
439 ELSEIF FLAG = 0 THEN       ' calc. hydrophobic moment*/
440
441 t = 0 : acum = 0 : Mx = 0! : My = 0!   'reset amphi accumulators*/
442 FOR I = LB TO UB         'Loop on i through all res. in window */
443 x = COS(2 * 3.1416 * ANGLE * (I - LB) / 360) 'Eisenberg
444 y = SIN(2 * 3.1416 * ANGLE * (I - LB) / 360)
445 Mx = Mx + (x * seqh(I))
446 My = My + (y * seqh(I))
447 acum = acum + 1
448 NEXT I
449 amphiout(m) = SQR(Mx ^ 2 + My ^ 2)
450
```

FIG.12i

```
451  END IF
452
453    RETURN
454
455  ' ///////////////////////////////////////////////////////////
456
457  producto:
458  c$ = " "
459  OPEN fileout$ FOR OUTPUT AS #2
460  PRINT #2, "res" c$ "aa" c$ "H21" c$ "H7" c$ "uaa" c$ "ub" c$ "Pa" C$_
461  "am" c$ "Pb" c$ "bm" c$ "pt" c$ "m" c$ "prda" c$ "prdb" c$ "prdt"
462  FOR L = 1 TO nlen
463    Locate 16,1
464    PRINT "L= "; L; "; nlen= "; nlen
465    hlng = round(hout(L), 2)
466    hsh  = round(houtsh(L), 2)
467    ua   = round(ualpha(L), 2)
468    ub   = round(ubeta(L), 2)
469    pa   = round(patetr(L), 2)
470    pb   = round(pbtetr(L), 2)
471    pt   = round(ptseq(L), 2)
472    PRINT #2,L c$ seq$(L) c$ hlng c$ hsh c$ ua c$ ub c$ pa c$ pam$(L)_
473    c$ pb c$ pbm$(L) c$ pt c$ ptm$(L) c$ phda$(L) c$ phdb$(L) c$ phdt$(L)
474  NEXT L                'and do next row
475  CLOSE #2
476  erase hout,houtsh,ualpha,ubeta,petetr,pbtetr,ptseq
477  return
478
479  ' ///////////*************************///////////
480
481  salida:
482  PRINT " ### DONE ####"
483
484  stop
485  end
486
487
488  ' /////////////////////////////////////////////////////////////////
489
490        SUB NORMAL (DUM(), nlen, dumn())
491
492  ytop#=DUM(1):ybot#=DUM(1):ycum#=DUM(1)' reset max, min & avg accumulators*/
493    FOR I = 2 TO nlen 'MAX AND MIN DETERMINATION  '*/
494      IF DUM(I) > ytop# THEN
495              ytop# = DUM(I)
496              yhord = i
497              end if
498      IF DUM(I) < ybot# THEN
499              ybot# = DUM(I)
500              yLord=i
```

FIG.12j

```
501              end if
502  '    ycum# = ycum# + DUM(I)
503     NEXT I
504  '     yAVeraG = ycum# / nlen  ' average
505     FOR I = 1 TO nlen
506  'print DUM(I)
507  'print (DUM(I) - ybot#);(ytop# - ybot#);(DUM(I) - ybot#)/ (ytop# - ybot#)
508     DUMN(I) = -4.5 + 9 * (DUM(I) - ybot#) / (ytop# - ybot#)
509     NEXT I
510
511     END SUB
512
513  '////////////////////////////////////////////////////////////////////
514
515     SUB UN (ptseq(), HOUTsh(), AMPHI(), nlen, U())
516
517  FOR m = 1 TO nlen
518     U(m) = HOUTsh(m) + AMPHI(m) - ptseq(m)
519  NEXT m
520     END SUB
521  '****************************************************
522         SUB NORMALPA (DUM(), nlen, DUMN())
523
524  deltalfa# = 75
525  llaLfa# = 64
526     FOR I = 1 TO NLEN
527     DUMN(I) = -4.5 + 9 * (DUM(I) - llALfaa#) / (deLtalfa#)
528     NEXT I
529
530     END SUB
531  '****************************************************
532         SUB NORMALPB (DUM(), nlen, DUMN())
533
534  deltabeta# = 106
535  llbeta# = 51
536     FOR I = 1 TO NLEN
537     DUMN(I) = -4.5 + 9 * (DUM(I) - llbeta#) / (detabeta#)
538     NEXT I
539
540     END SUB
```

FIG.12k

METHOD FOR PREDICTING THE TENDENCY OF A PROTEIN TO FORM AMPHIPHILIC α OR β STRUCTURE

1. INTRODUCTION

The present invention relates to methods of predicting the tendency of a portion of a protein to form amphiphilic α or β structure.

2. BACKGROUND OF THE INVENTION

2.1. Methods for Determining Protein Structure

Several algorithms are currently used to evaluate the secondary structure of proteins, including the Kyte-Doolittle, Chou-Fasman-Prevelige, and PHD methods.

The Kyte-Doolittle method (Kyte and Doolittle, 1982, J. Mol. Biol. 157: 105–132) evaluates the hydrophobicity and hydrophilicity of each amino acid, as they appear sequentially in a protein. The program then uses a continuous moving segment approach that determines the average hydropathy within a predetermined segment. Although the program can accurately predict interior and exterior regions of soluble globular proteins, data on membrane spanning regions of transmembrane proteins is more ambiguous.

The Chou-Fasman-Prevelige (CFP) algorithm (Prevelige and Fasman, 1989, in "Predictions of Protein Structure and the Principles of Protein Conformation", Fasman, ed., Plenum Press, New York, pp. 391–416) uses a statistical approach to the study of protein secondary structure. The conformational parameters for each amino acid are calculated using the relative frequency of a given amino acid within a protein, its occurence in a given type of secondary structure, and the fraction of residues occuring in that type of structure. Since these parameters (such as hydrophobicity) contain information about protein stability, properly weighted for their relative importance, they are useful for predicting secondary structures. These parameters, represented by Pα and Pβ or Pc (for α-helix, β-sheets or coils, respectively) are utilized to locate nucleation sites within an amino acid sequence. These nucleation sites are then extended until a stretch unlikely to belong to that structure is encountered, whereupon that structure is terminated. This process is repeated throughout the sequence until the secondary structure of the entire sequence is predicted.

The PHD method (Rost and Sander, 1992, Nature 360: 540) utilizes a combination of evolutionary and multiple sequence alignment information, and a "jury" of 12 networks. Since this method is a fully automated computer program, it is independent of human input or interpretation and as such delivers a unique approach.

2.2. Structure of Glucose Transport Proteins

Mammalian glucose transporter proteins (GLUTS) constitute a family of proteins which are integrally embedded in the cell membrane and primarily transport glucose into and out of cells. Recent evidence indicates that compounds other than glucose, for example, water, dehydroascorbic acid and nicotinamide, can traverse GLUTs suggesting that these proteins may be multifunctional.

For example, glucose transporter proteins have recently been shown to exhibit a modest permeability to water (Fischbarg et al., 1990, Proc. Natl. Acad. Sci. USA, 87:3244–3247), suggesting that there is a channel in glucose transporter proteins that is hydrated and may serve as a conduit for the substrates mentioned in the paragraph above. Further, GLUT proteins may play a role in the pathogenesis of diabetes, in that insulin elicits a specific and rapid response from GLUT proteins in human muscle and fat cells where a rapid translocation of GLUT from an internal storage pool to the plasma membrane occurs, thereby increasing the glucose uptake by these cells. In adipocytes, the Km for glucose may also be lowered as a response to insulin.

The GLUT proteins have been well characterized biochemically and their primary structures have been determined. But as is the case with many membrane proteins, the secondary structures of GLUTs are largely unknown, greatly hindering any study of their molecular mechanisms.

The hitherto most favored model of GLUT secondary structure predicts that GLUT proteins form 12 transmembrane α-helices (12H model; Mueckler et al., 1985, Science, 229:941–945). Further studies suggesting a high α-helical content include Chin et al., 1986, J. Biol. Chem. 261: 7101–7104 (Fourier transform infrared spectroscopy, FTIR) and Chin et al., 1987, Proc. Natl. Acad. Sci. U.S.A. 84:4113–4116 (circular dichroiism, CD). Other studies have suggested that extensive α-helical content is accompanied by significant β-folding (FTIR spectroscopy: Alvarez et al., 1987, J. Biol. Chem. 262:2502–3509; CD: Park et al., 1992, Protein Science 1:1032–1049), but have failed to appreciate the full extent of the β-structure predicted by the present invention.

The 12H model indicates that the highly conserved sequence (Ile 386- Ala 405), in a particular GLUT protein, GLUT1, is intracellular. However, recent experiments (Fischbarg et al., 1993, Proc. Natl. Acad. Sci. U.S.A. 90: 11658–11662) utilizing a synthetic polyclonal antibody to this conserved region showed that the antibody induced an increased glucose uptake only when administered extracellularly. This is inconsistent with the purported intracellular location of the region in the 12H model. These data, contradicting the established model, prompted further analysis of GLUT secondary structure using the novel algorithm of the invention and, as set forth below, led to the discovery of a new model for GLUT structure.

3. SUMMARY OF THE INVENTION

The present invention relates to methods of predicting the tendency of a portion of a protein to form amphiphilic α or β structure. It is based, at least in part, on the discovery that porin membrane proteins, which were previously assumed to contain predominantly α amphiphilic structure, unexpectedly are predicted to contain substantial amounts of β structure.

The methods of the present invention provide a number of advantages relative to methods previously used to analyze protein structure. For example, the CFP algorithm fails to consider hydrophobicity and amphiphilicity, and is more ambiguous in its predictions than the algorithms of the present invention. The CFP peaks are not fully representative of the actual protein structure, whereas the peaks seen by the union program may provide a better visual representation of actual secondary structure.

In particular embodiments, the methods of the invention may be used to predict the presence of β-barrel structures in membrane proteins. The prediction of such structures in the protein may then be used for the rational design or identification of compounds that may interact with the protein. Alternatively, the methods of the invention may be used to create β-barrel structures in genetically engineered proteins.

4. DESCRIPTION OF THE FIGURES

FIG. 1 (D.E.H. and I) Data represent averaged values from two 10-oocyte groups: other data are averages from three such groups. Individual values differed with each other by <20%. For 60 min before the uptake assay, one group of oocyte (intracellular Ab, solid bars) was injected with 20–30 nl of a solution containing either Ab-1, Ab-4, or Ab-c (1 ng of Ab per 1 nl of water). A second group of oocytes (extracellular Ab, shaded bars) was incubated for 60 min in MBS containing the same ABs before measuring $^3$H-DOG uptake. Control oocytes (open bars) were incubated in MBS. (D) Oocytes were incubated for 60 min with Ab in the outside incubation medium; the Ab concentration was varied as indicated. Solid circles, Ab-c; open circles (controls) Ab-4. (E) Oocytes incubated with Ab-c plus the addition of various concentrations of a peptide. The following peptides were used: solid circles, the conserved peptide Ile-386-Ala-405; open circles, the last 20 amino acids at the C-terminal end of GLUT4 (F) Oocytes incubated with Abs in the outside medium. Solid circles, Ab-c; open circles, Ab-4 (G) Open circles, oocytes incubated initially in medicum containing 1 μM insulin; arrow, the medium was replaced by another one containing insulin plus Ab-c (100 μg/ml). Solid circles, Ab-c in the initial incubation medium. Ab-c plus insulin after the arrow (H and I) Lineweaver-Burk plots of $^3$H-DOG uptake in oocytes expressing GLUT1 and GLUT4, respectively, and incubated in the following media: open circles, MBS (controls); solid circles, MBS plus Ab-c (100 μg ml); triangles, MBS plus 1 μM insulin.

FIG. 2. Multiple sequence alignment of two porins (OmpF, SEQ ID NO: 1 and S16070, SEQ ID NO: 2) and GLUT1(SEQ ID NO: 3). S16070 stands for POR. Rectangles, existing (OmpF, POR) and predicted (GLUT1) β-strands. Rounded rectangles, existing (OmpF, POR) and predicted (GLUT1) α-helices.

Figure 3:
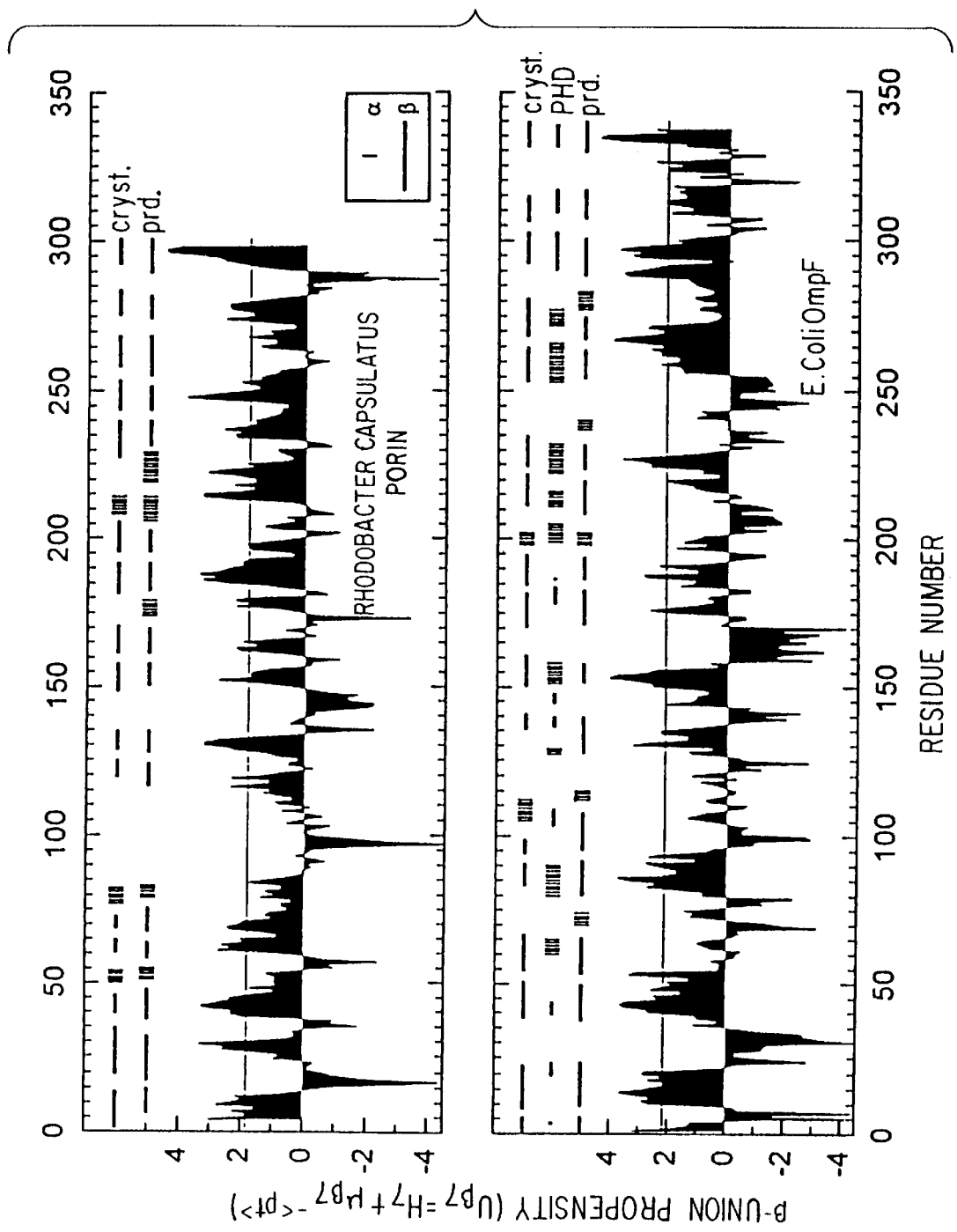

FIG. 3. Prediction of porin structures using Union. Area graphs, $U_{\beta 7}$ prediction profiles. Structures known from crystallography (cryst.) or predicted (prd) are shown above the profiles in each case.

Figure 4:
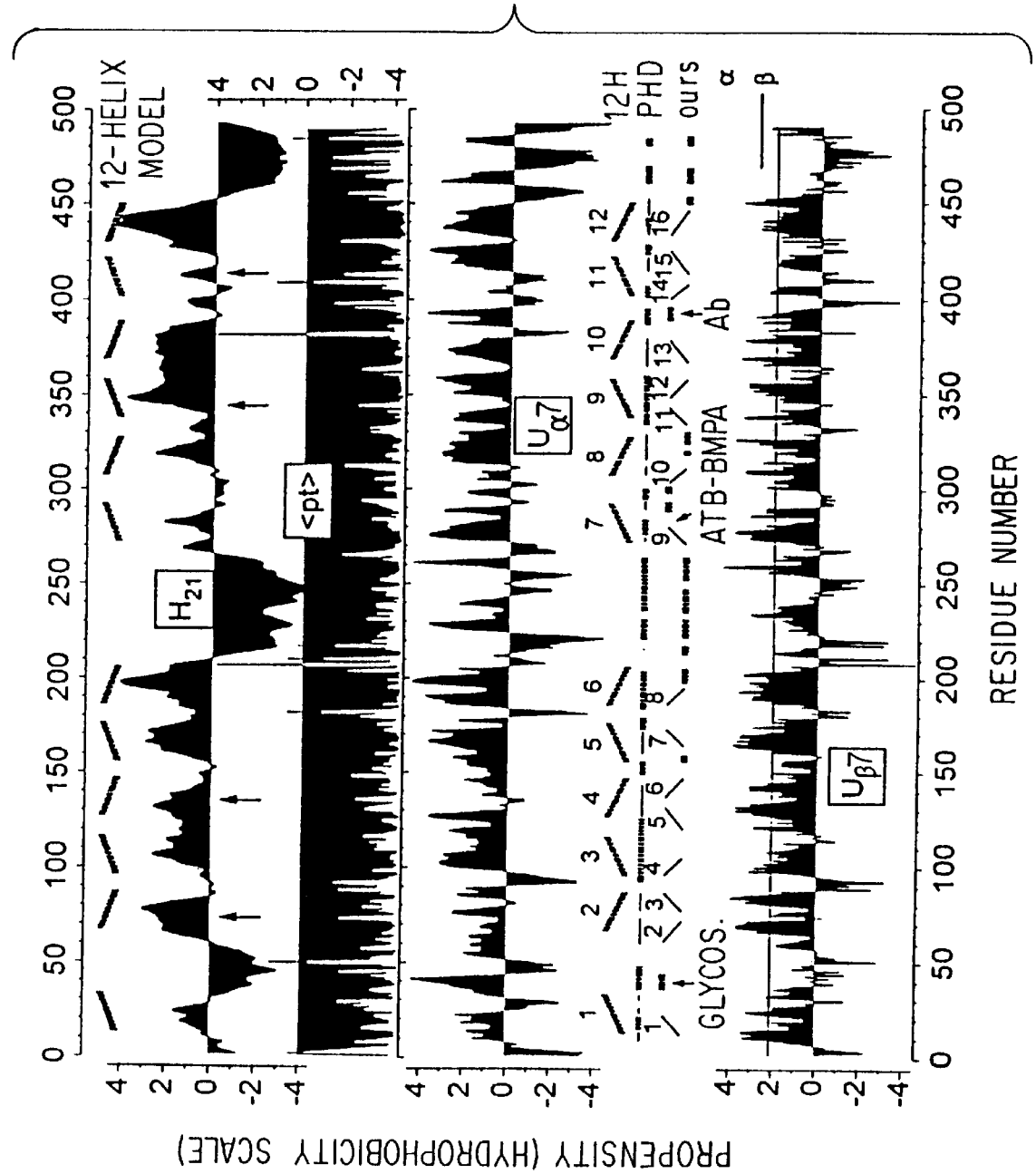

FIG. 4. Our prediction for GLUT1. From top down, prediction profiles of hydrophobicity; turn; and union propensity for amphipathic α-helices and β-strands, respectively. Spans: 4 for <pt>: others are indicated in label subindices. For comparison, predicted structures are shown at the top and bottom panels. For the 12H model and for our prediction symbols are shown angled so that their lower and higher ends correspond to their intra-and extracellular sides, respectively.

Figure 5:
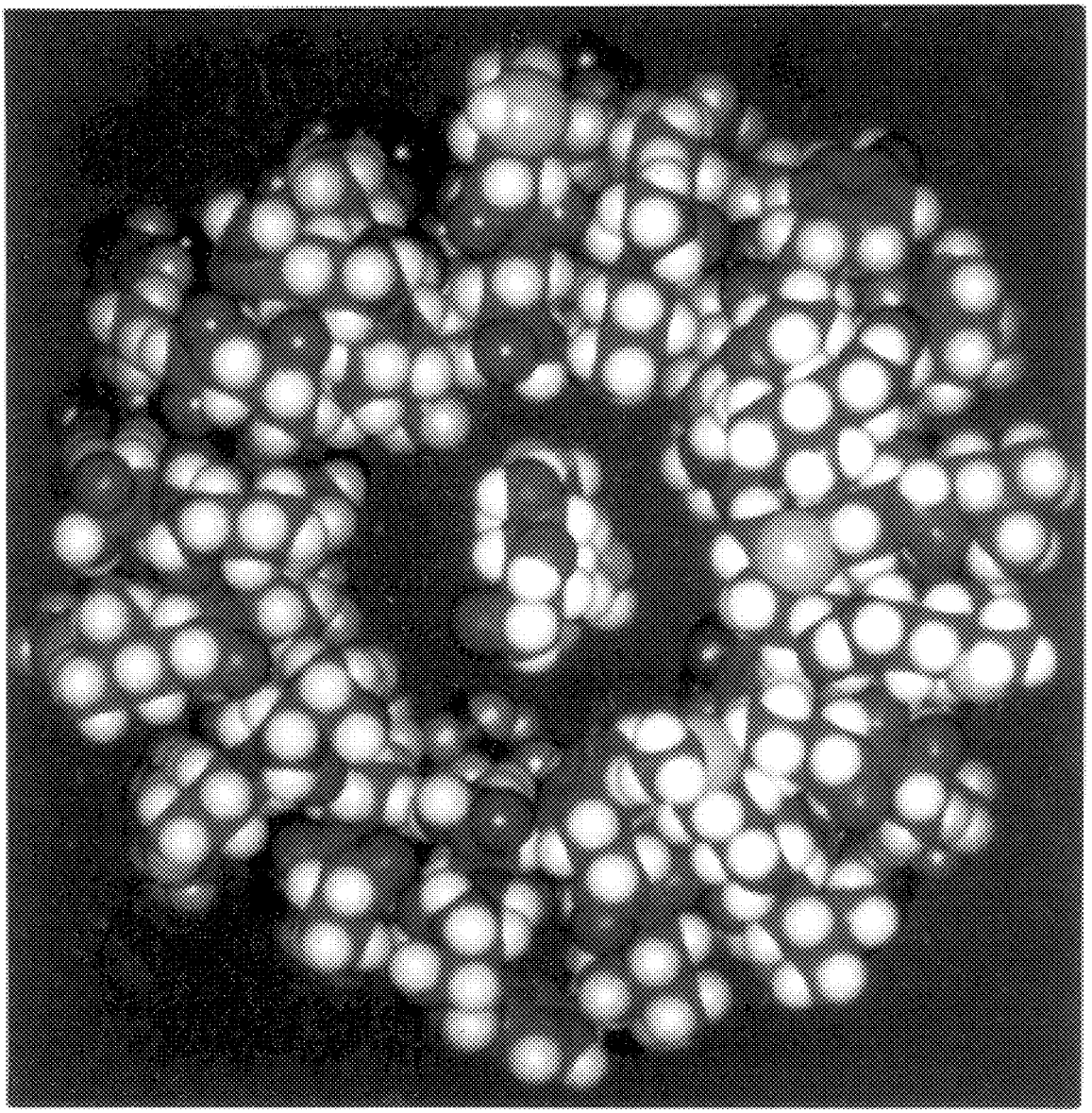

FIG. 5. Putative βB of GLUT1 viewed from inside the cell. A molecule of β-D-glucopyranose is shown in the center of the pore as a size marker (viewed from C1)

Figure 6:
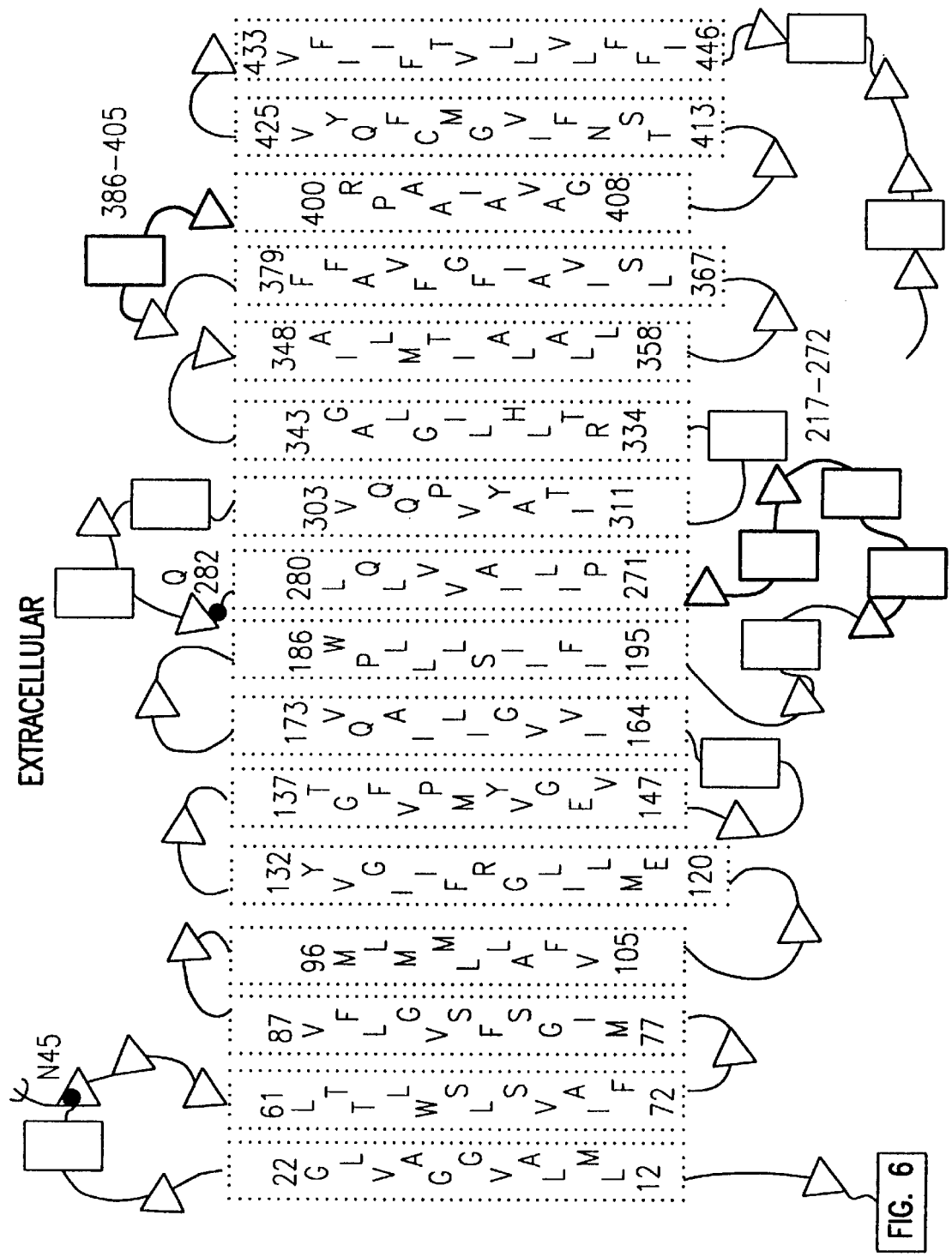

FIG. 6. Model of secondary structure of GLUT1 (SEQ ID NO: 3). Putative 16 transmembrane β-strands are represented by rectangles. The more hydrophilic sides of the β-strands (presumably lining the pore) are facing right. In the extramembrane loops, triangles denote predicted turns, and rectangles mark predicted a-helices. Of the two possible N-linked glycosylation sites N 45 and N 411, mutagenesis points to the first (Asano et al., 1991, J. Biol. Chem. 266:24632–24636). Two epitopes, 217–272 and 386–405 and a sugar binding site, Q 282 (Hashiramoto et al., 1992, J. Biol. Chem., 267: 17502–17507), are boldface.

FIGS. 7A–E. (a) reaction center, L chain; (b) bacteriorhodopsin; (c) colicin A; (d) *Rhodobacter capsulatus* porin; and (e) *Esherichia coli* porin. Union profiles are shaded. Cry: information from high-resolution structures. t: turns.

FIGS. 8A–H. (a) facilitative glucose transporter 1; (b) CH1P28; (c) acetylcholine receptor α-subunit; (d) lactose permease; (e) Na$^+$/glucose cotransporter; (f) shaker k channel; (g) calcium ATPase (sarcoplasmic reticulum; and (h) H$^+$/K$^+$ ATPase. Arrows mark predicted β-strands. In 8a, 4th panel, the dotted lines suggest the topological orientation of predicted β-strands (intracellular at bottom). In 8d, panel 1, the alkaline phosphatase activity reported for the different fusions is superimposed on the $H_{21}$ plot. Number labels identify the fusions. Also shown there is the 12H model for lac permease. As in 8a, a topological orientation is suggested (intracellular at bottom).

Figure 9A:
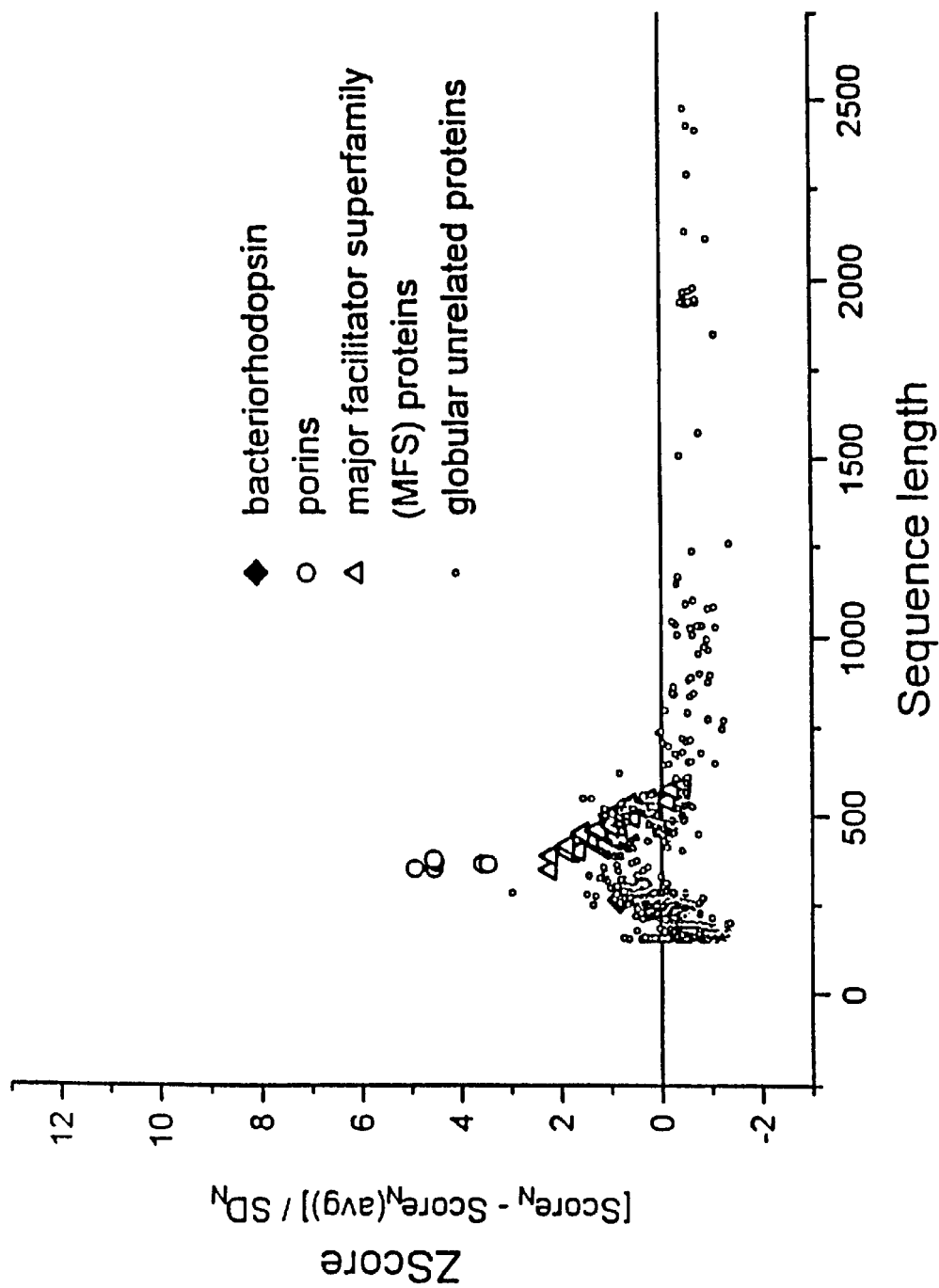

FIGS. 9A and B. Zscores have been normalized (scoreN) for sequence length as in Park et al., 1992, Protein Sci. 1:1032–1049, namely: scoreN=scoreorig/C*[1-exp (A*sequence length +B)]. For each of the two environments depicted in panels (a) and (b), the same set of 400 randomly chosen globular proteins was run to generate a baseline distribution of raw scores vs. sequence length.

FIG. 10. Source code for performing the Union algorithm.

FIG. 11. The UNION program source code.

FIG. 12. The UCFP program source code.

5. DETAILED DESCRIPTION OF THE INVENTION

For clarity of presentation, and not by way of limitation, the detailed description of the invention is divided into the following subsections:

(i) proteins to which the inventive structural determination method may be applied;

(ii) the Union algorithm;

(iii) the UNION program; and (iv) the utility of the invention.

5.1. Proteins to Which the Inventive Structural Determination Method May be Applied The methods of the present invention may be applied to any protein, in order to determine the propensity of portions of the protein to form α and β structures.

In preferred embodiments of the invention, the methods are applied to membrane proteins, particularly proteins involved in transporting compounds between the intracellular and the extracellular compartments. For example, and not by way of limitation, the methods of the present invention may be applied to the following proteins and to each member of their respective families: GLUT proteins (including but not limited to erythrocyte glycophorin), bacterial porins (including OmpC, OmpF, NmpA, NmpB, NmpC and LamB, etc.), aquaporins, bacteriorhodopsin and the bacteriorhodopsin precursor, the reaction center L chain, colicin A, *Rhodobacter capsulatus* porin, and *E. coli* porin, the acetylcholine receptor α subunit, lac permease, sodium-glucose co-transporter, shaker potassium ion channel, sarcoplasmic reticulum calcium-ATPase, components of the sodium ion/potassium ion pump, gap junction proteins, cytokine receptors, the multidrug resistance transporter, the cystic fibrosis conductance regulator and "band III" protein of the erythrocyte membrane.

5.2. The Union Algorithm

The present invention provides for a Union algorithm which is able to predict the presence of amphiphilic α and/or β structures in proteins, preferably membrane proteins, as set forth below.

The present invention provides for a method of predicting the tendency of a portion of a protein to form an amphiphilic α structure, said portion having a span of x residues, wherein x is any integer, comprising calculating a value for $U_{\alpha x}$ using the equation $U_{\alpha x}=H_x+\mu_{\alpha x}-<pt>$. $H_x$ is the average hydrophobicity for a span of x residues using the Kyte-Doolitte scale. $\mu_{\alpha x}$ is the hydrophobic moment (span x) as calculated by the method set forth in Eisenberg et al., 1984, Proc. Natl. Acad. Sci. U.S.A. 81: 140–144, for α structures, the angle between one residue and the successive residue being that associated with α helices, such as about 90–110°, and preferably 100°. <pt> is the position dependent turn propensity, as calculated according to the method set forth in Prevelige and Fasman, 1989, in "Prediction of Protein Structure and the Principles of Protein Conformation", Fasman, ed., Plenum Press, New York, pp. 391–416 (assigned to residue 2 in a 4-point turn). For example, a value of <pt> of a tetrapeptide is calculated as pt=fixfi+1× fi+2×fi+3 when "i" is the residue and f=bend frequencies in the four positions of the α-turn.

The present invention also provides for a method of predicting the tendency of a portion of a protein to form an amphiphilic β structure, said portion having a span of x residues, wherein x is any integer, comprising calculating a value for $U_{\beta x}$ using the equation $U_{\beta x}=H_x+\mu_{\beta x}-<pt>$. $H_x$ is the average hydrophobicity for a span of x residues using the Kyte-Doolitte scale. $\mu_{\beta x}$ is the hydrophobic moment (span x) as calculated by the method set forth in Eisenberg et al., 1984, Proc. Natl. Acad. Sci. U.S.A. 81: 140–144, for β structures, the angle between one residue and the successive residue being that associated with β-structures, such as about 150–210°, preferably 160°. <pt> is the position dependent turn propensity, as calculated by the method set forth in Prevelige and Fasman, 1989, in "Prediction of Protein Structure and the Principles of Protein Conformation", Fasman, ed., Plenum Press, New York, pp. 391–416 (assigned to residue 2 in a 4-point turn). For example, a value of <pt> of a tetrapeptide is calculated as pt=fixfi+1× fi+2×fi+3 when "i" is the residue and f=bend frequencies in the four positions of the β-turn.

Odd number residues are generally chosen in assigning hydropathy values so that a given sum could be plotted above the mid-residue of the segment. In preferred, nonlimiting embodiments, the value of x is seven or twenty-one. These values are preferable because a length of seven residues represents the shortest span that can be reliably used with a minimum of localized "noise". A larger span of twenty-one residues was also chosen since this represents the average length of membrane spanning α-helices.

Accordingly, the extent of α or β structure may be determined using the Union algorithm by calculating the values for U as set forth above, for a series of portions spanning the protein or a relevant part of its structure, graphically depicting the results of these calculations, and performing the following analyses:

The α or β structure of the segments are interpreted on the basis of height and width of peaks in the Uαx and Uβx profiles and the predicted hydrophobicity of the segments. The height is determined relative to a threshold. The threshold may be arbitrarily set at 0, or may be assigned a different value, depending on the protein being analyzed. For example, as in the case of the porins, (see FIG. 3) peaks were considered to originate at a threshold of zero, and were taken to predict β-structure if their upper segment exceeded a threshold set at about 2 (1.83 in one case, 2.15 in another) in an scale set to range from –4.5 to +4.5 (see Example 6, below). The value of 2 was chosen because it best fit proteins, known to have β-structure, used for calibration.

Peaks wide enough to correspond to a segment of the amino acid sequence long enough to span the membrane as an α-helix (e.g. 18–22, preferably 20 or 21 residues) are predicted to be α structures. Peaks that are too narrow to correspond to a segment of the amino acid sequence long enough to span the membrane as an α-helix but which are wide enough to correspond to a segment of the amino acid sequence with the correct length to span the membrane as β-strands (e.g., as short as 6 residues, preferably 9–14) are predicted to be β structures. Transmembrane segments of a protein may thereby be predicted to comprise either amphiphilic α -type or β -type, or both.

In preferred embodiments of the invention, the foregoing methods may be practiced employing the source code for the Union algorithm, as set forth in FIG. 10. The Uαx or the Uβx profiles generated using the source code in FIG. 10 give a graphic visualization of the Uαx or Uβx values, respectively, of the segments from one end of the protein to the other. This tracks the hydrophobic and hydrophilic regions relative to a universal midline.

For example, and not by way of limitation, the use of methods comprising the Union algorithm to identify β-barrel structure in various proteins is set forth in sections 6 and 7, below.

5.3. The Union Program

In preferred embodiments of the invention, the Union algorithm may be employed together with certain features of the Chou-Fasman-Prevelige, Kyte-Doolittle and PHD algorithms. This combination is referred to herein as the UNION program.

For example, and not by way of limitation, the following method may be performed.

(1) Values of $H_x$, $\mu_{\beta x}$ and <pt> and the obtained values of $U_{\beta x}$ may be calculated as set forth in the preceding section and their ranges scaled from –4.5 to +4.5 (see example sections 6 and 7).

(2) The Union algorithm may be used to mark the approximate location of the secondary structures. The Uαx or the Uβx profiles give a graphic visualization of the Uαx or Uβx values of the segments, respectively, relative to a universal midline.

(3) The α or β structure of the segments may be interpreted from the Uαx or Uβx profiles so that the width of the peaks from either profile may be compared to the actual distance needed to bridge a membrane. The segments, and thus the protein may be assigned an α or β structure based on the length of peaks in the Uαx and Uβx profiles and the predicted hydrophobicity of the segments.

(4) The segments may be refined using the CFP algorithm, as set forth in Prevelige and Fasman, 1989, in "Prediction of Protein Structure and the Principles of Protein Conformation", Fasman, ed., Plenum Press, New York, pp. 391–416, to calculate the values for α and β average propensities for tetrapeptides.

(5) Data from the neural network program PHD (Rost and Sander, 1992, Nature 360:540) may be added as separate profiles of the segments.

(6) The various plots obtained from the methods described in (1)–(5) may be combined in a single figure for the global picture of an individual protein. This step renders the data maximally informative and is specified by the UNION program, the source code of which is set forth in FIG. 11. The UNION program runs in the IBM DOS or Microsoft-DOS environments, using a columnar input ASCII file that includes: (1) the amino-acid sequence of the protein and (2) a corresponding sequence of literal secondary structural assignment codes for that amino acid sequence, either from the Brookhaven database for proteins with known structure, or derived from predictions for proteins of unknown secondary structure. The literal structure codes are converted into numbers and a columnar output file is generated. Figures for data analysis may be conveniently obtained by importing the UNION output into a graphics program: "ORIGIN", MicroCal Software, Northampton, Mass. 01060.

For example, and not by way of limitation, the use of the UNION program to identify β-barrel structure in various proteins is set forth in section 7, below.

5.4. The Utility of the Invention

The present invention provides for a method of predicting the structure of membrane proteins, which may be used in the following non-limiting embodiments.

In preferred embodiments, the method of the invention may be used to identify β-barrel structures in membrane proteins. The identification of β-barrel structure may be consistent with the function of the membrane protein as a translocator. As such, the present invention may be used to discern the function of membrane proteins, the function of which has been hitherto unknown.

Further, the identification of β-barrel structure in a protein may lead to the identification of molecules that can be transported by the protein. For example, the identification of a structure similar to members of the GLUT family of proteins in a particular protein would suggest that the protein may be able to translocate compounds similar to hexose compounds through a cell membrane containing that protein. Such an analysis may aid in the rational design of pharmaceutical agents that could be used to access a cell expressing the protein in its membrane.

In further embodiments, the present invention may be used to design or identify compounds able to be transported by animal or plant aquaporins (Chrispels and Agre, TIBS, 1994, : 421–425). In the case of animal aquaporins, the channel forming integral protein (CHIP), abundant in certain plasma membranes, and other homologs suggest that some of these proteins may be involved in clinical syndromes. Plant aquaporins like Tonoplast intrinsic protein (γ-TIP) can be used to study the role of these molecules in the water economy of plants, as well as to create transgenic plants that express these proteins from tissue specific promoters. Drought-resistance and hardiness in crop plants may be correlated with the presence and activity of these proteins. The present invention can be used to address the current problems present in analyzing and manipulating the molecular structure and function of this family of membrane proteins.

In still further embodiments, the present invention may be used to engineer proteins having useful β-barrel structures. For example, the ability of a number of aquaporin proteins may be compared, and the particular protein having the most favorable transport capability may be identified. The method of the present invention may then be used to analyze its structure, and the secondary structures of other membrane proteins may be manipulated to resemble the structural characteristics of the designated aquaporin.

6. EXAMPLE

Evidence That Facilitative Glucose Transporters May Fold as β-Barrels

6.1. Materials and Methods

Antibody Studies. We raised three polyclonal antibodies ("Abs") in rabbits and used the IgG fractions. They were Ab-1, against the last 21 C-terminal amino acids of the GLUT1 protein; Ab-4 against the last 25 C-terminal amino acids of the GLUT4 protein (Ab-1 specifically reacted with GLUT1 but not with GLUT2 or GLUT4, and Ab-4 reacted with GLUT4 but not with GLUT1 or GLUT2 as assessed by immunoprecipitation and immunoblotting; and Ab-c raised against a synthetic peptide containing the sequence Ile-386-Ala-405 in GLUT1, a sequence that is highly conserved in all members of the GLUT family. Ab-c reacted with the GLUT1, GLUT2 and GLUT4 isoforms of mammalian facilitative transporters as assessed by immunoprecipitation and immunoblotting and the reactivity was specifically blocked by competition with an excess of the peptide used to generate the Ab but not by an unrelated peptide. For the experiments all Abs were suspended at a final concentration of 100 μg of IgG per ml in modified (Vera et al., 1990, Mol. Cell Biol., 10:743–751) Barth's solution (MBS).

*Xenopus laevis* oocytes were isolated as described (Vera et al., 1990, Mol. Cell Biol., 10:743–751) and injected with 50 nl of water containing 10–20 ng of in vitro synthesized capped RNA (Vera, supra.) encoding either GLUT1, GLUT2, or GLUT4, and incubated in MBS. Three days after RNA injection, uptake of 2-deoxy-[1.2(n)-$^3$H]D-glucose ($^3$H-DOG) was measured using a 10-min uptake assay (Vera, supra.). Oocytes were placed into 1 ml of MBS containing 0.5 mM DOG and 1–5 μCi of $^3$H-DOG per ml (10 Ci/mmol: 1 Ci=37 GBq:NEN/DuPont). Ten pooled oocytes yielded an uptake value; values were consistent within a given batch of oocytes.

Alignments:

We used the BESTFIT and PILEUP routines of the GCG (Genetics Computer Group; Version 7.0) program package, with gap weight=3.0 and length weight=0.1 (Needleman et al., 1970, J. Mol. Biol., 48:443–453). We aligned the sequences of *Rhodobacter capsulatus* poria (SEQ ID NO: 2) (Weiss et al., 1991, FEBS Lett., 280:379–382), *Escherichia coli* porin (SEQ ID NO: 1) (Sw; Ompf-Ecoli), and GLUT1 (SEQ ID NO: 3) (Sw:Gtrl-Human).

Predictions.

We developed an algorithm ("Union") to predict protein segments with relatively high hydrophobicity and propensity to form amphiphilic α or β structures. For a residue span length i, Union (U) is: $U_{\iota,i}=H_i-\mu_{\iota,i}-(Pt)$ (Equation 1).

Depending on the structure for which U is calculated, the subindex ι stands for either α or β. $H_i$ is the average hydrophobicity for a span of i residues using the Kyte-Doolittle scale (Kyte, et al., 1982, J. Mol. Biol., 157:105–132): $\mu_{\iota,i}$ is the hydrophobic moment (Eisenberg et al., 1984, Proc. Natl. Acad. Sci. U.S.A., 81:140–144; span i) for either α or β structures: the angles between a residue and the next for α and β structures were 100° and 160°, respectively, using standard values for α-helices and the generic twist of β-sheets. $H_i$ and $\mu_{\iota,i}$ values were assigned to the center residue of given odd-valued spans. <pt> is the position-dependent turn propensity (Prevelige, and Fasman, 1989, in "Prediction of Protein Sructure and the Principles of Protein Conformation", Fasman, ed., Plenum Press, New York, pp. 391–416; assigned to residue 2 in the 4-point turn). We calculated values of $H_i$, $\mu_{\iota,i}$, and <pt> for a given sequence and scaled their ranges to −4.5 to +4.5 in each case. After algebraic addition (Eq. 1), the $U_{\iota,i}$ values obtained were in turn rescaled to −4.5 to +4.5. We used union profiles to mark the approximate locations of secondary structures. Segments were then refined by using (i) the Chou-Fasman-Prevelige prediction method (CFP), which requires judgments by the operator, and (ii) the results from a neural network prediction program [PHD: profile neural network prediction, Heidelberg; Rost and Sander 1992, Nature, 360:540)], which runs unbiased, without human intervention. We found it convenient to display propensity profiles using the program PSAAM (Crofts, A. R., 1992, Ph.D. Dissertation (University of Illinois, Unknown). Three-dimensional modeling was done in the Insight and Discover graphical environments. (Biosym Technologies, San Diego).

6.2. Results And Discussion

Effect of Abs on the Function of Mammalian Hexose Transporters Expressed in X. laevis Oocytes.

Figure 1B:
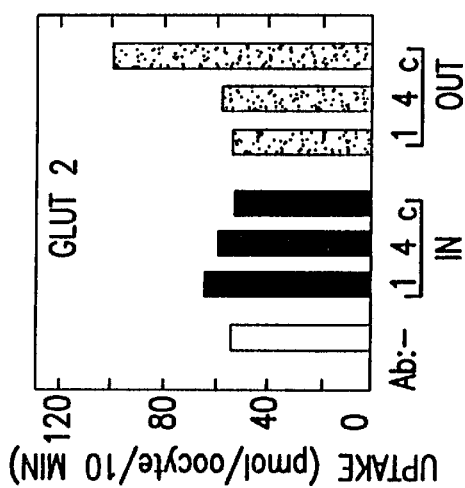
Figure 1C:
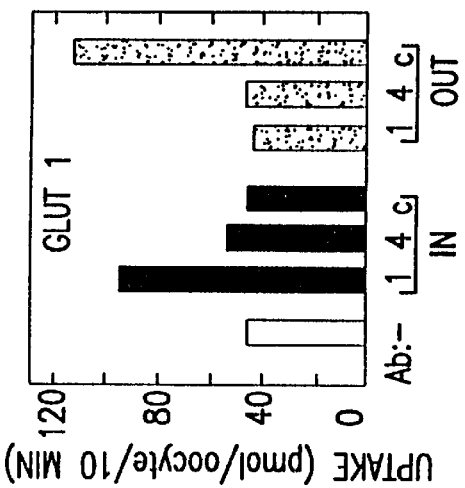
Figure 1D:
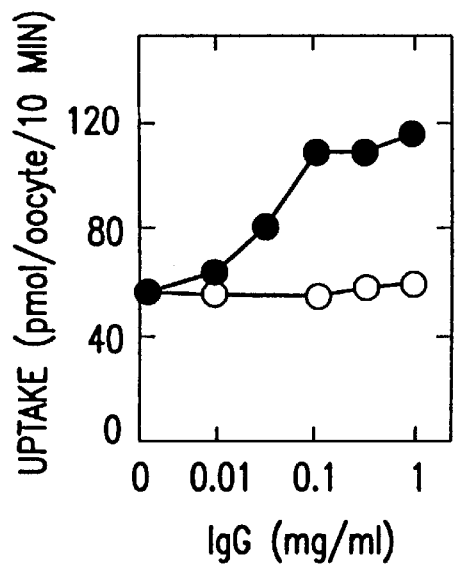
Figure 1E:
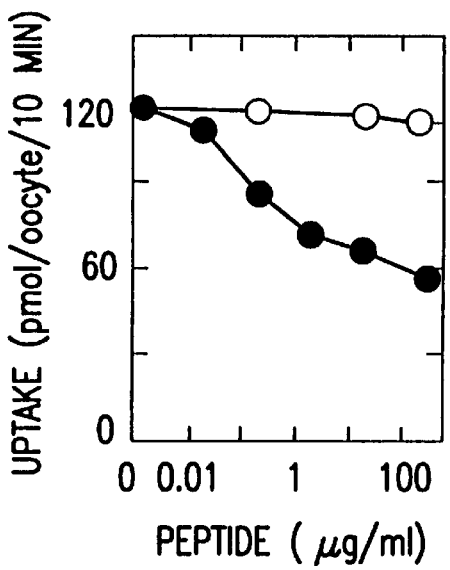
Figure 1F:
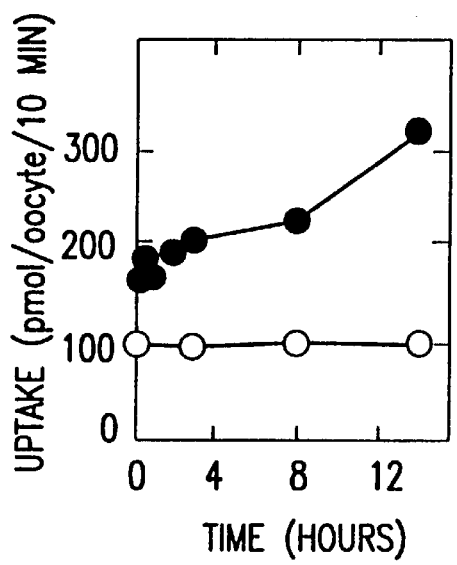

The highly conserved sequence (Ile-386Ala-405 in GLUT1) is predicted to be intracellular in the 12H model (Mueckler et al., 1985, Science, 229:941–945), which locates it between its putative tm regions 10 and 11. Given the evidence for an important functional role for the region between tm domains 4 and 12 in GLUT1 (Carruthers, 1990, Physiol. Rev., 70:1135–1175), we reasoned that an Ab against that conserved sequence might elicit inhibition or activation of the transporter. After verifying its reactivity, we used X. laevis oocytes expressing different members of the mammalian GLUT family to study the effect of this antipeptide Ab on the uptake of DOG. Incubation with Ab for 1 hour induced a measurable increase in the ability of oocytes expressing any of the three mammalian transporters tested, namely GLUT1 (FIG. 1A. c), GLUT2 (FIG. 1B. c), and GLUT 4 (FIG. 1C,c) to take up DOG. The Ab, however, acted only when present in the extracellular medium (FIGS. 1A–C, c). No effect on uptake was observed when the Ab was injected into the oocytes 1 hr before the uptake measurements (FIGS. 1A–C). The effect of Ab was dose dependent (FIG. 1D) and was specifically blocked by competition with excess peptide during the incubation period (FIG. 1E). The effect of the Ab on DOG uptake was evident after a short incubation period; near-maximal levels of activation were reached in 30 min (FIG. 1F). Incubation for several hours induced an additional increase in uptake (FIG. 1F).

To determine whether the GLUTs were expressed with the correct orientation in the membrane of the oocytes, we tested the effect of two other anti-peptide Abs we elicited against the C-terminal regions of GLUT1 and GLUT4. It was known from previous studies that this region of the transporters is located intracellularly (Oka et al., 1990, Nature, 345:550–553). As expected, the Abs did not affect the capacity of the oocytes to take up DOG when added extracellularly (FIGS. 1 A–C) but caused a specific and measurable increase in the ability of oocytes expressing GLUT1 or GLUT4 (but not GLUT2), to take up DOG when injected intracellularly (FIGS. 1 A–C). These observations are consistent with previous indicates that the C-terminal region is central to the function of the transporter (Oka, supra.).

Since both the Ab (Ab-c) and insulin (Vera, et al., 1990, Mol. Cell Biol., 10:743–751) increase DOG uptake in oocytes, we investigated whether Ab could act by mimicking insulin rather than by specifically binding to GLUTs. The results in FIGS. 1 G–I suggest instead that the Ab and insulin have different mechanisms of action. Incubation of the oocytes with insulin did not affect the $K_m$ of the transporters for DOG, increasing instead the $V_{max}$ (FIGS. 1H and I; Table 1). This is inconsistent with insulin inducing the translocation of transporters to the cell membrane. On the other hand, the Ab induced a measurable decrease in the $K_m$ for DOG in oocytes expressing either GLUT1 or GLUT4 without changing the $V_{max}$ (FIGS. 1 H and I; Table 1). The short-term effect of the Ab on uptake (FIG. 1F) can be accounted for by an increased affinity of the transporters for DOG. The additional increase in uptake observed after long incubation periods with the Ab (FIG. 1F) may be due to the entrapment of the transporters at the level of the cell membrane.

TABLE 1

Effects of insulin and Ab on $V_{max}$ and $K_m$ values

| Complementary RNA | | $V_{max} \pm$ SE. pmol per oocyte per min | $K_m \pm$ SE mM |
|---|---|---|---|
| GLUT1 (from FIG. 1H) | Control | 109 ± 23 | 8.6 ± 3.2 |
| | Antibody | 90 ± 2 | 2.8 ± 0.2 |
| | Insulin | 163 ± 22 | 6.1 ± 1.7 |
| GLUT 4 (from FIG. 1M) | Control | 76 ± 10 | 8.0 ± 1.9 |
| | Antibody | 60 ± 2 | 2.7 ± 0.2 |
| | Insulin | 119 ± 9 | 7.8 ± 1.1 |

Figure 1G:
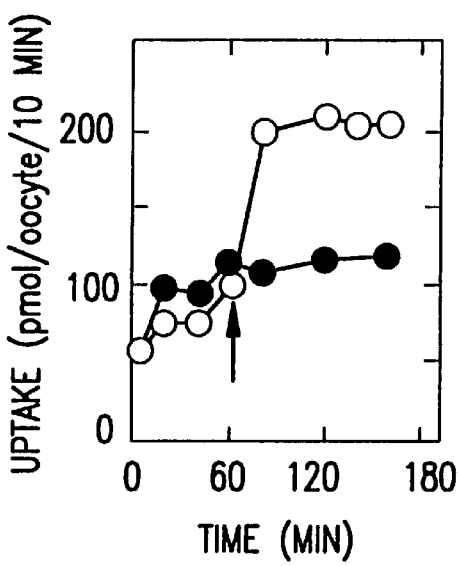
Figure 1I:
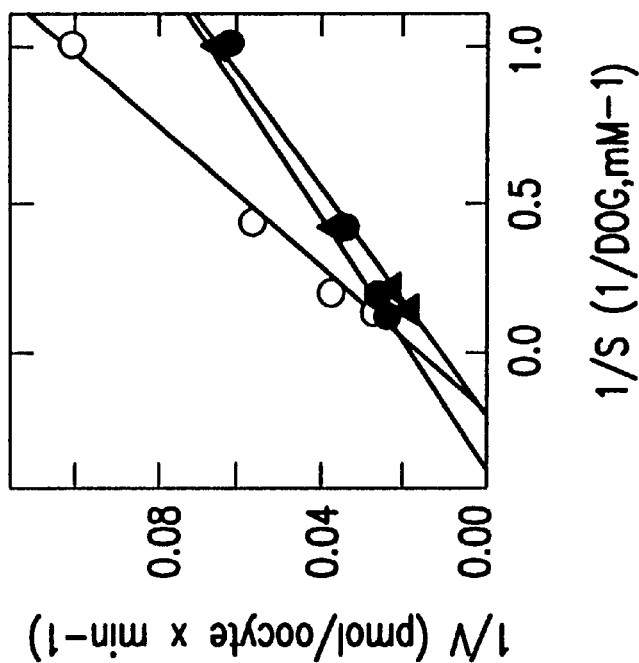
Figure 1H:
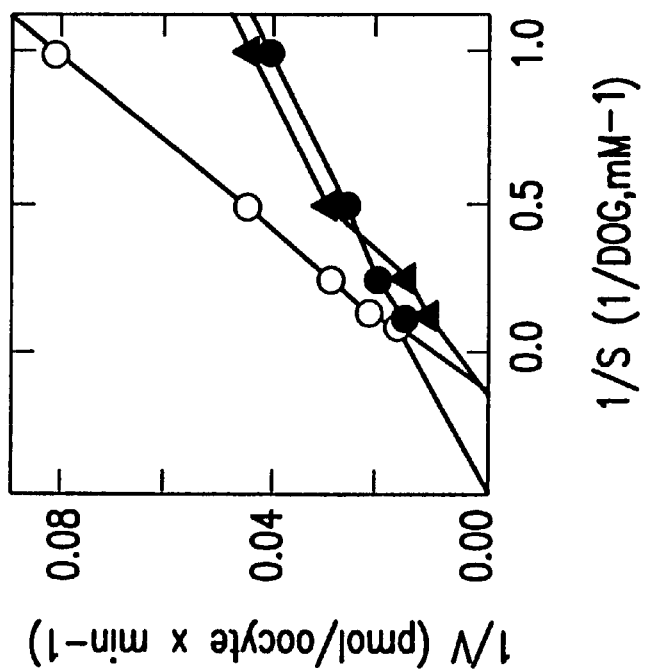

Additional evidence for the different modes of action of the Ab and insulin came from experiments in which oocytes were first treated with insulin and then with the Ab and vice versa. Under the first condition, the Ab induced a further 2-fold increase in uptake in oocytes pretreated with insulin (for a total 4-fol increase; FIG. 1G). Quantitatively, this result is consistent with the effect of the Ab on the affinity of the transporter for DOG. On the other hand, insulin did not affect the uptake of DOG in oocytes previously treated with the Ab (FIG. 1G). One explanation for this finding is that the binding of the Ab to the transporter may "anchor" it to the plasma membrane and disrupt the dynamic equilibrium that allows insulin to modify the ratio of transporters located intracellularly versus those located at the plasma membrane.

The topology induced for the Ab findings compromises 12H. A possible explanation for the effect of Ab recognition of the sequence Phe-389-Ala-403 in terms of the 12H model is to argue that perhaps tm helices 10 and 11 are in a highly mobile segment of the protein, leading to the exposure of the internal loop between them to the extracellular medium. There is an α-helical membrane protein, colicin, which appears to externalize some of its α-helices during large scale conformational changes (Parker et al., 1992, J. Mol. Biol., 224:639–657). Externalization, however, shuts off the colicin channel, while in the present case uptake by GLUTs is enhanced by the Ab-c, militating against a colicin-type mechanism. Moreover, the Ab-c had no effect when injected intracellularly, further evidence against the intracellular location of Phe-389-Ala-403. The simplest explanation for our findings is that the loop comprising the segment Phe-389-Ala-403 is normally located on the extracellular side of the membrane, suggesting a topology inconsistent with the 12H model. If GLUTs are multihelical, with tm helices ≈20 residues long, and if putative helices 11 and 12 exist, then the converged loop could only be intracellular, being separated from the intracellular C-terminal loop by the hairpin of these two helices (see FIG. 4).

An alternative scheme: GLUT1 and the Porins.

Given the foregoing, we searched for an alternative secondary structure for the transporter. We considered the structures of those few membrane proteins that have been solved by crystallography so far, and we came upon porins. In contrast to α-helical membrane proteins crystallized earlier, porin monomers form 16-stranded antiparallel βBs (Weiss et al., 1991, FEBS Lett., 280:379–382; Cowan et al., 1992, Nature, 358:727–733). When we aligned (FIG. 2) the sequences of R. capsulatus porin (POR) (SEQ ID NO: 2), E. coli porin (OmpF) (SEQ ID NO: 1), and GLUT1 (SEQ ID NO: 3) (using BESTFIT), we found pairwise scores for identity and similarity as follows: POR-OmpF 20.0 and 45.7: POR-GLUT1, 19.9 and 46.6: OmpF-GLUT1, 18.2 AND 42.9. Porins in general show little overall primary sequence similarity (Welte et al., 1991, Biochim. Biophys. Acta, 1080:271–274). In particular, although the secondary structures of POR and OmpF are the same, the scores for the alignment are modest. The alignments of GLUT1 with the porins, however, elicit about the same scores as the alignment of the two porins. Hence, we set out to evaluate a possible porin-fold for GLUT1.

Prediction of Multiple tm β-Strands in Porins. From exploratory work, we chose a span of 7 residues to examine POR, OmpF and GLUT1 profiles. We found that the union β7 ($U_{\beta 7}$) peaks identified the approximate location and length of the β-strands in both porins (FIG. 3). The thresholds in FIG. 3 (1.83 for POR: 2.15 for OmpF) were selected so as not to miss any strand; they result in only minimal overprediction. Segments were then refined by the CFP procedure. In comparing the porin structures thus predicted with those known from x-ray crystallography (Weiss et al., 1991, FEBS Lett., 280:379–382; Cowan et al., 1992, Nature, 358:727–733), we found success rates [Q3 (Qan, 1988, J. Mol. Biol., 202:865–884)] of 0.70 and 0.75 for POR and OmpF, respectively. The correlation coefficients (Mathews, 1975, Biochim. Biophys. Acta, 405:442–451) for our predictions were as follows—for POR: α 0.56; β 0.70; turns. 0.28; random. 0.48; for OmpF; α 0.25; β 0.64; turns. 0.30; random 0.44. The PHD method (available only for OmpF) predicted regions with secondary structure similar to ours Q3=0.68).

Prediction of Multiple tm β-Strands in GLUT1.

We identified 16 predicted tm β-strands in GLUT1 (FIG. 4). All were in segments that had been allocated as tm helices in the 12H model (FIG. 2). Using only $H_{21}$ profiles, several of the peaks seen (FIG. 2) appeared wide enough to be interpretable as tm α-helices with spans of 21 residues (Mueckler et al., 1985, Science, 229:941–945). However, four of them (arrows in FIG. 4) were split by predicted turns. The resulting segments were too short to bridge the membrane as α-helices but had the correct length for tm β-strands. We termed such patterns "β-hairpin signatures." Similarly, in the remaining 8 segments previously predicted as 20-residue helices (FIG. 2) we predicted tm β-strands approximately 10 residues long, with the rest of the residues sometimes forming short helices. Our predictions for the location and length of segments with secondary structure are in reasonable agreement with those from the PHD program (FIG. 2).

Given these predictions, we reexamined the alignment of the sequences of POR, OmpF, and GLUT1. We verified that segments known to have secondary structure in one or both porins aligned well with segments for which we predicted secondary structure in GLUT1 (FIG. 2). Eleven of the 16 predicted β-strands in GLUT1 overlapped partially with β-strands in porins. The paucity of gaps in these regions with conserved secondary structure is noteworthy. Some of the remaining β-strands in the porins correspond to segments predicted as helices in GLUT1 and vice versa. The alignment in FIG. 2 comprised about the last 400 residues in GLUT1; based on additional alignments, the N-terminal region of GLUT1 might have originated in partial duplication of a porin gene. In addition, there is a high degree of sequence conservation among members of the GLUT family, and hence a multi β-strand motif may be applicable to all of them.

Three-dimensional Model of the βB in GLUT1.

The predictions above suggested to us that GLUT1 might fold as the porins, forming a βB. To visualize whether such an idealized construct was compatible with GLUT function, we built a three-dimensional model of the putative GLUT1 βB, with the more hydrophilic sides of the tm β-strands facing the barrel pore. To ensure that there were no bad Van der Waals contacts, limited energy minimization was performed (300 iterations, conjugate descent algorithm. DISCOVER program). FIG. 5 shows an end-view photograph of the barrel (from inside the cell) including β-D-glucopyranose in its lumen. The Van der Waals inside diameter of the barrel, while irregular, was at least 11A which is more than enough to allow hydrated hexoses to pass through the channel.

Prior evidence consistent with a βB fold.

The 2-N-[4-(1-azi-2,2,2-trifluoroethyl)benzoyl]-1,3-bis-(D-mannos-4-yloxy)-2-propylamine (ATB-BMPA) binding site. Peptide 217–272 appears intracellular, since a specific Ab binds to it only when the cell membrane is permeabilized (Davis et al., 1990, Biochem. J., 266:799–808) This segment is very hydrophilic so that the more hydrophobic tm segment that follows it is likely to begin only at or near residue 273 (in either the 12H, PB, or PHD predictions: FIG. 2). The next marker along the chain is residue 282, which has been recently placed extracellularly, since mutation of it (Gln→Leu) decreases ATB-BMPA exofacial binding by 95% (Hashiramoto et al., 1992, J. Biol. Chem., 267:17502–17507). Hence, segment 273–281 likely spans the membrane: this segment (9 residues) is too short to be a tm α-helix (Chin, et al., 1987, J. Biol. Chem., 261:7101–7104) residues but has the correct length for a tm β-strand (strand 9, residues 271–280 (SEQ ID NO: 3 and), FIGS. 4 and 6). In the 12H model, residue 282 was placed at the center of tm α-helix 7, where it would be inaccessible to ATB-BMPA. In the βB model, residue 282 is instead in an extracellular connecting loop.

The proportions of α and β structures in GLUT based on CD and FTIR spectroscopy.

This issue is unsettled. From FTIR spectroscopic evidence, it was concluded that GLUT1 displays distinct vibrations for α-helical structure while those for β-structure are absent (Chin, supra.). This was partly challenged by a later FTIR study, which also found GLUT1 to be predominantly α-helical but in addition found evidence strongly suggesting the presence of some β-structure, with a portion of it forming antiparallel strands (Alvarez et al., 1987, J. Biol. Chem., 262:3502–3509). Interpretations of CD evidence also appear divided. In one case, CD was said to indicate the presence in GLUT1 of some 82% α-helices, 10% β-turns and 8% random structure, with no β-strands. (Chin et al., 1987, Proc. Natl. Acad. Sci. USA, 84:4113–4116). However, more recently, use of an algorithm (Perezel et al., 1991, Protein Eng., 4:669–679) to analyze CD data led to predictions (Park et al., 1992, Protein Sci., 1:1032–1049) of β-structure in GLUT1, POR and OmpF, among other membrane proteins. Our assignments for GLUT1 structure are in line with the more recent FTIR and CD studes (Alvarez et al., supra.; Park et al., supra.).

Solvent accessibility of the GLUT backbone is better explained by the βB model.

Others and ourselves have reported evidence for the existence of a water-filled pore across GLUTs (Alvarez et al., 1987, J. Biol., Chem., 262:3502–3509; Jung et al., 1986, J. Biol. Chem., 261:9155–9160; Fischbarg et al., 1990, Proc. Natl. Acad. Sci. USA, 87:3244–3247). Such an open pathway would have to coexist with an apparent enzyme-type tight-fitting structure, since GLUTs display steric selectivity for substrates. This apparent contradiction may be resolved by noting that the water permeability of GLUTs (Fischbarg et al., 1993, Alfred Benzon Symp., 34:432–446) is only some 7% that of specific water channels (Preston et al., 1992, Science, 256:385–387), as if water traverses an open pathway through GLUTs only during part of a cycle of conformational changes. Both the 12H and βB models imply a hydrophilic pore in GLUT. On the basis of hydrogen-deuterium exchange, however, ≈90% of the GLUT1 amine protons are exchanged almost immediately (Alvarez et al., supra.; Hans et al., 1992, Trends Biochem. Sci., 17:328–333). These exchange data can be explained more readily if GLUT1 is a βB with a solvent-filled pore, as in that case most backbone amine hydrogens lining the pore and forming connecting loops would be accessible to solvent.

GLUT1 as a multifunctional βB transporter.

From recent evidence, compounds other than sugars such as water (Fischbarg et al., 1990, Proc. Natl. Acad. Sci. U.S.A., 87:3244–3247; Zhang et al., 1991, J. Clin. Invest., 88:1553–1558), nicotinamide (Sofue et al., 1992, Biochem. J., 288:669–674), and dehydroascorbic acid (Vera et al., 1993, Nature, 364:79–82) traverse GLUTs, suggesting that GLUTs are multifunctional (Sofue et al., supra.). Since a barrel framework is essentially fixed, as argued for porins, the GLUT1 connecting loops might operate as molecular gates and might also be involved in binding solutes and discriminating among them. The putative long intracellular GLUT1 loop (residues 204–270) may be an example, since glucose binding to the loop induces a conformational change in it (Asano et al., 1992, FEBS. Lett., 298:129–132) and antibodies against the peptide Asn-217-Il3-272 inhibit the binding of cytochalasin B to the protein). This loop may also have a binding site for ATP (Lys-225-Lys-229) (Carruthers et al., 1989, Biochemistry, 28:8337–8346) and protein kinase C phosphorylation sites (Ser-226, Ser-248) (Deziel et al., 1989, Int. J. Biochem., 21:807–814), all with potential functional roles. Lastly, all three antibodies we tested bind to putative mobile loops and enhance DOG uptake. The topology we propose is summarized in FIG. 6.

7. EXAMPLE

Further Proteins Shown to Include Beta-Barrel Structure

7.1. Materials and Methods

We obtained from databases (Swissprot, Protein Information Resource) the sequences of:

sw:p06009 Reaction center protein L chain (RCL).
sw:p02945 Bacteriorhodopsin precursor (BR)
sw:p04480 Colicin A (COLA).
pir3:s16070, *Rhodobacter capsulatus* porin (POR).
sw:p02931 *Escherichia coli* porin (Ompf).
sw:p11166 Glucose transporter type 1, erythrocyte/brain.
sw:p29972 Water channel protein for red blood cells and kidney proximal tubule (CHIP28).
sw:p02710 Acetylcholine receptor protein, alpha chain precursor
sw:p02920 Lactose permease
sw:p13866 Sodium/glucose cotransporter
sw:p08513 Potassium channel protein, larval (shaker-epsilon)
sw:p16614 Calcium-transporting ATPase sarcoplasmic reticulum type
sw:p20648 Potassium-transporting ATPase alpha chain (proton pump, gastric $H^+/K^+$-ATPase). (accession codes are given in parenthesis).

Predictions. Several algorithms were used. For hydropathy analysis, we calculated the average hydrophobicity $H_i$ for a span of i residues using the Kyte-Doolittle (KD) scale (Kyte and Doolittle, 1982, J. Mol. Biol., 157:105–132). We used spans of 21 and 7 residues. A span of 21 residues is appropriate because membrane spanning α-helices are of this or similar lengths. On the other hand, a shorter span can uncover trends in the hydrophobicity profile that the larger span might average out. We decided on 7 residues as the shortest span to give a representative picture of a local neighborhood in a chain without giving rise to excessive "noise". We also used the Union algorithm, described above, to predict protein segments expected to be transmembrane, namely, having relatively high hydrophobicity and propensity to form amphiphilic α or β structures.

We also employed the Chou-Fasman prediciton method as implemented in the Chou-Fasman-Prevelige (CFP) algorithm (Prevelige et al., "Chou-Fasman prediction of the secondary structure of proteins: Chou-Fasman-Prevelige algorithm. In: G. D. Fasman (eds). Prediction of protein structure and the principles of protein conformation", Plenum Press, New York, N.Y., pp. 391–416 (1989)). Our figures showed α and β average propensities calculated for tetrapeptides and assigned to the first residue, following the CFP procedure. Where these propensities equal or surpass the CF threshold (100 in their units), we mark the segments (α prd and β prd lines). We also show the CF <pt> propensity; where <pt> exceeds the threshold recommended in the CFP procedure (0.00075), 4-residue predicted turns are marked by lines (denoted as "t prd") beginning with the suprathreshold residue. Our routine simply marks all such 4-point turns, rather than attempting to opt between them (as in the CFP procedure) when they overlap.

We also used the results obtained with the PHD neural network prediction program (Rost and Sander, 1992, Nature, 360:540), which runs without human intervention in a computer, and is therefore unbiased to that extent.

We found that, as a rule, no single procedure was completely sufficient, and it was best to combine in one figure several different types of plots so as to compare them and derive a global picture for a given protein. To that end, we wrote a program ("UCFP") in the PowerBasic language (Power-BASIC Inc., Brentwood, Calif. 94513), compiled it, and ran the executable file under IBMDOS. The source code of UCFP is set forth in FIG. 12. UCFP is a predecessor of the UNION program, and uses as inputs two files: a) the amino acid sequence of a protein, and b) a file with literal secondary structural assignment codes for that sequence, either taken from the Brookhaven database for proteins with known structure or derived from predictions for proteins of unknown structure. Our program computes hydrophobicities, U and CFP α, β and pt propensities, converts the literal structure codes into numbers, and generates a columnar output file. We obtained the figures presented here by importing UCF output into a graphics program ("Origin", MicroCal Software, Northampton, Mass. 01060). We also found useful the graphic display program "PSAAM" (Crofts, AR, "Protein Sequence Analysis and Modeling for Windows 3 [ ],", University of Illinois, Urbana, Ill. (Ph.D.; Dissertation)) to verify the validity of our algorithms.

7.2. Results
Evaluation of the prediciton profiles.

Validations: (1) multihelical proteins.

Figure 7A:
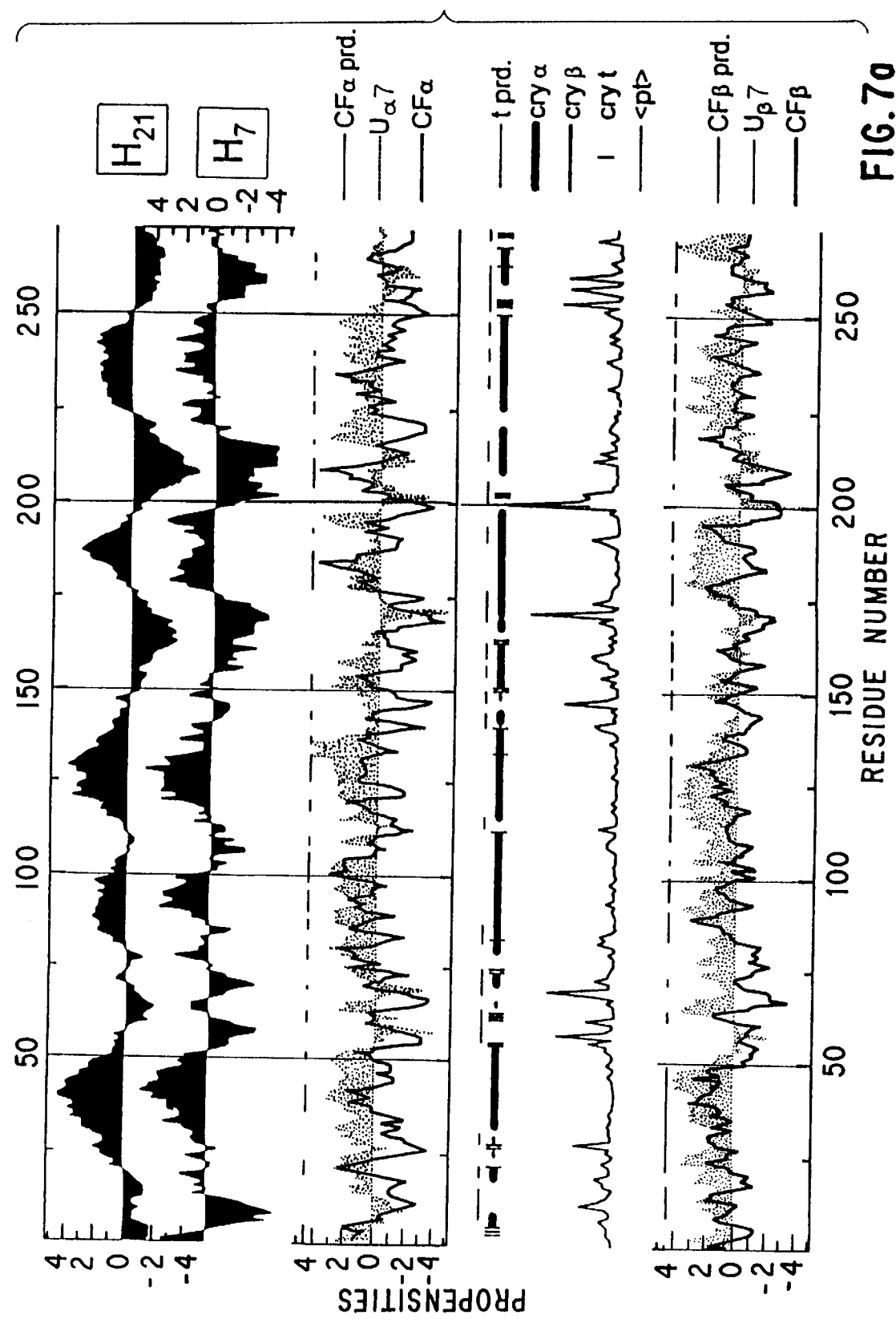

The reaction center (L chain) constitutes a good example of a successful prediction (FIG. 7a). The H7 profile marks several hydrophobic segments which are long enough to span the membrane. This prediction of long segments is borne out by the $U_{\alpha 7}$ peaks, and by the relative paucity of predicted turns, leaving long stretches of sequence with little turn propensity and hence with relatively higher propensity to form structure. An assignment to multi-α folding could be made at this point, after which the segments could be refined using a detailed CFP spreadsheet (Prevelige, supra.), cap propensities, and so on.

Figure 7B:
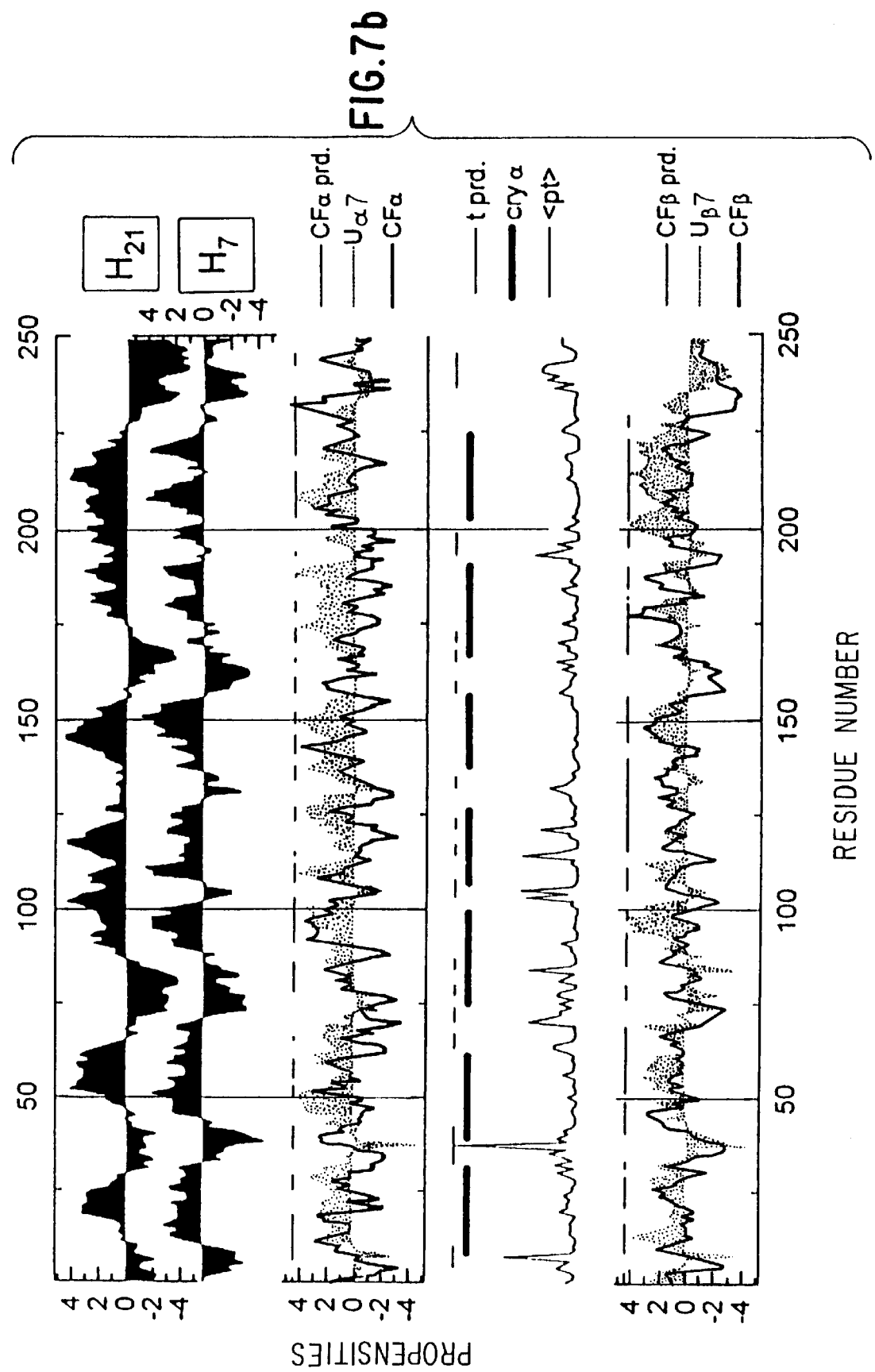
Figure 7C:
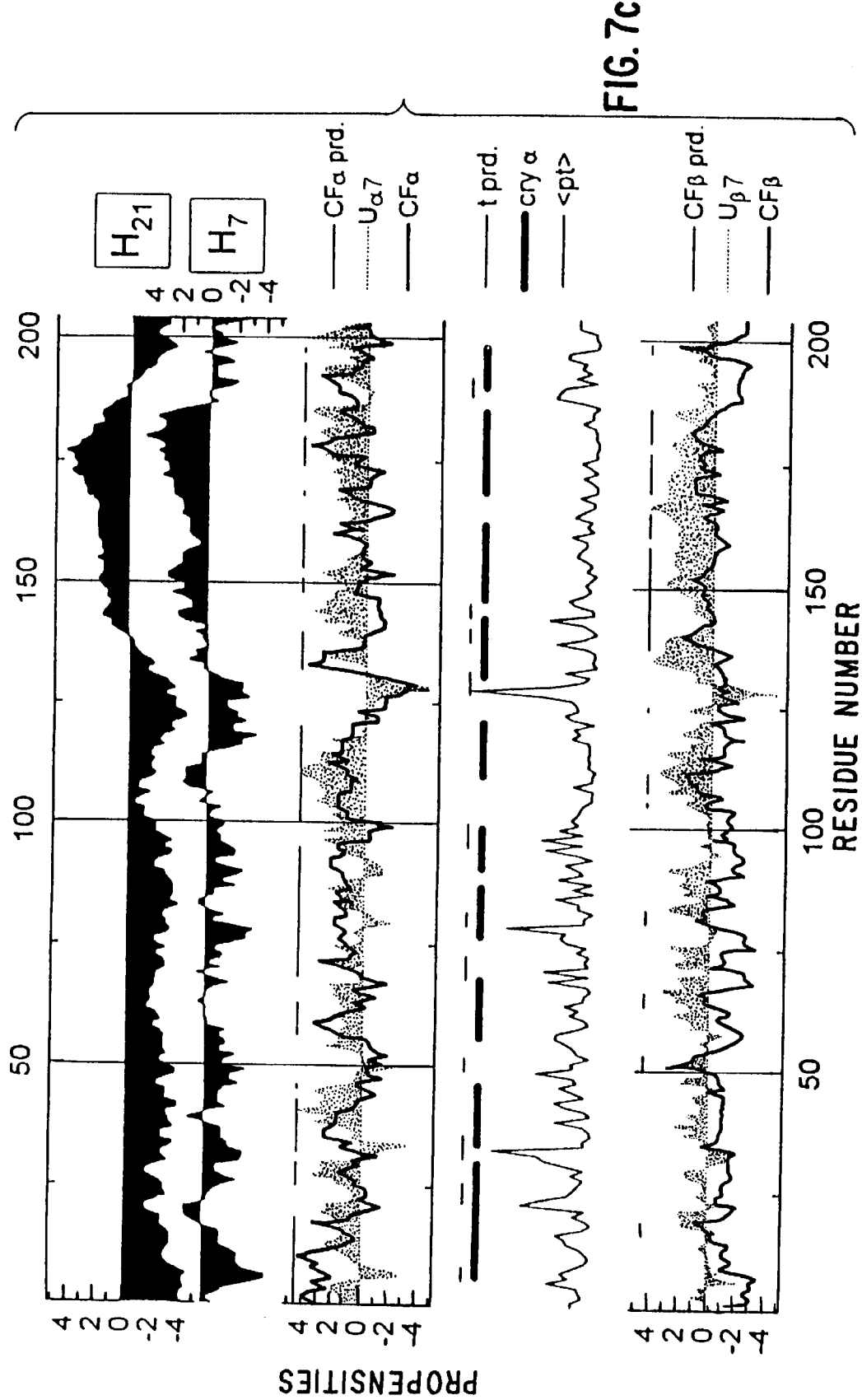
Figure 7D:
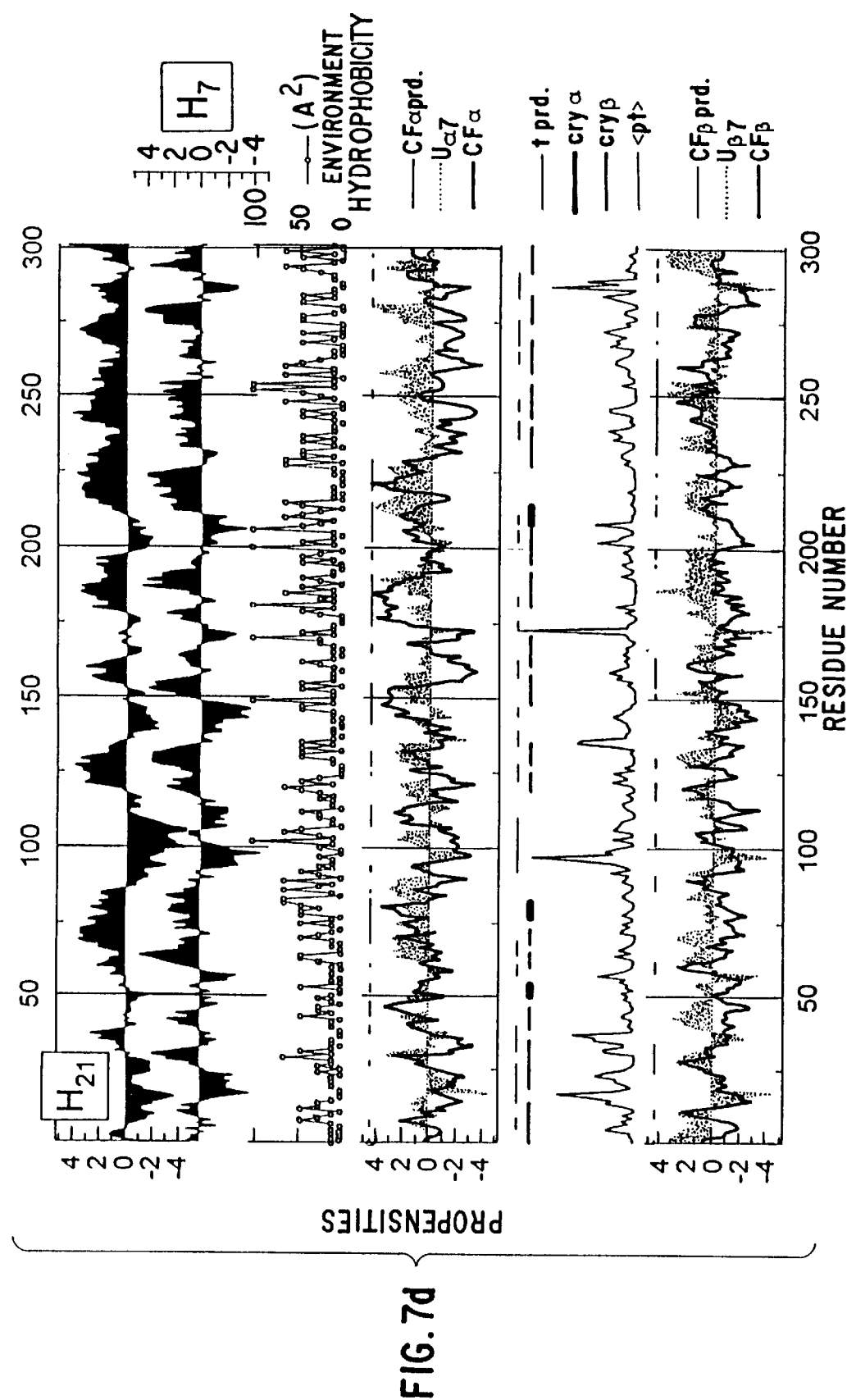
Figure 7E:
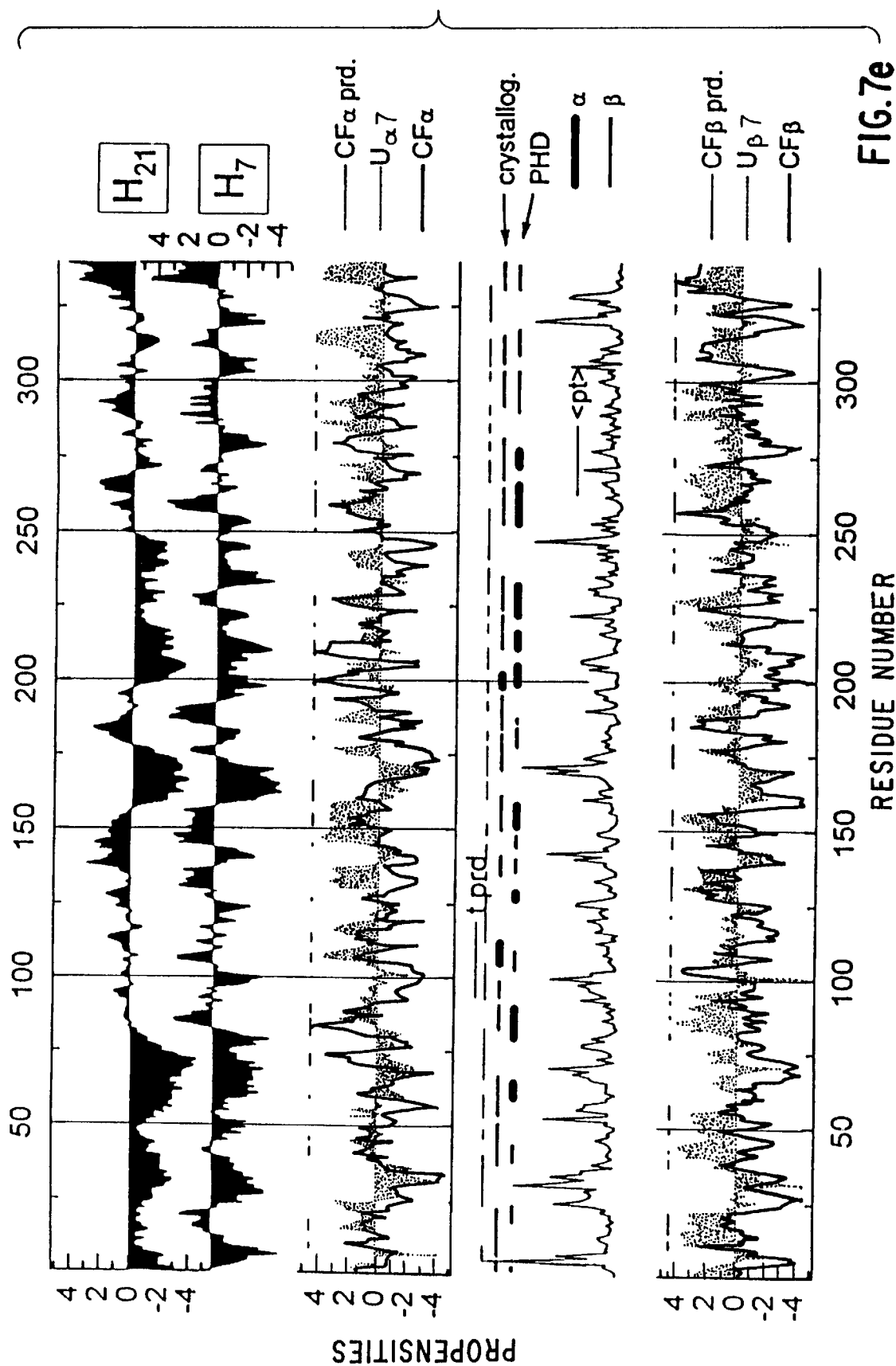

Bacteriorhodopsin also evidences long hydrophobic stretches ($H_7$) borne out by $U_{\alpha 7}$ peaks, and relatively few predicted turn regions (FIG. 7b). The trend to long structured segments is curiously more discernible in the CFP-β predictions than in the α-predictions. Still, the protein can be classed as multi-α on the basis of the length of the predicted segments.

For colicin (FIG. 7c), hydrophobicity analysis alone seems insufficient, since it predicts long stretches known as transmembrane as hydrophilic. Our way of plotting normalized (rather than absolute) H values exaggerates this trend, which is nonetheless noteworthy. In this instance, CFP α-predictions and $U_{\alpha 7}$ profiles demonstrate that the length of the predicted segments is consistent with multi-α-helical fold. Overall CFP α-propensity is higher than that for β (we plot absolute values for both). Hence, multi-α assignment seems adequate.

Validations: (2) porins.

*Rhodobacter capsulatus* porin exemplifies a trend (FIG. 7d): some peaks that appear as long hydrophobic stretches in the $H_{21}$ profile are split in the $H_7$ profile. Even if qualitative judgments are tentative, this does not happen to the same extent in RCL or BR. Neither the α nor the β predictions mark long segments here, and turn propensity peaks appear frequently along the chain. A tentative assignment of multi-β fold can be made at this point. If one then focuses attention on the $U_{b7}$ peaks, one can verify that they mark the β-segments exceedingly well. At a threshold of 1.83, all strands will be marked, with minimal overprediction. Segments lengths could be further refined as above.

The *Escherichia coli* porin profiles (FIG. 7e) show further the limitations of hydrophobicity analysis per se. The hydrophobicity profiles largely miss the β-hairpin between residues 35–65. However, the CFP β-predictions and U for β segments find them. The U peaks are especially noteworthy; as above, with a threshold of 2.15, U marks all the β-strands with minimal overprediction. One can note also repeated suprathreshold turn predictions, seemingly at regular intervals; from all this, a tentative assignment of multi-β structure may be made. This plot also allows the rare opportunity of evaluating the performance of the PHD robot by comparing the structure derived from crystallography with a prediction PHD made of this protein shortly before it was incorporated to its database. Practically all structured segments are detected by PHD, which also does reasonably well in predicting their lengths. Once more, those lengths are too short for transmembrane α-helices, but adequate for β-strands, confirming the tentative assignment above. There is another feature of the PHD prediction worth noting: as many as 7 β-segments are predicted as α-helical, while one of the short α-helices is predicted as a β-strand. Such types of mispredictions can be common when humans make their own judgments, so here the computer brings no improvement. The advantage a human has is to know that the protein is in a membrane, and hence that the structured segments predicted as α-helical are too short to be transmembrane, pointing instead to a β-barrel.

In closing this section, we note that the group of proteins reviewed so far has a common feature: they tend to have relatively short sequences, not exceeding some 350 amino acids. Perhaps that has made crystallizing them somewhat easier, certainly predictions also appear relatively straightforward, compared with some for the longer sequences.

Proteins with unknown structure.

Figure 8A:
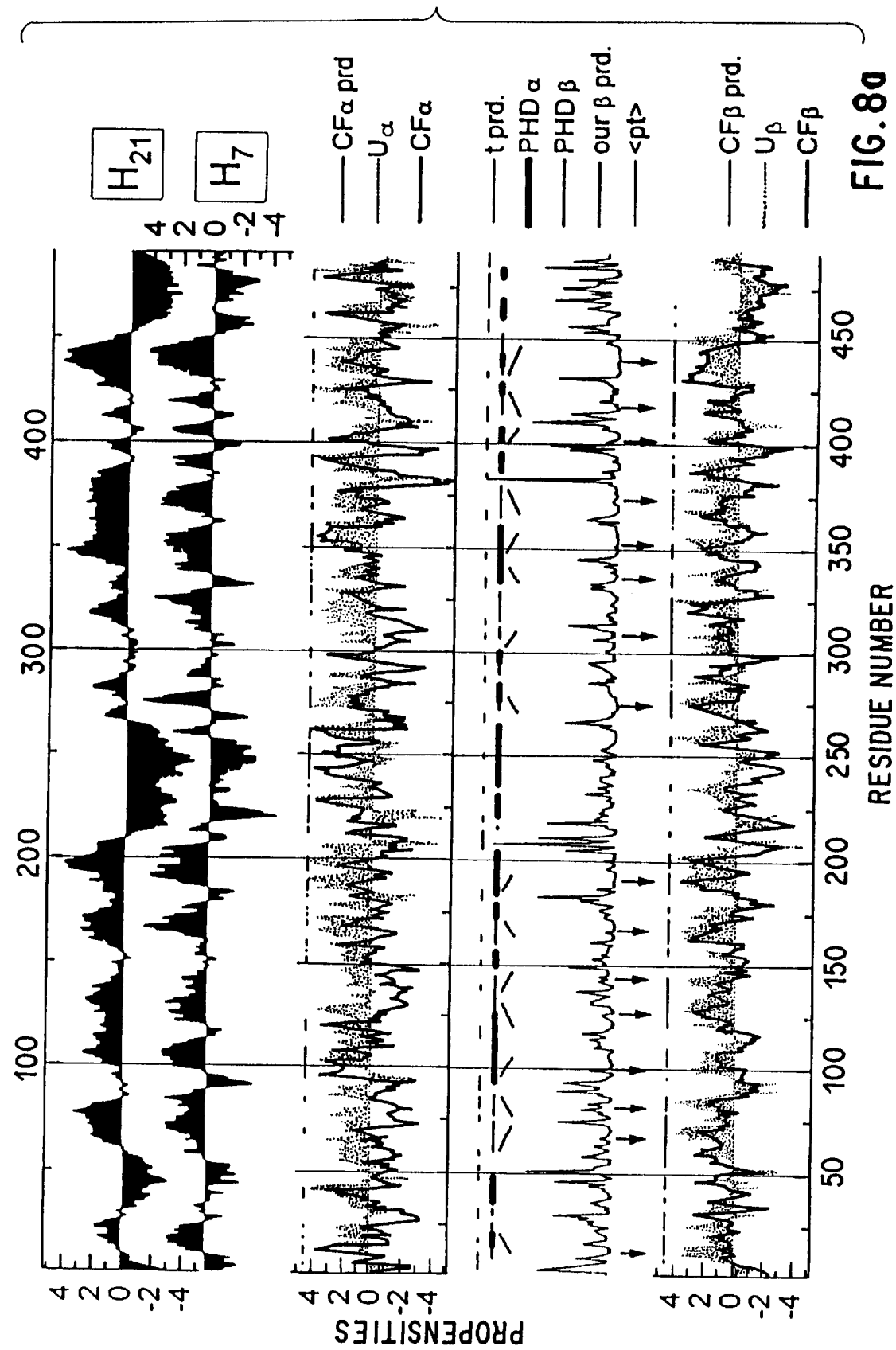
Figure 8B:
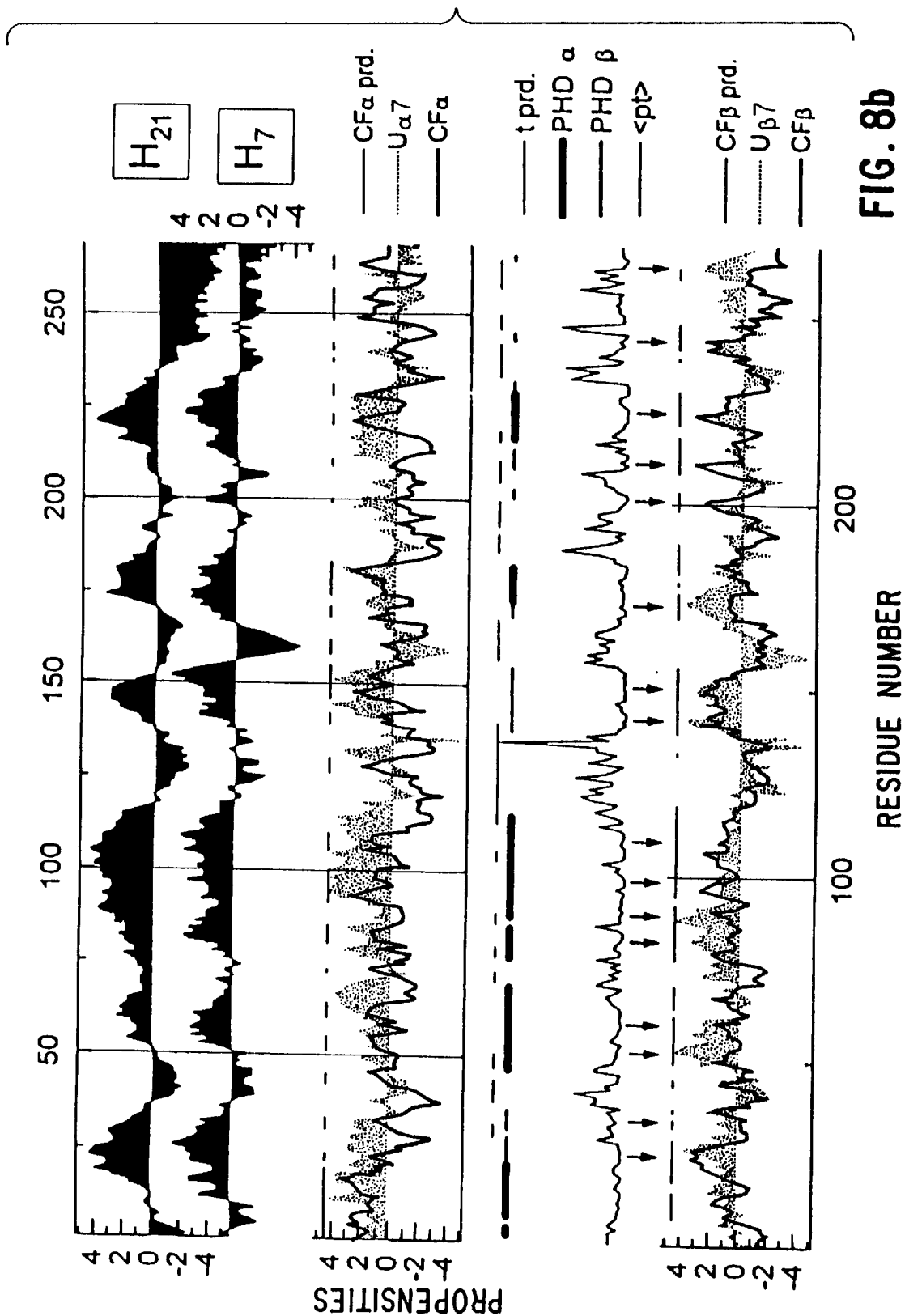
Figure 8C:
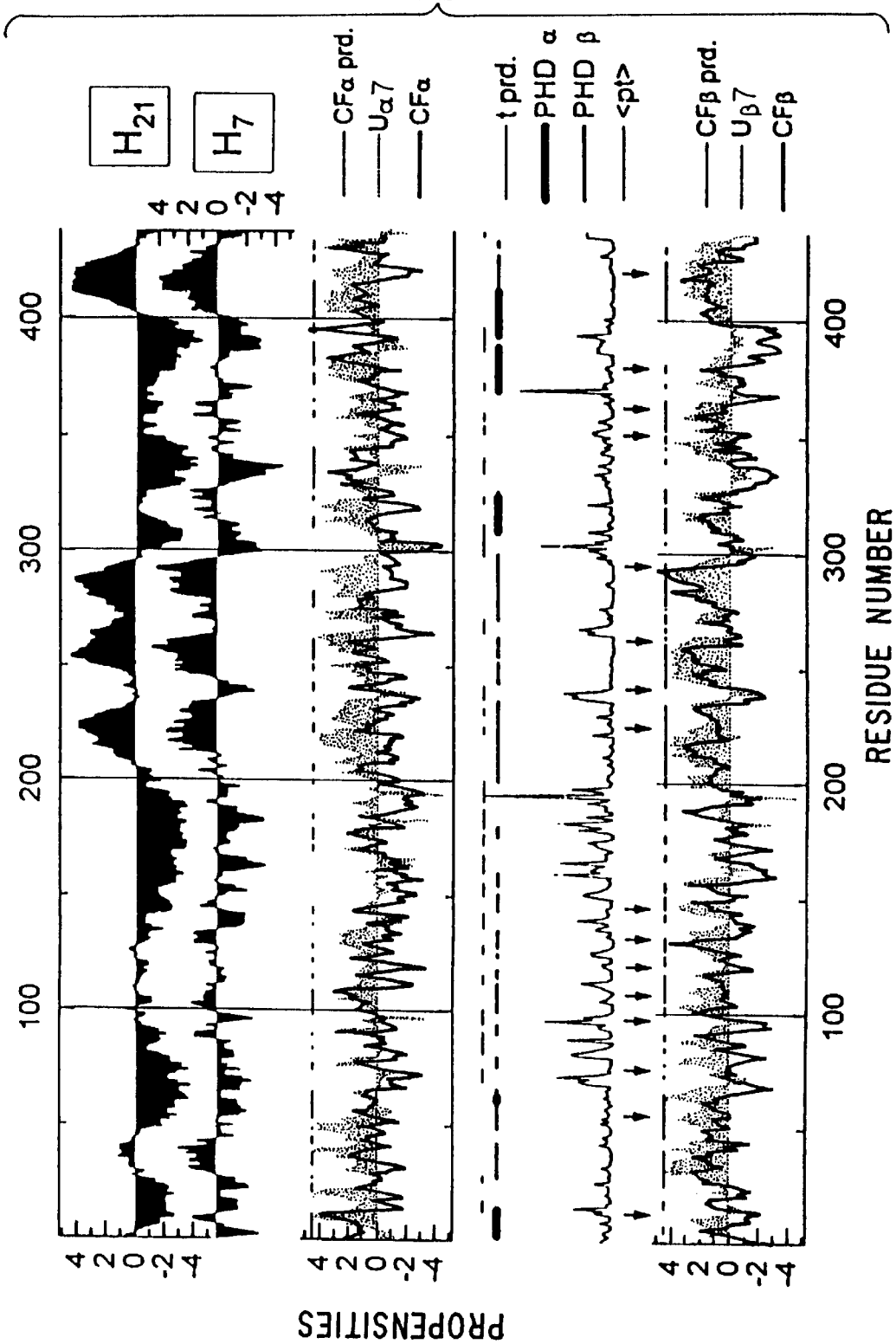

The prediction profiles for facilitative glucose transporter indicate a number of short segments (FIG. 8a). PHD predicts only three long segments as α-helical. Yet, of these, the middle one (#230–260) forms part of a known long intracellular loop, and might be actually broken by a turn. In view of the number of predicted short segments, the remaining two long segments could not suffice to label the protein as multi-α-helical. When analyzed more closely, predicted turns can be discerned that could interrupt those segments. In contrast, the $U_{b7}$ peaks, β predictions, and a good number of PHD-predicted segments are in register and give a cogent picture of short segments, the approximate location of which we mark with arrows. One can note how the segments may be nested between predicted turns. Partly on this basis, we have predicted for this protein a porin-like multi-β folding, with some α-helices in the connecting loops. We also show in the fourth panel the possible orientation of the predicted β-strands.

CHIP28:

PHD predicts (FIG. 8b) only two segments long enough to be transmembrane as α-helices, which makes assignment as multi-helical somewhat doubtful. In addition, turn propensities are rather high and repeated along the chain, which speaks for short structured segments. The next feature to are the β-predictions, $U_{\beta 7}$ peaks and PHD-predicted β segments in register along the second half of the sequence. If one now returns to the two long segments, predicted turns are discernible that could break them (one supra, one sub-threshold). Therefore, we assign the protein as multi-β, and mark the 16 putative segments that would give it a porin-type fold. In this view, given its short sequence there would be little in this structure aside from the barrel itself, since the connecting loops would be rather short (except perhaps for the segment 110–140). One might think of it as a rudimentary or bare-bones channel protein.

The acetylcholine receptor α subunit:

The $H_{21}$ profile (FIG. 8c) yields several hydrophobic stretches long enough to be transmembrane α-helices; these (M1-4) have been recognized for years. One of the long stretches (M2) is under particular scrutiny as a firm candidate to line the channel (see Karlin A, 1991, "Explorations of the nicotinic acetylcholine receptor", The Harvey Lecture series 85:71–107) for how the different subunits might join to form a channel.)

On the other hand, in the profiles shown here, detail multiplies as one progresses from $H_{21}$ to the other ones. It seems particularly noteworthy that the CFβ and $U_{b7}$ propensities and PHD segment predictions are in register throughout the sequence. The CFα and Hα7 propensities are not, which gives a tentative indication of multi-β folding. We have marked with arrows some segments as the putative 16 β-strands of a porin fold. In Akabas et al., 1992, Science, 258:307–310, evidence from cysteine-substituted mutants led the authors to describe segment 248–254 as probably forming a β-strand. Our prediction also finds β-structure in that region.

The potential participation of residues 1–200 in forming a channel has been apparently neglected so far, presumably because in the current view, all five receptor subunits would join together and instead simply form a channel lined by their M2 segments. However, these two views are not necessarily mutually exclusive, as a comparison with porins may show. Porins consist of trimers in which each monomer forms its own channel at one end of the molecule. At the other end, however, the individual channels merge into one large opening for the trimer. One wonders whether other membrane proteins may show a similar arrangement in which channel-containing subunits in varying numbers join in to share their openings. For the acetylcholine receptor, it might explain both the clear evidence for a large opening facing the extracellular space and lined by the 5 monomers (Karlin, supra), and the predictions for the stretch 1–200 if each subunit would form its own channel at their intracellular ends, all channels eventually merging.

Lactose permease.

Figure 8D:
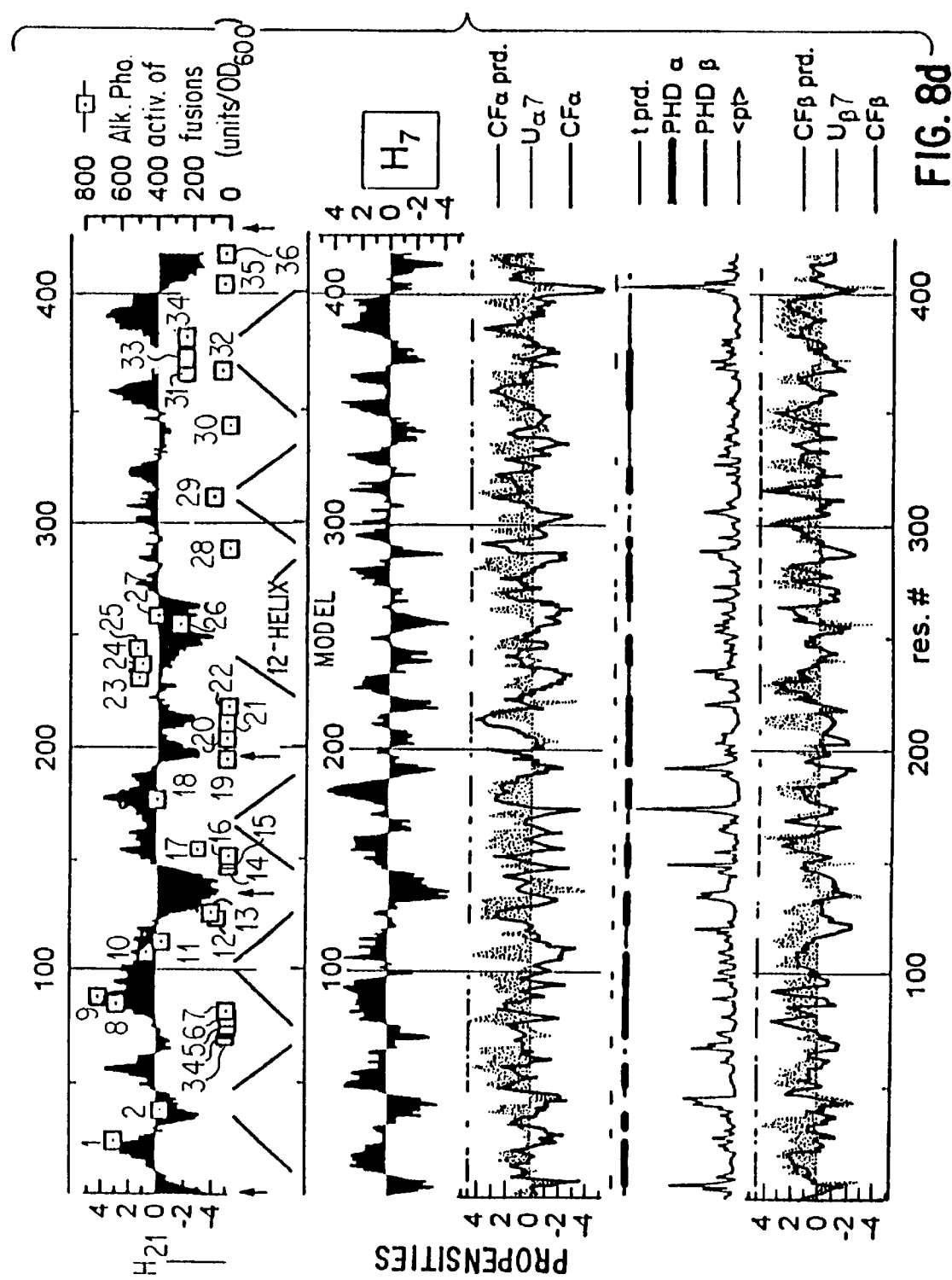
Figure 8E:
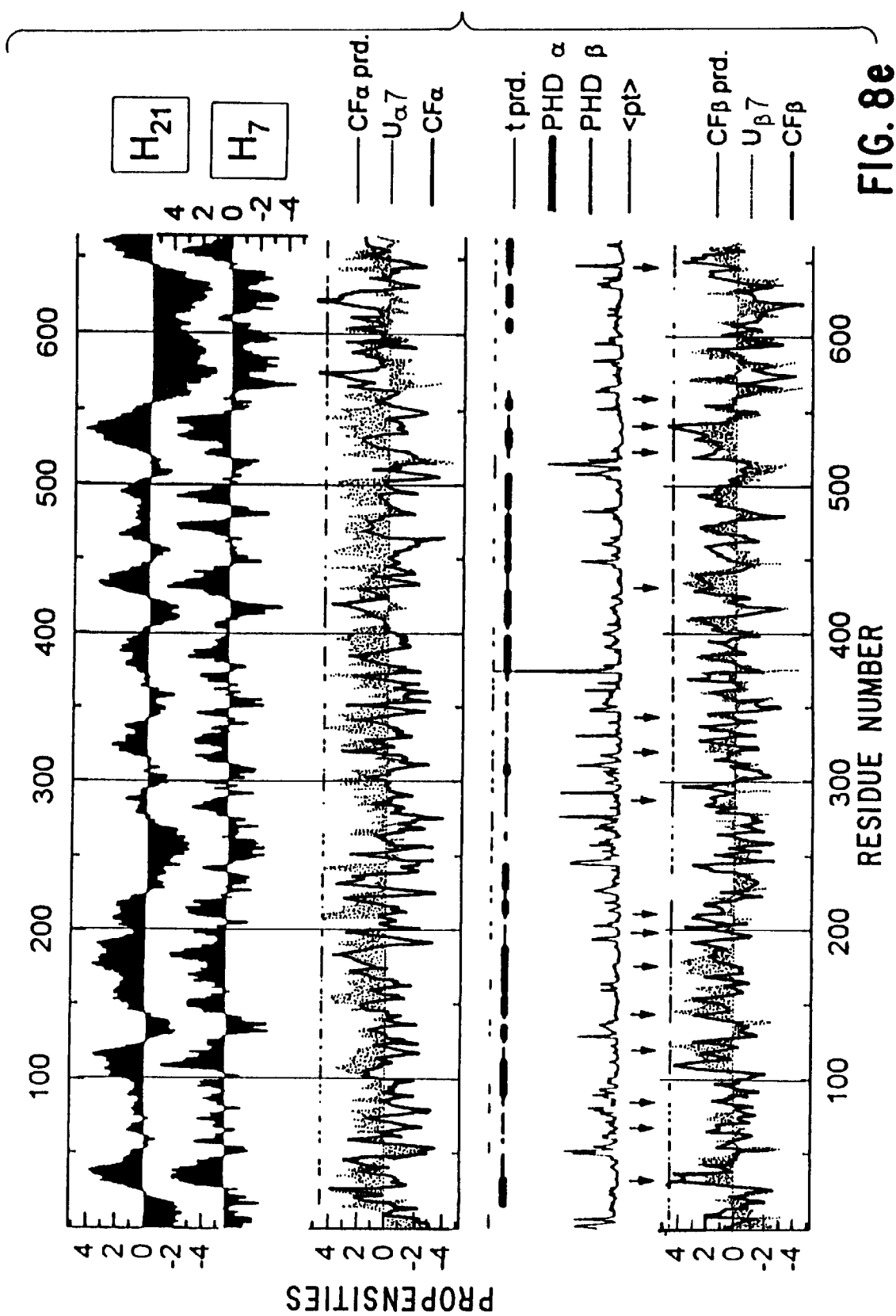

Once more, the CFβ and $U_{b7}$ profiles go in register, especially in the second half of the sequence (FIG. 8d). That cannot be said of the CFα and Uα7 profiles, which again tentatively indicates multi-β folding. PHD predicts some 15 β segments, which reinforces this possibility. PHD also predicts five α-helices with length presumably sufficient to span the membrane (residues 7–26, 72–90, 194–223, 267–287, and 352–376). However, the segment 194–223 is marked by several fusions in the top panel as intracellular, and appears as a hydrophilic region in $H_{21}$, so it seems logical to discard it. The remaining four long segments, even if helical, do not appear enough to form a transmembrane pore of the dimensions required for lactose permeation. Besides, all of them are potentially interrupted or shortened by suprathreshold turn predictions. In view of all this, multi-β folding appears a more logical choice.

This conclusion goes counter to that drawn in several studies in which evidence for a multi-α-helical fold was presented (Kaback, 1992, Int. Rev. Cytol., 137A:97–125). On the other hand, the possibility of extensive β-folding for the lac permease has been advanced before by Radding (Karlin, supra). More recently, the results of Calamia and Manoil, obtained from fusions, have been cited to support the topology of the 12-helix lac permease model (Kaback, supra) and to support the idea that facilitators conforming to a 6+6 hydrophobicity profile are α-helical (Nikaido et al., 1992, Science, 258:936–942). Calamia and Manoil apparently selected the locations of their fusions for the limited aim of discriminating between the 12-helix and the 14-helix lac permease models. The fact that their results support the 12-helix model says little (if anything) about whether a-helical folding is to be favored over an alternative such as the partial β-barrel fold proposed by Radding (Karlin, supra), or over a possible 16-β-strand porin fold. In fact, some of the findings of Calamia and Manoil may be taken as possible indications of β-folding. In their own words, ". . . it appears that 9–11 apolar membrane spanning segments can suffice to promote efficient alkaline phosphatase translocation across the membrane." Another interpretation might be that the transmembrane segments referred to would be 9–11 residues in length, that is, too short to be α-helical but quite of the correct length for a transmembrane β-strand. In addition, the segment between fusions 9 and 10, each one labeling residues as extracellular, is long enough that the chain, if consisting of short β-strands, could have entered the cell and returned outside. Lastly, fusion 29 apparently labels a stretch as intracellular when an extracellular location was expected; the small increase in activity of fusion 29 appears of dubious significance in view of the fact that fusion 13, also of small but non-zero activity, may be labeling an intracellular location. In a similar vein, the observed range of alkaline phosphatase activities (as against an ideal all-or-none pattern) poses some question as to which locations the intermediate activities may be labeling. A more substantial link between results of fusions and topology may be clearer if control fusions and subsequent expression can be done with membrane proteins of known structure.

Figure 8F:
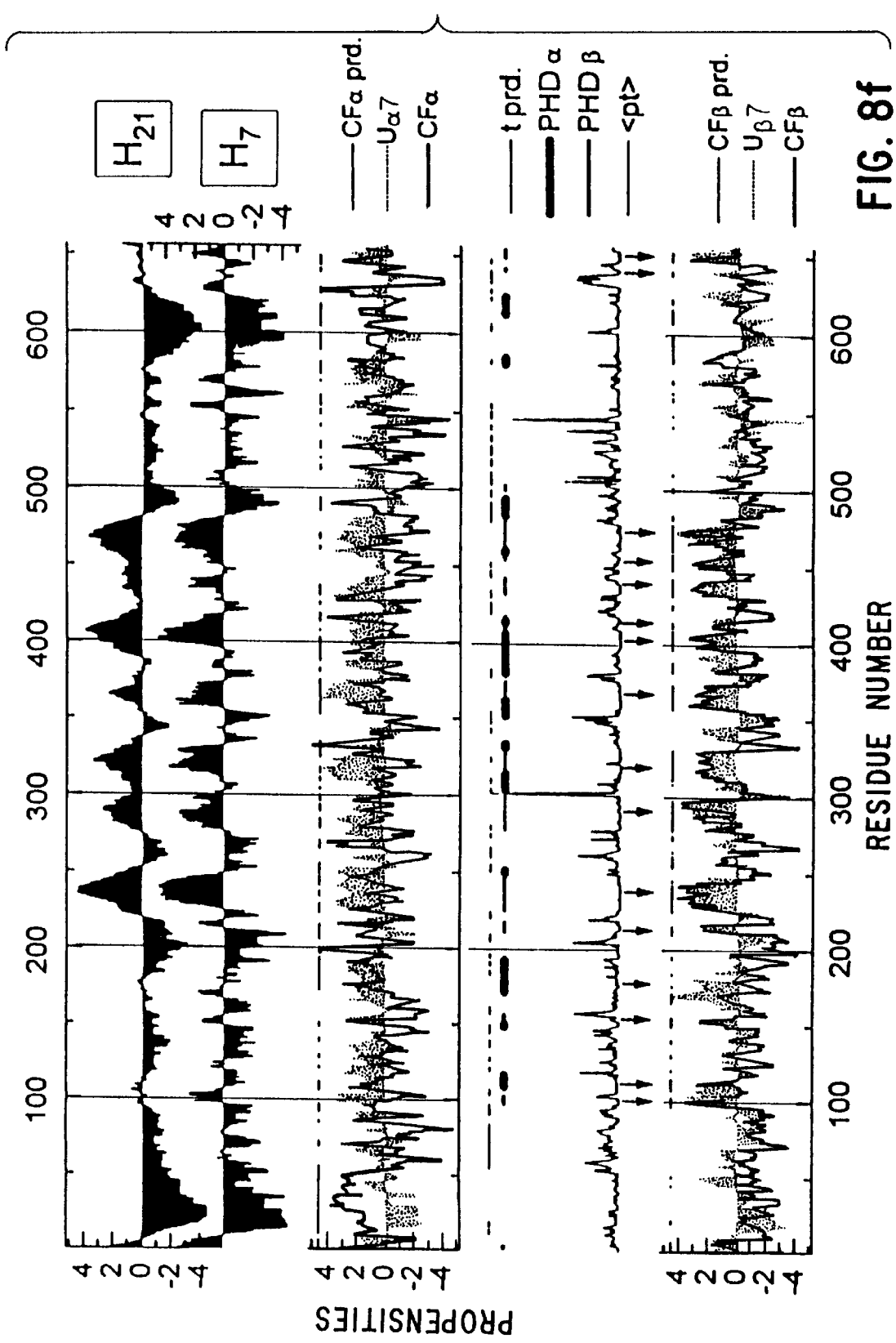
Figure 8G:
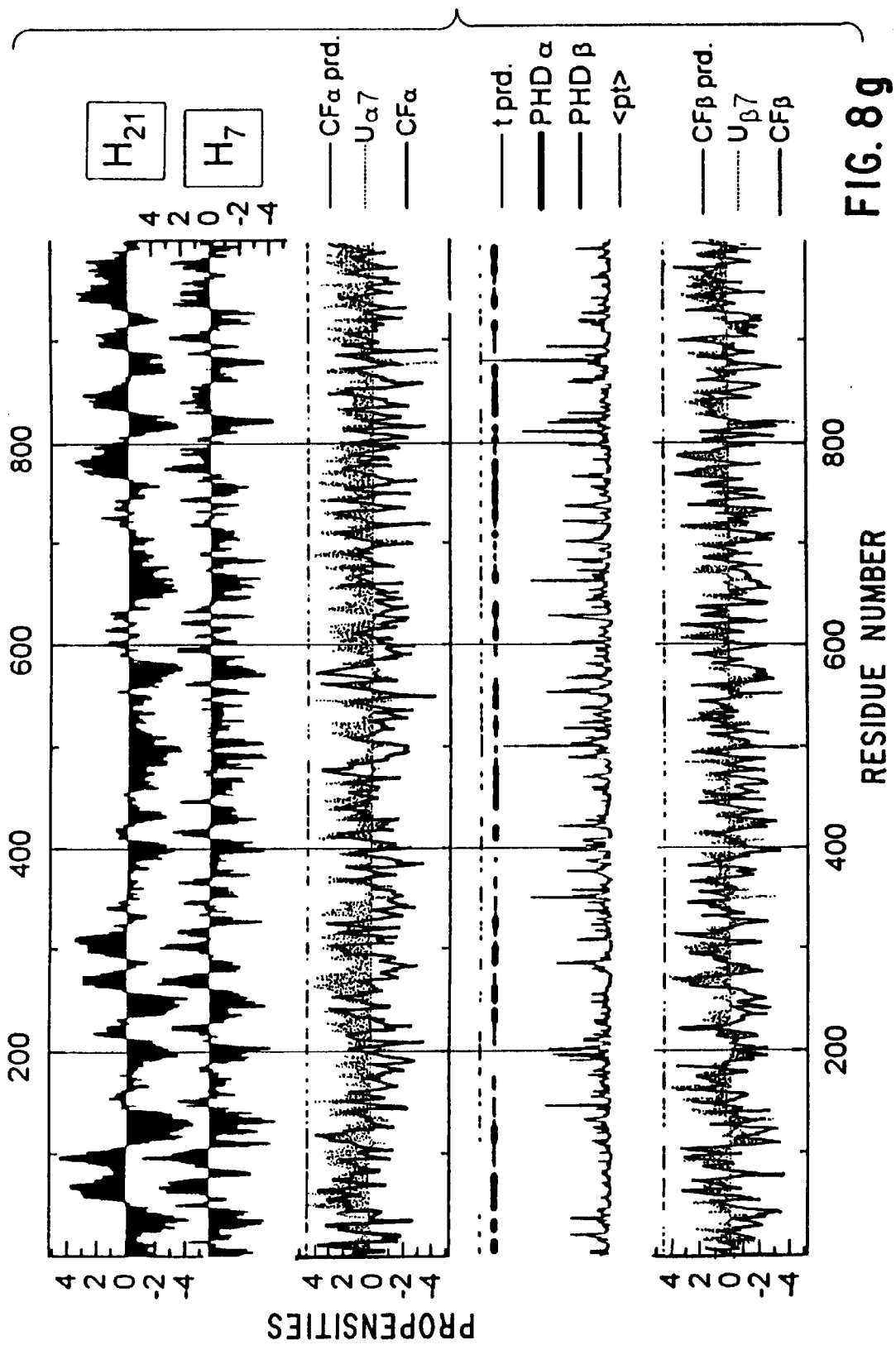

Sodium-glucose cotransporter (FIG. 8e), $K^+$ channel (FIG. 8f).

Several of the patterns already referred to above reappear for these sequences. CFβ, $U_{β7}$ and PHD predictions are in register, while those for CFα and $U_{α7}$ do not seem to be. Turn potentials rise regularly and delimit segments of 10 residues or less. Once more, a multi-β assignment seems plausible. We have marked with arrows segments that might contribute to porin folds. There is evidence that the functional unit for this $K^+$ channel is a tetramer (MacKinnon, 1991, Nature, 350:232–235); the comments made above for the acetylcholine receptor apply here as well, namely, each monomer may have its own channel, with all four channels merging into one.

Figure 8H:
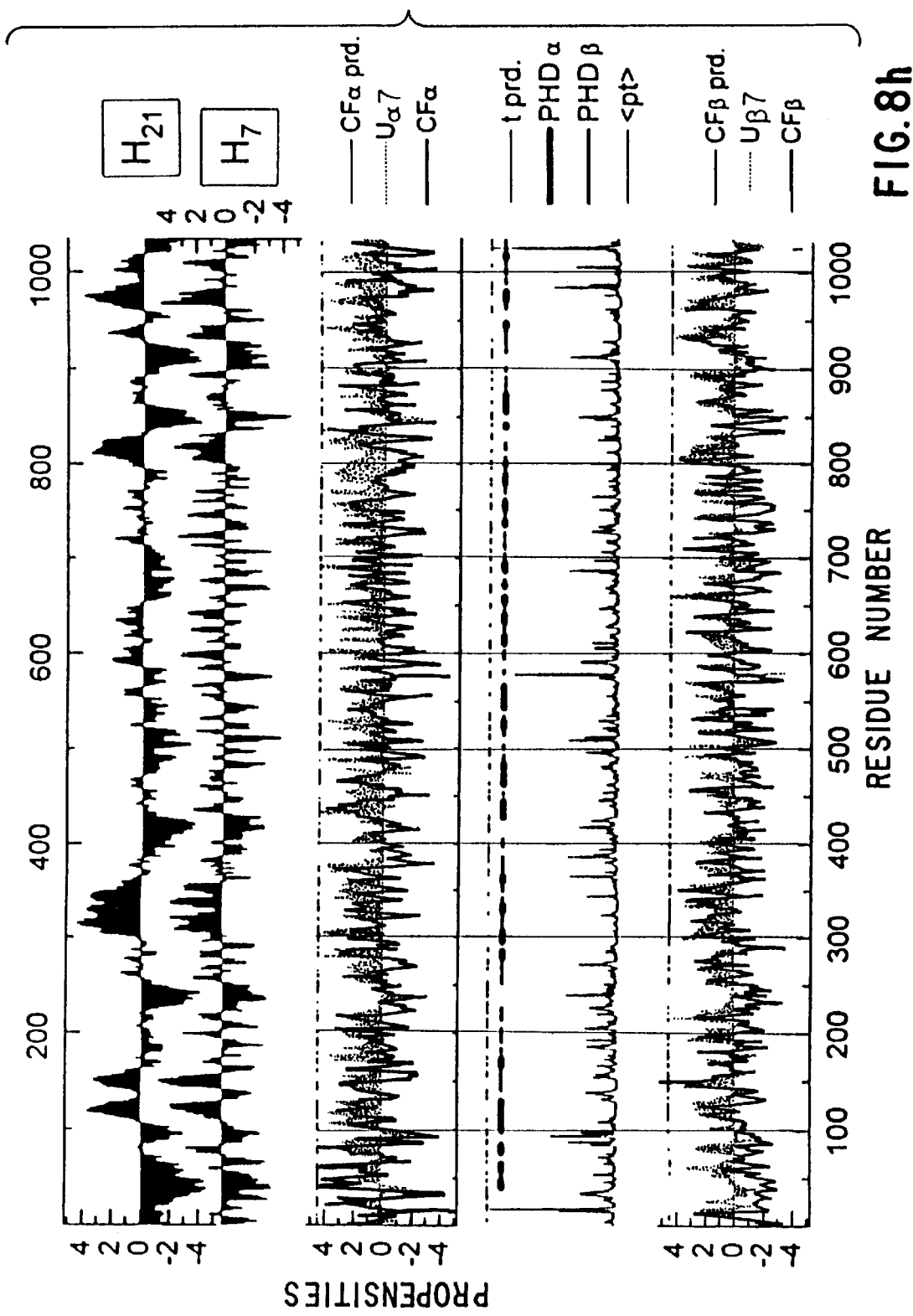

Calcium ATPase (FIG. 2g), $H^+/K^+$-ATPase (FIG. 8h).

The length of the sequences does not allow an intuitive comparison on the same basis as we have done until now. Of course, these proteins may contain homologous internal repeats, and if so perhaps a more detailed analysis might be performed on each repeat. For the present purposes, we will simply call attention to the CFβ, $U_{b7}$ and PHD predictions in register, the number of comparatively short segments predicted (having the proper length for transmembrane β-strands), and the regularity with which peaks appear in the <pt> profile, all of which is consistent with β-folding.

Profile analysis of environmental similarity.

We resorted to this recently developed methodology (Gribskow et al., 1990, "Profile analysis. In: R. F. Doolittle (eds). Methods in Enzymology", Academic Press, New York, pp. 146–159; Bowie et al., 1991, Science, 253:164–170). We chose as terms of comparison two environments, those of RCL and Ompf, and set out to investigate whether membrane proteins of interest would have environmental scores closer to one or the other. The results are summarized in FIGS. 9a and 9b. For reasons we discuss below, we think this type of analysis does not perform optimally for membrane proteins. Still, some trends are apparent. The Ompf profile (FIG. 9a) recognizes several porins and members of the major facilitator superfamily of proteins, a group that includes the sugar transporters, and gives them better scores than those of most globular unrelated proteins or BR. Conversely, the RCL profile (FIG. 9b) recognizes the RC M chain and BR better than facilitators or porins.

7.3. Discussion

Translocators: economy of the barrel design.

Since a main common function of transporters and channels is to allow passage ("translocation") of solutes across the membrane, in what follows we will refer to them as "translocators". Given a limited number of residues, a β-strand can span a membrane with much fewer of them (beginning with six (Rosenbusch, 1985, EMBO J., 4:1593–1597); 10 is certainly adequate). Hence, as already noted (Radding, 1991, J. Theor Biol., 150:239–249), much less residues are needed to configure a transmembrane translocation unit if the unit is a β-barrel than if the transmembrane segments are α-helical.

The width of the barrel, and the role of the connecting loops.

When contemplating a possible β-barrel model for translocators, it seems logical at first to focus on known β-barrel folds so as to determine which one might have a channel suited for translocation. The choice so far seems limited to two main types, the α-β barrels of isomerase-type enzymes (Farber et al., 1990, TIBS, 15:228–234) and the porins. The β-barrel lumen of the 8-stranded isomerase fold, however, appears to be very small, perhaps only 1–2 angstroms. Of course, the pore of the 16-stranded porins is much wider; in Ompf, even with a loop inside its pore and constricting it, its diameter is 7×11 angstroms (Cowan et al., 1992, Nature, 358:727–733). This is adequate for large solutes, but appears excessive for ionic channels and transporters of small solutes. If such translocators have a porin fold, their pores may be modified by loops. Hence, some connecting loops in translocators may fulfill specific functions such as gating a channel, constricting a channel pore, binding to and hence selecting solutes, binding metabolites and cofactors, signaling destination in protein traffic, etc. Evolutionarily, it seems easier to explain the development of translocators if a common translocation unit was conserved (a 16-stranded β-barrel) and different loops evolved for different functions. A similar scheme was advanced by Nikaido and Saier for bacterial facilitators, except that the translocation unit they envisaged was 12-α-helical (Nikaido et al., 1992, Science, 258:936–942). In our view, the common translocation unit would be a β-barrel. With this proviso, the idea of a common translocation unit could be extended to ionic channels (see FIG. 8f), with suitable loops evolutionarily grafted for each given protein (Nikaido, supra). In fact, a β-barrel model has been previously proposed for the voltage-activated $K^+$ channel (Bogusz et al., 1992, Protein-Eng., 5(4):285–293).

For an alternative, one would have to consider the evolutionary development of translocators by a process that would have tailored the number of strands and hence the width of the channel to the size of the solute considered. Aside from being overly complex, that is not what the evidence points to for bacterial facilitators (Nikaido, supra). In this light, we deem the work of Radding (Karlin, supra) important to point out the possible presence of β structure in lac permease and the $Na^+/H^+$ antiporter, a concept with which we agree (cf. our FIGS. 9d for the lac permease and 9h for the $H^+/K^+$-ATPase). On the other hand, the partial β-barrels that he proposes may be more difficult to marry with the evolutionary considerations above. From all this, the porin fold emerges as an interesting candidate for a template common to most if not all translocators.

The connecting loops of barrels.

In an anti-parallel β-barrel, the loops connecting one strand with the next one can be relatively short, sometimes no longer than needed for a turn. The arrangement has a certain symmetry in that each strand connects only with the neighboring ones, thereby decreasing potential steric conflicts between different loops. This is what happens in porins. In the view we propose, such loops would be crucial, since the translocating unit made out of a β-barrel would be too static to result in, say, gating. Conformational changes associated with binding and/or selectivity are also easier to conceive if they involve only loops, rather than massive protein segments.

One might also mention that finite water permeability through proteins has been shown to exist not only across water channels such as CHIP28 or γ-TIP but across several transporters such as GLUT1, the sodium/glucose cotransporter, and CFTR (Hasegawa et al., 1991, Science, 258:1477–1479). Water permeation could of course take place through any type of preferential pathway in a protein, but the presence of β-barrels acting as translocation pathways would provide a ready explanation for water passage through transporters.

Figure 9B:
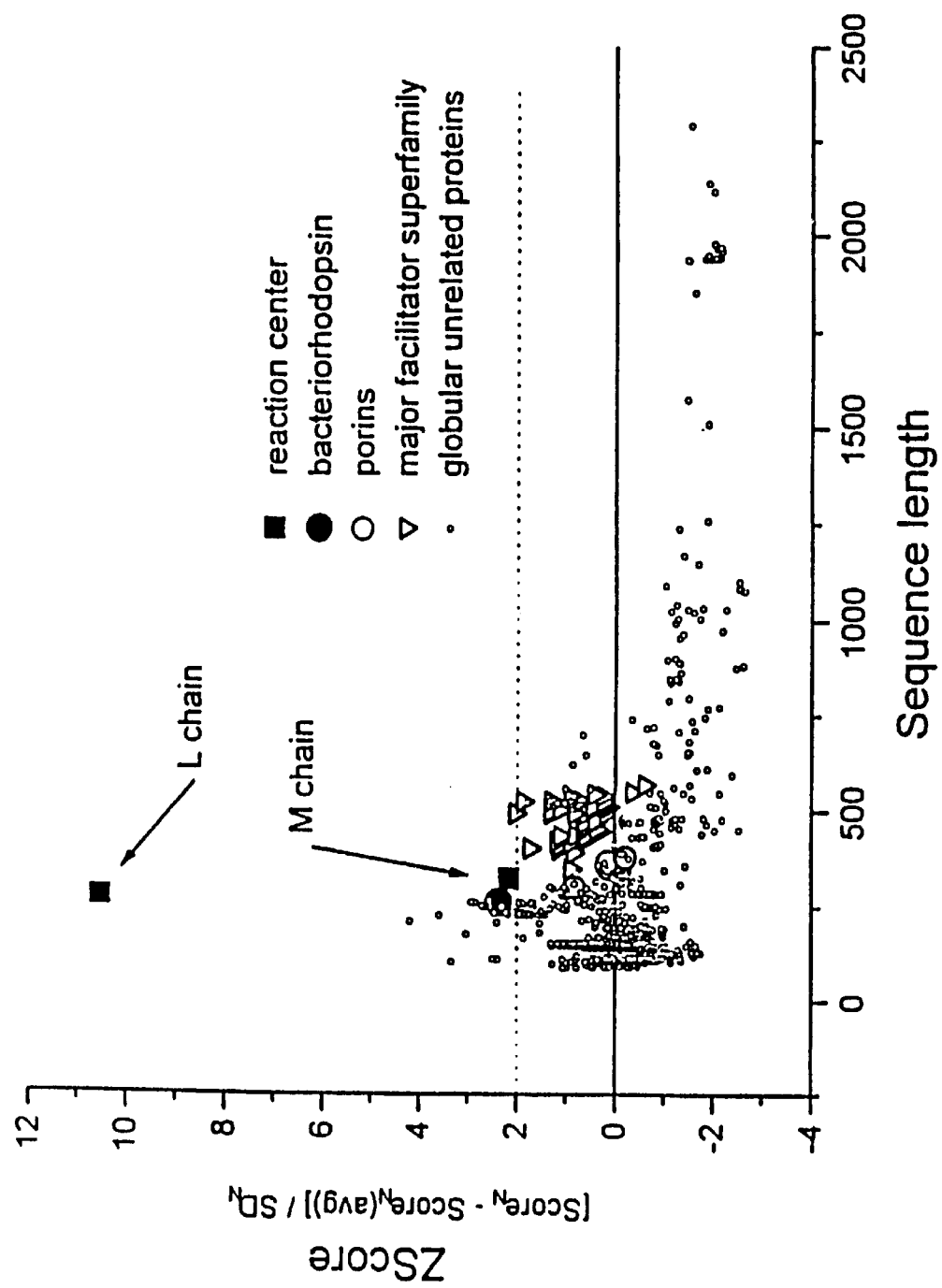

Analysis of environmental scores in membrane proteins. The profile analysis methodology has been developed for globular proteins. Hence, in the way it currently stands, the side chains pointing outward from the protein are necessarily assumed to be exposed to water. By design, the profile program does not differentiate between globular and membrane proteins. In consequence, the side chains of membrane proteins projecting outward from the transmembrane segments would interact with the lipid membrane milieu, and ought to be considered buried, while the current algorithm may treat them as exposed. This trend can be gathered from the third panel in FIG. 8d, showing the environment of Rhodobacter capsulatus porin. For a visual impression, we arbitrarily converted the six side-chain environment categories (B1, B2, B3, P1, P2, and E) into respective environmental "hydrophobicities" [1-fraction polar)×(area buried)] using average values from FIG. 4 of (Bowie et al., 1991, Science, 253:164–170). In principle, each consecutive residue in a transmembrane β-strand might be expected to show a clear alternation in environment with respect to the prior one. Some limited alternation is detected for the strands (panel 3, FIG. 7d), but only rarely going into the high hydrophobicity region that would be expected for the bilayer environment. We believe that perhaps that is why the global scores we obtain in FIGS. 9a and 9b are lower than those obtained for globular proteins, and why the algorithm does not separate the protein scores as it otherwise might. Still, even with limitations, the algorithm is promising in that it does some discrimination consistent with expectations.

Functional possibilities for multimers.

Antiporters such as the $H^+/K^+$-ATPase, plus symports such as the $Na^+/K^+/2Cl^-$ transporters pose as questions whether the multiply transported ions might share the same route through the protein, and how could that be, especially for ions of opposite charge. Consideration of the porin arrangement leads us to speculate that perhaps the paths for the individual species might be separate, after all; each species might traverse the channel of a different "repeat", each one having its own suitable selectivity. Merging of the channels might account somehow for the stoichiometry observed.

Various publications are cited herein, the texts of which are hereby incorporated by reference in their entireties.

What is claimed is:

1. A method of predicting the tendency of a protein to form an amphiphilic α structure, comprising calculating a series of values for $U_{\alpha x}$ for a series of portions of the protein, each portion having a span of x residues, wherein the series of portions spans the protein, and wherein x is any integer, comprising calculating a value for $U_{\alpha x}$ using the equation $U_{\alpha x}=H_x+\mu_{\alpha x}-<pt>$, wherein $H_x$ is the average hydrophobicity for a span of x residues using the Kyte-Doolitte scale, $\mu_{\alpha x}$ is the hydrophobic moment (span x) for α structures, the angle between one residue and the successive residue being 100°, and <pt> is the position dependent turn propensity, and further comprising depicting the values for $U_{\alpha x}$ graphically to form a series of peaks, wherein peaks wide enough to correspond to a segment of the amino acid sequence long enough to span the membrane as an α-helix are predicted to be α structures.

2. The method according to claim 1, where x has a value of seven.

3. The method according to claim 1, where x has a value of twenty-one.

4. A method of predicting the tendency of a protein to form an amphiphilic β structure, comprising calculating a series of values for $U_{\beta x}$ for a series of portions of the protein, each portion having a span of x residues, wherein the series of portions spans the protein, and wherein x is any integer, comprising calculating a value for $U_{\beta x}$ using the equation $U_{\beta x}=H_x+\mu_{\beta x}-<pt>$, wherein $H_x$ is the average hydrophobicity for a span of x residues using the Kyte-Doolitte scale, $\mu_{\beta x}$ is the hydrophobic moment (span x) for β structures, the angle between one residue and the successive residue being 160°, and <pt> is the position dependent turn propensity, and further comprising depicting the values for $U_{\beta x}$ graphically to form a series of peaks, wherein peaks that are too narrow to correspond to a segment of the amino acid sequence long enough to span the membrane as an α-helix but which are wide enough to correspond to a segment of the amino acid sequence with a length between 6 and 14 amino acid residues are predicted to be β structures.

5. The method according to claim 4, where x has a value of seven.

6. The method according to claim 4, where x has a value of twenty-one.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 340 amino acids
      (B) TYPE: amino acid
      (C) STRANDEDNESS: single
      (D) TOPOLOGY: linear (ii) MOLECULE TYPE: peptide (vi) ORIGINAL SOURCE:
      (A) ORGANISM: Escherichia coli (ix) FEATURE:
      (A) NAME/KEY: Peptide
      (B) LOCATION: 1..340
      (C) OTHER INFORMATION: OmpF porin protein (xi) SEQUENCE DESCRIPTION: SEQ ID NO:1:

```
Ala Glu Ile Tyr Asn Lys Asp Gly Asn Lys Val Asp Leu Tyr Gly Lys
1               5                   10                  15

Ala Val Gly Leu His Tyr Arg Ser Lys Gly Asn Gly Glu Asn Ser Tyr
            20                  25                  30

Gly Gly Asn Gly Asp Met Thr Tyr Ala Arg Leu Gly Phe Lys Gly Glu
                35                  40                  45

Thr Gln Ile Asn Ser Asp Leu Thr Gly Tyr Gly Gln Trp Glu Tyr Asn
            50                  55                  60

Phe Gln Gly Asn Asn Ser Glu Gly Ala Asp Ala Gln Thr Gly Asn Lys
65                  70                  75                  80

Thr Arg Leu Ala Phe Ala Gly Leu Lys Tyr Ala Asp Val Gly Ser Phe
                85                  90                  95

Asp Tyr Gly Arg Asn Tyr Gly Val Val Tyr Asp Ala Leu Gly Tyr Thr
            100                 105                 110

Asp Met Leu Pro Glu Phe Gly Gly Asp Thr Ala Tyr Ser Asp Asp Phe
            115                 120                 125

Phe Val Gly Arg Val Gly Gly Val Ala Thr Tyr Arg Asn Ser Asn Phe
130                 135                 140

Phe Gly Leu Val Asp Gly Leu Asn Phe Ala Val Gln Tyr Leu Gly Lys
145                 150                 155                 160

Asn Glu Arg Asp Thr Ala Arg Arg Ser Asn Gly Asp Gly Val Gly Gly
                165                 170                 175

Ser Ile Ser Tyr Glu Tyr Asx Gly Phe Gly Ile Val Gly Ala Tyr Gly
            180                 185                 190

Ala Ala Asp Arg Thr Asn Leu Gln Glu Ala Gln Pro Leu Gly Asn Gly
            195                 200                 205

Lys Lys Ala Glu Gln Trp Ala Thr Gly Leu Lys Tyr Asp Ala Asn Asn
210                 215                 220

Ile Tyr Leu Ala Ala Asn Tyr Gly Glu Thr Arg Asn Ala Thr Pro Ile
225                 230                 235                 240

Thr Asn Lys Phe Thr Asn Thr Ser Gly Phe Ala Asn Lys Thr Gln Asp
                245                 250                 255

Val Leu Leu Val Ala Gln Tyr Gln Phe Asp Phe Gly Leu Arg Pro Ser
            260                 265                 270
```

-continued

```
            Ile Ala Tyr Thr Lys Ser Lys Ala Lys Asp Val Glu Gly Ile Gly Asp
                    275                 280                 285

Val Asp Leu Val Asn Tyr Phe Glu Val Gly Ala Thr Tyr Tyr Phe Asn
                290                 295                 300

Lys Asn Met Ser Thr Tyr Val Asp Tyr Ile Ile Asn Gln Ile Asp Ser
            305                 310                 315                 320

Asp Asn Lys Leu Gly Val Gly Ser Asp Asp Thr Val Ala Val Gly Ile
                            325                 330                 335

Val Tyr Gln Phe
                        340
```

(2) INFORMATION FOR SEQ ID NO:2:

(i) SEQUENCE CHARACTERISTICS:
        (A) LENGTH: 301 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Rhodobacter capsulatus (ix) FEATURE:
        (A) NAME/KEY: Peptide
        (B) LOCATION: 1..301
        (C) OTHER INFORMATION: Porin protein (xi) SEQUENCE DESCRIPTION: SEQ ID NO:2:

```
            Glu Val Lys Leu Ser Gly Asp Ala Arg Met Gly Val Met Tyr Asn Gly
            1               5                   10                  15

Asp Asp Trp Asn Phe Ser Ser Arg Ser Arg Val Leu Phe Thr Met Ser
                            20                  25                  30

Gly Thr Thr Asp Ser Gly Leu Glu Phe Gly Ala Ser Phe Lys Ala His
                        35                  40                  45

Glu Ser Val Gly Ala Arg Thr Gly Glu Asp Gly Thr Val Phe Leu Ser
                    50                  55                  60

Gly Ala Phe Gly Lys Ile Glu Met Gly Asp Ala Leu Gly Ala Ser Glu
            65                  70                  75                  80

Ala Leu Phe Gly Asp Leu Tyr Glu Val Gly Tyr Thr Asp Leu Asp Asp
                            85                  90                  95

Arg Gly Gly Asn Asp Ile Pro Tyr Leu Thr Gly Asp Glu Arg Leu Thr
                        100                 105                 110

Ala Glu Asp Asn Pro Val Leu Leu Tyr Thr Tyr Ser Ala Gly Ala Phe
                    115                 120                 125

Ser Val Ala Ala Ser Met Ser Asp Gly Lys Val Gly Glu Thr Ser Glu
                130                 135                 140

Asp Asp Ala Gln Glu Met Ala Val Ala Ala Tyr Thr Phe Gly Asn
            145                 150                 155                 160

Tyr Thr Val Gly Leu Gly Tyr Glu Lys Ile Asp Ser Pro Asp Thr Ala
                            165                 170                 175

Leu Met Ala Asp Met Glu Gln Leu Glu Leu Ala Ala Ile Ala Lys Phe
                        180                 185                 190

Gly Ala Thr Asn Val Lys Ala Tyr Tyr Ala Asp Gly Glu Leu Asp Arg
                    195                 200                 205

Asp Phe Ala Arg Ala Val Phe Asp Leu Thr Pro Val Ala Ala Ala Ala
                210                 215                 220

Thr Ala Val Asp His Lys Ala Tyr Gly Leu Ser Val Asp Ser Thr Phe
            225                 230                 235                 240
```

```
        Gly Ala Thr Thr Val Gly Gly Tyr Val Gln Val Leu Asp Ile Asp Thr
                        245                 250                 255

Ile Asp Asp Val Thr Tyr Tyr Gly Leu Gly Ala Ser Tyr Asp Leu Gly
                        260                 265                 270

Gly Gly Ala Ser Ile Val Gly Gly Ile Ala Asp Asn Asp Leu Pro Asn
                        275                 280                 285

Ser Asp Asn Val Ala Asp Leu Gly Val Lys Phe Lys Phe
                        290                 295                 300

(2) INFORMATION FOR SEQ ID NO:3:

(i) SEQUENCE CHARACTERISTICS:
        (A) LENGTH: 492 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Human (ix) FEATURE:
        (A) NAME/KEY: Peptide
        (B) LOCATION: 1..492
        (C) OTHER INFORMATION: Facilitative glucose transportor
            Glut1 protein (xi) SEQUENCE DESCRIPTION: SEQ ID NO:3:

Met Glu Pro Ser Ser Lys Lys Leu Thr Gly Arg Leu Met Leu Ala Val
        1               5                   10                  15

Gly Gly Ala Val Leu Gly Ser Leu Gln Phe Gly Tyr Asn Thr Gly Val
                        20                  25                  30

Ile Asn Ala Pro Gln Lys Val Ile Glu Glu Phe Tyr Asn Gln Thr Trp
                        35                  40                  45

Val His Arg Tyr Gly Glu Ser Ile Leu Pro Thr Thr Leu Thr Thr Leu
                        50                  55                  60

Trp Ser Leu Ser Val Ala Ile Phe Ser Val Gly Gly Met Ile Gly Ser
        65                      70                  75                  80

Phe Ser Val Gly Leu Phe Val Asn Arg Phe Gly Arg Arg Asn Ser Met
                        85                  90                  95

Leu Met Met Asn Leu Leu Ala Phe Val Ser Ala Val Leu Met Gly Phe
                        100                 105                 110

Ser Lys Leu Gly Lys Ser Phe Glu Met Leu Ile Leu Gly Arg Phe Ile
                        115                 120                 125

Ile Gly Val Tyr Cys Gly Leu Thr Thr Gly Phe Val Pro Met Tyr Val
                        130                 135                 140

Gly Glu Val Ser Pro Thr Ala Phe Arg Gly Ala Leu Gly Thr Leu His
        145                     150                 155                 160

Gln Leu Gly Ile Val Val Gly Ile Leu Ile Ala Gln Val Phe Gly Leu
                        165                 170                 175

Asp Ser Ile Met Gly Asn Lys Asp Leu Trp Pro Leu Leu Leu Ser Ile
                        180                 185                 190

Ile Phe Ile Pro Ala Leu Leu Gln Cys Ile Val Ile Pro Phe Cys Pro
                        195                 200                 205

Glu Ser Pro Arg Phe Leu Leu Ile Asn Arg Asn Glu Glu Asn Arg Ala
                        210                 215                 220

Lys Ser Val Leu Lys Lys Leu Arg Gly Thr Ala Asp Val Thr His Asp
        225                     230                 235                 240
```

-continued

```
Leu Gln Glu Met Lys Glu Glu Ser Arg Gln Met Met Arg Glu Lys Lys
            245             250             255

Val Thr Ile Leu Glu Leu Phe Arg Ser Pro Ala Tyr Arg Gln Pro Ile
            260             265             270

Leu Ile Ala Val Val Leu Gln Leu Ser Gln Gln Leu Ser Gly Ile Asn
            275             280             285

Ala Val Phe Tyr Tyr Ser Thr Ser Ile Phe Glu Lys Ala Gly Val Gln
            290             295             300

Gln Pro Val Tyr Ala Thr Ile Gly Ser Gly Ile Val Asn Thr Ala Phe
305             310             315                         320

Thr Val Val Ser Leu Phe Val Val Glu Arg Ala Gly Arg Arg Thr Leu
                325             330             335

His Leu Ile Gly Leu Ala Gly Met Ala Gly Gln Ala Ile Leu Met Thr
            340             345             350

Ile Ala Leu Ala Leu Leu Glu Gln Leu Pro Trp Met Ser Tyr Leu Ser
            355             360             365

Ile Val Ala Ile Phe Gly Phe Val Ala Phe Phe Glu Val Gly Pro Gly
            370             375             380

Pro Ile Pro Trp Phe Ile Val Ala Glu Leu Glu Ser Gln Gly Pro Arg
385             390             395                         400

Pro Ala Ala Ile Ala Val Ala Gly Phe Ser Asn Trp Thr Ser Asn Phe
                405             410             415

Ile Val Gly Met Cys Phe Gln Tyr Val Glu Gln Leu Cys Gly Pro Tyr
                420             425             430

Val Phe Ile Ile Phe Thr Val Leu Leu Val Leu Phe Phe Ile Arg Thr
            435             440             445

Tyr Phe Lys Val Pro Glu Thr Lys Gly Arg Thr Phe Asp Glu Ile Ala
    450             455             460

Ser Gly Phe Arg Gln Gly Gly Ala Ser Gln Ser Asp Lys Thr Pro Glu
465             470             475                         480

Glu Leu Phe His Pro Leu Gly Ala Asp Ser Gln Val
            485             490
```